United States Patent
Dudkin et al.

(10) Patent No.: US 12,227,593 B2
(45) Date of Patent: Feb. 18, 2025

(54) SITE-SPECIFIC CONJUGATION OF GLYCOSYLATED MONOCLONAL ANTIBODIES WITH TRANSGLUTAMINASE

(71) Applicant: Janssen Biotech, Inc., Horsham, PA (US)

(72) Inventors: Vadim Dudkin, Chalfont, PA (US); Shalom Goldberg, Merion Station, PA (US); Michael J. McCauley, Abington, PA (US); Kristen Wiley, Trappe, PA (US); Rebecca Wissner, Philadelphia, PA (US)

(73) Assignee: Janssen Biotech, Inc., Horsham, PA (US)

( * ) Notice: Subject to any disclaimer, the term of this patent is extended or adjusted under 35 U.S.C. 154(b) by 505 days.

(21) Appl. No.: 17/324,148

(22) Filed: May 19, 2021

(65) Prior Publication Data
US 2021/0388085 A1 Dec. 16, 2021

Related U.S. Application Data

(60) Provisional application No. 63/027,396, filed on May 20, 2020.

(51) Int. Cl.
*C07K 16/32* (2006.01)
*A61K 47/68* (2017.01)
*C07K 16/28* (2006.01)
*C12N 9/10* (2006.01)

(52) U.S. Cl.
CPC ........ *C07K 16/32* (2013.01); *A61K 47/68031* (2023.08); *A61K 47/6849* (2017.08); *C07K 16/2803* (2013.01); *C12N 9/1044* (2013.01); *C07K 2317/21* (2013.01); *C07K 2317/32* (2013.01); *C07K 2317/94* (2013.01); *C12Y 203/02013* (2013.01)

(58) Field of Classification Search
CPC ............ C07K 16/2803; C07K 2317/21; C07K 2317/32; C07K 2317/94; A61K 47/6803; A61K 47/6849; C12N 9/1044; C12Y 203/02013
USPC ..................................................... 424/133.1
See application file for complete search history.

(56) References Cited

U.S. PATENT DOCUMENTS

| | | | |
|---|---|---|---|
| 2013/0266512 A1 | 10/2013 | Fox et al. | |
| 2016/0215061 A1* | 7/2016 | Shaheen ................ | C07K 16/32 |
| 2016/0271270 A1* | 9/2016 | Maderna .............. | C07K 5/0815 |
| 2020/0024360 A1 | 1/2020 | Anderson et al. | |

FOREIGN PATENT DOCUMENTS

| | | | |
|---|---|---|---|
| WO | WO 2015073746 A2 | 5/2015 | |
| WO | WO2015/191883 | 12/2015 | |
| WO | WO 2018007453 | * 1/2018 | ............. C07K 16/28 |
| WO | WO2019/057772 | 3/2019 | |
| WO | WO 2019125982 A1 | 6/2019 | |
| WO | WO 2019224718 A2 | 11/2019 | |

OTHER PUBLICATIONS

Machine translation of WO 2018007453 (Jan. 11, 2018, pp. 1-19).*
Schneider et al., "recent progress in transglutaminase-mediated assemblyof antibody-drug conjugates.", Analytical Biochemistry, Feb. 5, 2020, pp. 1-13, vol. 595.
Chandler et al., "Multi-isotype Glycoproteomic Characterization of Serun Antibody Heav Chains Reveals Isotype-and Subclass-Specific N-Glycosylation Profiles.", Molecular & Cellular Proteomics, Apr. 2019, pp. 686-703, vol. 18(4).
Dennler et al., "Enzymatic Antibody Modification by Bacterial Transglutaminase", Antibody-Drug Conjugates, Methods in Molecular Biology, Jan. 1, 2013, pp. 205-215, vol. 1045, XP009178016.
International Search Report issued in corresponding PCT Patent Application No. PCT/IB2021/054308, filed on May 19, 2021. Mailing Date of International Search Report: Dec. 10, 2021.
Written Opinion issued in corresponding PCT Patent Application No. PCT/IB2021/054308, filed on May 19, 2021. Mailing Date of Written Opinion: Dec. 10, 2021.
International Search Report issued in related PCT Patent Application No. PCT/IB2021/054310, filed on May 19, 2021. Mailing Date of International Search Report: Sep. 27, 2021.
Written Opinion issued in related PCT Patent Application No. PCT/IB2021/054310, filed on May 19, 2021. Mailing Date of Written Opinion: Sep. 27, 2021.
Agarwal and Bertozzi, "Site-Specific Antibody-Drug Conjugates: The Nexus of Bioorthogonal Chemistry, Protein Engineering, and Drug Development.", Bioconjug Chem, 2015, pp. 176-192, vol. 26(2).
Ahmed et al., "Structural Characterization of Anti-Inflammatory Immunoglobulin G Fc Proteins.", J Mol Biol, 2014, pp. 3166-3179, vol. 426(18).
Bethea et al., "Mechanisms of self-association of a human monoclonal antibody CNTO607.", Prot Eng Des Sel, 2012, pp. 531-537, vol. 25(10).
Chothia & Lesk, "Canonical Structures for the Hypervariable Regions of Immunoglobins." J. Mol. Biol., 1987, pp. 901-907, vol. 196.
Chothia et al., "Conformations of Immunoglobulin hypervariable regions.", Nature, 1989, pp. 878-883, vol. 342.
Dall'Acqua et al., "Properties of Human IgG1s Engineered for Enhanced Binding to the Neonatal Fc Receptor (FcRn)*.", J Biol Chem, Aug. 18, 2006, pp. 23514-23524, vol. 281(33).
Dennler et al., "Microbial Transglutaminase and c-myc-Tag: a Strong Couple for the Functionalization of Antibody-Like Protein Scaffolds from Discovery Platforms.", Chembiochem, 2015, pp. 861-867, vol. 16(5).
Houde D. et al., "Characterization of IgG1 Conformation and Conformational Dynamics by Hydrogen/Deuterium Exchange Mass Spectrometry.", Anal Chem., 2009, pp. 2644-2651, vol. 81(7).

(Continued)

*Primary Examiner* — Yan Xiao
(74) *Attorney, Agent, or Firm* — Ice Miller LLP

(57) ABSTRACT

Engineered antibodies useful for site-specific conjugation by a transglutaminase are described. Also described are methods of site-specific conjugation of the antibodies, the site-specifically conjugated antibodies, and pharmaceutical compositions and uses related to the site-specifically conjugated antibodies.

45 Claims, 12 Drawing Sheets

Specification includes a Sequence Listing.

(56) References Cited

OTHER PUBLICATIONS

Jeger et al., "Site-Specific and Stoichiometric Modification of Antibodies by Bacterial Transglutaminase**.", Angewandte Chemie, 2010, pp. 9995-9997, vol. 49(51).

Kabat and Wu, "Identical V Region Amino Acid Sequences and Segments of Sequences in Antibodies of Different Specificities. Relative Contributions of VH and VL Genes, Minigenesm and Complimentary Determining Regions to Binding of Antibody-Combining Sites.", J Immunol, Sep. 1991, pp. 1709-1719, vol. 147(5).

Kolb, et al., "Click Chemistry: Diverse Chemical Function from a Few Good Reactions.", Angew Chem Int Ed Engl., Jun. 1, 2001, pp. 2004-2021, vol. 40(11).

Liu et al., "High-throughput screening for developability during early-stage antibody discovery using selfinteraction nanoparticle spectroscopy.", mAbs, Mar./Apr. 2014, pp. 483-492, vol. 6(2).

Mackness et al., "Antibody Fc engineering for enhanced neonatal Fc receptor binding and prolonged circulation half-life.", mAbs, 2019, pp. 1276-1288, vol. 11(7).

Majumdar et al., "Correlations between changes in conformational dynamics and physical stability in a mutant IgG1 mAb engineered for extended serum half-life.", Mabs, 2015, pp. 84-95, vol. 7(1).

Mero et al., "A new method to increase selectivity of transglutaminase mediated PEGylation of salmon calcitonin and human growth hormone.", J Control Release, 2011, pp. 27-34, vol. 154(1).

Nahta and Esteva, "Trastuzumab: triumphs and tribulations.", Oncogene, 2007, pp. 3637-3643, vol. 26(25).

Sato, H., "Enzymatic procedure for site-specific pegylation of proteins.", Advanced drug delivery reviews, 2002, pp. 487-504, vol. 54(4).

Savoca et al., "Biocatalysis by Transglutaminases: a Review of Biotechnological Applications.", Micromachines, 2018, pp. 1-23, vol. 9(562), Basel.

Spicer and Davis, "Selective chemical protein modification.", Nature Communications, 2014, pp. 1-14, 5:4740.

Spolaore et al., "Local Unfolding is Required for the Site-Specific Protein Modification by Transglutaminase.", Biochemistry, 2012, pp. 8679-8689, vol. 51.

Spolaore et al., "Site-Specific Transglutaminase-Mediated Conjugation of Interferon α-2b at Glutamine or Lysine Residues.", Bioconjugate chemistry, 2016, pp. 3695-3706, vol. 27(11).

Strop et al., "Location Matters: Site of Conjugation Modulates Stability and Pharmacokinetics of Antibody Drug Conjugates.", Chem Biol, Feb. 21, 2013, pp. 161-167, vol. 20(2).

Sugimura et al., "Identification of preferred substrate sequences of microbial transglutaminase from Streptomyces mobaraensis using a phage-displayed peptide library.", Arch Biochem Biophys, 2008, pp. 379-383, vol. 477(2).

Wada et al., "Influence of N-glycosylation on effector functions and thermal stability of glycoengineered IgG1 monoclonal antibody with homogeneous glycoforms.", Mabs, 2019, pp. 350-371, vol. 11(2).

* cited by examiner

Melting temperature

Aggregation temperature

SEQUENCE LISTING

<160> NUMBER OF SEQ ID NOS: 59

<210> SEQ ID NO 1
<211> LENGTH: 214
<212> TYPE: PRT
<213> ORGANISM: Artificial Sequence
<220> FEATURE:
<223> OTHER INFORMATION: Trastuzumab light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

-continued

```
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 2
<211> LENGTH: 450
<212> TYPE: PRT
<213> ORGANISM: Artificial Sequence
<220> FEATURE:
<223> OTHER INFORMATION: Trastuzumab heavy chain

<400> SEQUENCE: 2

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 450
<212> TYPE: PRT
<213> ORGANISM: Artificial Sequence
<220> FEATURE:
<223> OTHER INFORMATION: K288Q

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Gln Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 4
<211> LENGTH: 450
<212> TYPE: PRT
<213> ORGANISM: Artificial Sequence
<220> FEATURE:
<223> OTHER INFORMATION: K288Q/P291A/R292P

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Gln Thr Lys Ala Pro Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 5
<211> LENGTH: 450
<212> TYPE: PRT
<213> ORGANISM: Artificial Sequence
<220> FEATURE:
<223> OTHER INFORMATION: K288Q/Y300L/V302S

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Gln Thr Lys Pro Arg Glu Glu Gln Tyr Asn Ser Thr Leu Arg
290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 6
<211> LENGTH: 450
<212> TYPE: PRT
<213> ORGANISM: Artificial Sequence
<220> FEATURE:
<223> OTHER INFORMATION: K288Q/P291A/R292P/Y300L/V302S

<400> SEQUENCE: 6

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
                20                  25                  30
Tyr Ile His Trp Val Arg Gln Ala Pro Gly Lys Gly Leu Glu Trp Val
                35                  40                  45
Ala Arg Ile Tyr Pro Thr Asn Gly Tyr Thr Arg Tyr Ala Asp Ser Val
            50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
```

```
Asp Pro Glu Val Lys Phe Asn Trp Tyr Val Asp Gly Val Glu Val His
            275                 280                 285

Asn Ala Gln Thr Lys Ala Pro Glu Glu Gln Tyr Asn Ser Thr Leu Arg
        290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 7
<211> LENGTH: 450
<212> TYPE: PRT
<213> ORGANISM: Artificial Sequence
<220> FEATURE:
<223> OTHER INFORMATION: K288Q/K290H

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Gln Thr His Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 8
<211> LENGTH: 450
<212> TYPE: PRT
<213> ORGANISM: Artificial Sequence
<220> FEATURE:
<223> OTHER INFORMATION: K288Q/V305E

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Gln Thr Lys Pro Arg Glu Glu Gln Tyr Asn Ser Thr Tyr Arg
290                 295                 300

Val Val Ser Glu Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 9
<211> LENGTH: 450
<212> TYPE: PRT
<213> ORGANISM: Artificial Sequence
<220> FEATURE:
<223> OTHER INFORMATION: K288Q/E258K

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Lys Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Gln Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 10
<211> LENGTH: 450
<212> TYPE: PRT
<213> ORGANISM: Artificial Sequence
<220> FEATURE:
<223> OTHER INFORMATION: K288Q/K290H/V305E

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Gln Thr His Pro Arg Glu Glu Gln Tyr Asn Ser Thr Tyr Arg
    290                 295                 300

Val Val Ser Glu Leu Thr Val Leu His Gln Asp Trp Leu Asn Gly Lys

```
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 11
<211> LENGTH: 450
<212> TYPE: PRT
<213> ORGANISM: Artificial Sequence
<220> FEATURE:
<223> OTHER INFORMATION: K288Q/K290H/V305E/E258K

<400> SEQUENCE: 11

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
                20                  25                  30
Tyr Ile His Trp Val Arg Gln Ala Pro Gly Lys Gly Leu Glu Trp Val
                35                  40                  45
Ala Arg Ile Tyr Pro Thr Asn Gly Tyr Thr Arg Tyr Ala Asp Ser Val
                50                  55                  60
Lys Gly Arg Phe Thr Ile Ser Ala Asp Thr Ser Lys Asn Thr Ala Tyr
65              70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
```

```
                    210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Lys Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Gln Thr His Pro Arg Glu Glu Gln Tyr Asn Ser Thr Tyr Arg
    290                 295                 300

Val Val Ser Glu Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 12
<211> LENGTH: 450
<212> TYPE: PRT
<213> ORGANISM: Artificial Sequence
<220> FEATURE:
<223> OTHER INFORMATION: C'/D strand

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Thr Ala Gln Thr His Ala Pro Glu Lys Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 13
<211> LENGTH: 450
<212> TYPE: PRT
<213> ORGANISM: Artificial Sequence
<220> FEATURE:
<223> OTHER INFORMATION: C'/D-E strands

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

-continued

```
                20                  25                  30
Tyr Ile His Trp Val Arg Gln Ala Pro Gly Lys Gly Leu Glu Trp Val
            35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Thr Ala Gln Thr His Ala Pro Glu Lys Gln Ser Asn Ser Thr Leu Arg
290                 295                 300
Ser Val Ser Glu Leu Pro Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
    450

<210> SEQ ID NO 14
<211> LENGTH: 450
<212> TYPE: PRT
<213> ORGANISM: Artificial Sequence
<220> FEATURE:
<223> OTHER INFORMATION: C'/D-E strands + E258K

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Lys Val Thr Cys Val Val Asp Val Ser His Glu
            260                 265                 270

Asp Pro Glu Val Lys Phe Asn Trp Tyr Val Asp Gly Val Glu Val His
        275                 280                 285

Thr Ala Gln Thr His Ala Pro Glu Lys Gln Ser Asn Ser Thr Leu Arg
    290                 295                 300

Ser Val Ser Glu Leu Pro Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 15
<211> LENGTH: 450
<212> TYPE: PRT
<213> ORGANISM: Artificial Sequence
<220> FEATURE:
<223> OTHER INFORMATION: K288Q + PR->AP; YRV->LRS; K290H, V305E, E258K

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Lys Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Gln Thr His Ala Pro Glu Glu Gln Tyr Asn Ser Thr Leu Arg
    290                 295                 300

Ser Val Ser Glu Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly Lys
    450

<210> SEQ ID NO 16
<211> LENGTH: 450
<212> TYPE: PRT
<213> ORGANISM: Artificial Sequence
<220> FEATURE:
<223> OTHER INFORMATION: Graft entire CH2 domain

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Ser Ser Val Phe Ile Phe Pro Pro Lys Thr Lys Asp Val Leu Thr Ile
                245                 250                 255

Thr Leu Thr Pro Lys Val Thr Cys Val Val Val Asp Ile Ser Gln Asn
            260                 265                 270

Asp Pro Glu Val Arg Phe Ser Trp Phe Ile Asp Asp Val Glu Val His
        275                 280                 285

Thr Ala Gln Thr His Ala Pro Glu Lys Gln Ser Asn Ser Thr Leu Arg
    290                 295                 300

Ser Val Ser Glu Leu Pro Ile Val His Arg Asp Trp Leu Asn Gly Lys
305                 310                 315                 320

Thr Phe Lys Cys Lys Val Asn Ser Gly Ala Phe Pro Ala Pro Ile Glu
                325                 330                 335

Lys Ser Ile Ser Lys Pro Glu Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 17
<211> LENGTH: 450
<212> TYPE: PRT
<213> ORGANISM: Artificial Sequence
<220> FEATURE:
<223> OTHER INFORMATION: R301A

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Ala
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 18
<211> LENGTH: 450
```

<212> TYPE: PRT
<213> ORGANISM: Artificial Sequence
<220> FEATURE:
<223> OTHER INFORMATION: F241A

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Ala Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 19
<211> LENGTH: 450
<212> TYPE: PRT
<213> ORGANISM: Artificial Sequence
<220> FEATURE:
<223> OTHER INFORMATION: F243A

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Ala Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 20
<211> LENGTH: 450
<212> TYPE: PRT
<213> ORGANISM: Artificial Sequence
<220> FEATURE:
<223> OTHER INFORMATION: K288Q/Y300L

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Gln Thr Lys Pro Arg Glu Glu Gln Tyr Asn Ser Thr Leu Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 21
<211> LENGTH: 450
<212> TYPE: PRT
<213> ORGANISM: Artificial Sequence
<220> FEATURE:
<223> OTHER INFORMATION: K288Q/V302S

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Gln Thr Lys Pro Arg Glu Glu Gln Tyr Asn Ser Thr Tyr Arg
    290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 450
<212> TYPE: PRT
<213> ORGANISM: Artificial Sequence
<220> FEATURE:
<223> OTHER INFORMATION: Y300L/V302S

<400> SEQUENCE: 22
```

-continued

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Leu Arg
290                 295                 300
Ser Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
```

```
                420                 425                 430
Glu Ala Leu His Asn His Tyr Thr Gln Lys Ser Leu Ser Leu Ser Pro
            435                 440                 445
Gly Lys
    450

<210> SEQ ID NO 23
<211> LENGTH: 450
<212> TYPE: PRT
<213> ORGANISM: Artificial Sequence
<220> FEATURE:
<223> OTHER INFORMATION: Y300L

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Leu Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                      325                 330                 335
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 24
<211> LENGTH: 450
<212> TYPE: PRT
<213> ORGANISM: Artificial Sequence
<220> FEATURE:
<223> OTHER INFORMATION: V302S

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
            225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 25
<211> LENGTH: 450
<212> TYPE: PRT
<213> ORGANISM: Artificial Sequence
<220> FEATURE:
<223> OTHER INFORMATION: K288Q/E294A

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
                130              135              140
Leu Gly Cys Leu Val Lys Asp Tyr Phe Pro Glu Pro Val Thr Val Ser
145                  150                  155                 160

Trp Asn Ser Gly Ala Leu Thr Ser Gly Val His Thr Phe Pro Ala Val
                165                  170                  175

Leu Gln Ser Ser Gly Leu Tyr Ser Leu Ser Ser Val Val Thr Val Pro
            180                  185                  190

Ser Ser Ser Leu Gly Thr Gln Thr Tyr Ile Cys Asn Val Asn His Lys
        195                  200                  205

Pro Ser Asn Thr Lys Val Asp Lys Lys Val Glu Pro Lys Ser Cys Asp
    210                  215                  220

Lys Thr His Thr Cys Pro Pro Cys Pro Ala Pro Glu Leu Leu Gly Gly
225                  230                  235                 240

Pro Ser Val Phe Leu Phe Pro Pro Lys Pro Lys Asp Thr Leu Met Ile
                245                  250                  255

Ser Arg Thr Pro Glu Val Thr Cys Val Val Val Asp Val Ser His Glu
            260                  265                  270

Asp Pro Glu Val Lys Phe Asn Trp Tyr Val Asp Gly Val Glu Val His
        275                  280                  285

Asn Ala Gln Thr Lys Pro Arg Glu Ala Gln Tyr Asn Ser Thr Tyr Arg
    290                  295                  300

Val Val Ser Val Leu Thr Val Leu His Gln Asp Trp Leu Asn Gly Lys
305                  310                  315                 320

Glu Tyr Lys Cys Lys Val Ser Asn Lys Ala Leu Pro Ala Pro Ile Glu
                325                  330                  335

Lys Thr Ile Ser Lys Ala Lys Gly Gln Pro Arg Glu Pro Gln Val Tyr
            340                  345                  350

Thr Leu Pro Pro Ser Arg Asp Glu Leu Thr Lys Asn Gln Val Ser Leu
        355                  360                  365

Thr Cys Leu Val Lys Gly Phe Tyr Pro Ser Asp Ile Ala Val Glu Trp
    370                  375                  380

Glu Ser Asn Gly Gln Pro Glu Asn Asn Tyr Lys Thr Thr Pro Pro Val
385                  390                  395                 400

Leu Asp Ser Asp Gly Ser Phe Phe Leu Tyr Ser Lys Leu Thr Val Asp
                405                  410                  415

Lys Ser Arg Trp Gln Gln Gly Asn Val Phe Ser Cys Ser Val Met His
            420                  425                  430

Glu Ala Leu His Asn His Tyr Thr Gln Lys Ser Leu Ser Leu Ser Pro
        435                  440                  445

Gly Lys
    450

<210> SEQ ID NO 26
<211> LENGTH: 450
<212> TYPE: PRT
<213> ORGANISM: Artificial Sequence
<220> FEATURE:
<223> OTHER INFORMATION: H285Q/Y300L/V302S

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val Gln
            275                 280                 285
Asn Ala Lys Thr Lys Pro Arg Glu Glu Gln Tyr Asn Ser Thr Leu Arg
            290                 295                 300
Ser Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
 450
```

<210> SEQ ID NO 27
<211> LENGTH: 450
<212> TYPE: PRT
<213> ORGANISM: Artificial Sequence
<220> FEATURE:
<223> OTHER INFORMATION: N286Q/Y300L/V302S

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Gln Ala Lys Thr Lys Pro Arg Glu Glu Gln Tyr Asn Ser Thr Leu Arg
    290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 28
<211> LENGTH: 450
<212> TYPE: PRT
<213> ORGANISM: Artificial Sequence
<220> FEATURE:
<223> OTHER INFORMATION: A287Q/Y300L/V302S

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Gln Lys Thr Lys Pro Arg Glu Glu Gln Tyr Asn Ser Thr Leu Arg
    290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 29
<211> LENGTH: 450
<212> TYPE: PRT
<213> ORGANISM: Artificial Sequence
<220> FEATURE:
<223> OTHER INFORMATION: T289Q/Y300L/V302S

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Gln Lys Pro Arg Glu Glu Gln Tyr Asn Ser Thr Leu Arg
            290                 295                 300
Ser Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
    450

<210> SEQ ID NO 30
<211> LENGTH: 450
<212> TYPE: PRT
<213> ORGANISM: Artificial Sequence
<220> FEATURE:
<223> OTHER INFORMATION: K290Q/Y300L/V302S

<400> SEQUENCE: 30

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
            35                  40                  45
Ala Arg Ile Tyr Pro Thr Asn Gly Tyr Thr Arg Tyr Ala Asp Ser Val
            50                  55                  60
Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Gln Pro Arg Glu Glu Gln Tyr Asn Ser Thr Leu Arg
290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 450
<212> TYPE: PRT
<213> ORGANISM: Artificial Sequence
<220> FEATURE:

<223> OTHER INFORMATION: R292Q/Y300L/V302S

<400> SEQUENCE: 31

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Gln Glu Glu Gln Tyr Asn Ser Thr Leu Arg
    290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 32
<211> LENGTH: 450
<212> TYPE: PRT
<213> ORGANISM: Artificial Sequence
<220> FEATURE:
<223> OTHER INFORMATION: E293Q/Y300L/V302S

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Gln Glu Gln Tyr Asn Ser Thr Leu Arg
    290                 295                 300
```

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 33
<211> LENGTH: 450
<212> TYPE: PRT
<213> ORGANISM: Artificial Sequence
<220> FEATURE:
<223> OTHER INFORMATION: E294Q/Y300L/V302S

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Gln Gln Tyr Asn Ser Thr Leu Arg
290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 34
<211> LENGTH: 450
<212> TYPE: PRT
<213> ORGANISM: Artificial Sequence
<220> FEATURE:
<223> OTHER INFORMATION: K288Q YTE

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Gln Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 35
<211> LENGTH: 450
<212> TYPE: PRT
<213> ORGANISM: Artificial Sequence
<220> FEATURE:
<223> OTHER INFORMATION: V302A

<400> SEQUENCE: 35

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
         20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Ala Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

```
                435                 440                 445

Gly Lys
    450

<210> SEQ ID NO 36
<211> LENGTH: 450
<212> TYPE: PRT
<213> ORGANISM: Artificial Sequence
<220> FEATURE:
<223> OTHER INFORMATION: V302I

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Ile Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

```
              340                 345                 350
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 37
<211> LENGTH: 450
<212> TYPE: PRT
<213> ORGANISM: Artificial Sequence
<220> FEATURE:
<223> OTHER INFORMATION: V302L

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                         245                 250                 255
Ser Arg Thr Pro Glu Val Thr Cys Val Val Asp Val Ser His Glu
                    260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Leu Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 38
<211> LENGTH: 450
<212> TYPE: PRT
<213> ORGANISM: Artificial Sequence
<220> FEATURE:
<223> OTHER INFORMATION: V302M

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
        Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys Asp
                    210                 215                 220

Lys Thr His Thr Cys Pro Pro Cys Pro Ala Pro Glu Leu Leu Gly Gly
        225                 230                 235                 240

Pro Ser Val Phe Leu Phe Pro Pro Lys Pro Lys Asp Thr Leu Met Ile
                            245                 250                 255

Ser Arg Thr Pro Glu Val Thr Cys Val Val Val Asp Val Ser His Glu
                        260                 265                 270

Asp Pro Glu Val Lys Phe Asn Trp Tyr Val Asp Gly Val Glu Val His
                    275                 280                 285

Asn Ala Lys Thr Lys Pro Arg Glu Glu Gln Tyr Asn Ser Thr Tyr Arg
            290                 295                 300

Met Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                            325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                    355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                            405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                    435                 440                 445

Gly Lys
            450

<210> SEQ ID NO 39
<211> LENGTH: 450
<212> TYPE: PRT
<213> ORGANISM: Artificial Sequence
<220> FEATURE:
<223> OTHER INFORMATION: V302T

<400> SEQUENCE: 39

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Asn Ile Lys Asp Thr
                        20                  25                  30

Tyr Ile His Trp Val Arg Gln Ala Pro Gly Lys Gly Leu Glu Trp Val
                    35                  40                  45

Ala Arg Ile Tyr Pro Thr Asn Gly Tyr Thr Arg Tyr Ala Asp Ser Val
```

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Thr Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 40
```

<211> LENGTH: 450
<212> TYPE: PRT
<213> ORGANISM: Artificial Sequence
<220> FEATURE:
<223> OTHER INFORMATION: V302F

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Phe Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly Lys
    450

<210> SEQ ID NO 41
<211> LENGTH: 450
<212> TYPE: PRT
<213> ORGANISM: Artificial Sequence
<220> FEATURE:
<223> OTHER INFORMATION: V302Y

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
        290                 295                 300

Tyr Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 42
<211> LENGTH: 450
<212> TYPE: PRT
<213> ORGANISM: Artificial Sequence
<220> FEATURE:
<223> OTHER INFORMATION: E294Q

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Gln Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 43
<211> LENGTH: 450
<212> TYPE: PRT
<213> ORGANISM: Artificial Sequence
<220> FEATURE:
<223> OTHER INFORMATION: E293Q

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Gln Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 44
<211> LENGTH: 450
<212> TYPE: PRT
<213> ORGANISM: Artificial Sequence
<220> FEATURE:
<223> OTHER INFORMATION: V302S/E294Q

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Gln Gln Tyr Asn Ser Thr Tyr Arg
290                 295                 300

Ser Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 45
<211> LENGTH: 450
<212> TYPE: PRT
<213> ORGANISM: Artificial Sequence
<220> FEATURE:
<223> OTHER INFORMATION: V302S/E293Q

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Gln Glu Gln Tyr Asn Ser Thr Tyr Arg
    290                 295                 300

Ser Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 46
<211> LENGTH: 450
<212> TYPE: PRT
<213> ORGANISM: Artificial Sequence
<220> FEATURE:
<223> OTHER INFORMATION: E294A

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Ala Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 47
<211> LENGTH: 450
<212> TYPE: PRT
<213> ORGANISM: Artificial Sequence
<220> FEATURE:
<223> OTHER INFORMATION: E294D

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
        100                 105                 110

Gly Thr Leu Val Thr Val Ser Ser Ala Ser Thr Lys Gly Pro Ser Val
    115                 120                 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Asp Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 48
<211> LENGTH: 450
<212> TYPE: PRT
<213> ORGANISM: Artificial Sequence
<220> FEATURE:
<223> OTHER INFORMATION: E294F

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Phe Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
```

<210> SEQ ID NO 49
<211> LENGTH: 450
<212> TYPE: PRT
<213> ORGANISM: Artificial Sequence
<220> FEATURE:
<223> OTHER INFORMATION: E294G

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Gly Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
                355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
                435                 440                 445
Gly Lys
    450

<210> SEQ ID NO 50
<211> LENGTH: 450
<212> TYPE: PRT
<213> ORGANISM: Artificial Sequence
<220> FEATURE:
<223> OTHER INFORMATION: E294H

<400> SEQUENCE: 50

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
                20                  25                  30
Tyr Ile His Trp Val Arg Gln Ala Pro Gly Lys Gly Leu Glu Trp Val
            35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
```

```
            260                 265                 270
Asp Pro Glu Val Lys Phe Asn Trp Tyr Val Asp Gly Val Glu Val His
            275                 280                 285
Asn Ala Lys Thr Lys Pro Arg Glu His Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 51
<211> LENGTH: 450
<212> TYPE: PRT
<213> ORGANISM: Artificial Sequence
<220> FEATURE:
<223> OTHER INFORMATION: E294K

<400> SEQUENCE: 51

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Lys Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 52
<211> LENGTH: 450
<212> TYPE: PRT
<213> ORGANISM: Artificial Sequence
<220> FEATURE:
<223> OTHER INFORMATION: E294L

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
```

```
            65                  70                  75                  80
Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
                100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Leu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 53
<211> LENGTH: 450
<212> TYPE: PRT
<213> ORGANISM: Artificial Sequence
```

<220> FEATURE:
<223> OTHER INFORMATION: E294M

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Met Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 54
<211> LENGTH: 450
<212> TYPE: PRT
<213> ORGANISM: Artificial Sequence
<220> FEATURE:
<223> OTHER INFORMATION: E294N

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Asn Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 55
<211> LENGTH: 450
<212> TYPE: PRT
<213> ORGANISM: Artificial Sequence
<220> FEATURE:
<223> OTHER INFORMATION: E294R

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Arg Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 56
<211> LENGTH: 450
<212> TYPE: PRT
<213> ORGANISM: Artificial Sequence
<220> FEATURE:
<223> OTHER INFORMATION: E294S

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Ser Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 57
<211> LENGTH: 450
<212> TYPE: PRT
<213> ORGANISM: Artificial Sequence
<220> FEATURE:
<223> OTHER INFORMATION: E294T

<400> SEQUENCE: 57

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
            20              25                  30

Tyr Ile His Trp Val Arg Gln Ala Pro Gly Lys Gly Leu Glu Trp Val
            35              40                  45

Ala Arg Ile Tyr Pro Thr Asn Gly Tyr Thr Arg Tyr Ala Asp Ser Val
 50              55                  60

Lys Gly Arg Phe Thr Ile Ser Ala Asp Thr Ser Lys Asn Thr Ala Tyr
 65                  70              75                      80

Leu Gln Met Asn Ser Leu Arg Ala Glu Asp Thr Ala Val Tyr Tyr Cys
                85              90                  95

Ser Arg Trp Gly Gly Asp Gly Phe Tyr Ala Met Asp Tyr Trp Gly Gln
            100             105                 110

Gly Thr Leu Val Thr Val Ser Ser Ala Ser Thr Lys Gly Pro Ser Val
            115             120                 125

Phe Pro Leu Ala Pro Ser Ser Lys Ser Thr Ser Gly Gly Thr Ala Ala
 130             135                 140

Leu Gly Cys Leu Val Lys Asp Tyr Phe Pro Glu Pro Val Thr Val Ser
145             150                 155                     160

Trp Asn Ser Gly Ala Leu Thr Ser Gly Val His Thr Phe Pro Ala Val
                165             170                 175

Leu Gln Ser Ser Gly Leu Tyr Ser Leu Ser Ser Val Val Thr Val Pro
            180             185                 190

Ser Ser Ser Leu Gly Thr Gln Thr Tyr Ile Cys Asn Val Asn His Lys
            195             200                 205

Pro Ser Asn Thr Lys Val Asp Lys Lys Val Glu Pro Lys Ser Cys Asp
    210             215                 220

Lys Thr His Thr Cys Pro Pro Cys Pro Ala Pro Glu Leu Leu Gly Gly
225             230                 235                     240

Pro Ser Val Phe Leu Phe Pro Pro Lys Pro Lys Asp Thr Leu Met Ile
                245             250                 255

Ser Arg Thr Pro Glu Val Thr Cys Val Val Val Asp Val Ser His Glu
            260             265                 270

Asp Pro Glu Val Lys Phe Asn Trp Tyr Val Asp Gly Val Glu Val His
            275             280                 285

Asn Ala Lys Thr Lys Pro Arg Glu Thr Gln Tyr Asn Ser Thr Tyr Arg
 290             295                 300

Val Val Ser Val Leu Thr Val Leu His Gln Asp Trp Leu Asn Gly Lys
305                 310             315                     320

Glu Tyr Lys Cys Lys Val Ser Asn Lys Ala Leu Pro Ala Pro Ile Glu
                325             330                 335

Lys Thr Ile Ser Lys Ala Lys Gly Gln Pro Arg Glu Pro Gln Val Tyr
            340             345                 350

Thr Leu Pro Pro Ser Arg Asp Glu Leu Thr Lys Asn Gln Val Ser Leu
            355             360                 365

Thr Cys Leu Val Lys Gly Phe Tyr Pro Ser Asp Ile Ala Val Glu Trp
    370             375                 380

Glu Ser Asn Gly Gln Pro Glu Asn Asn Tyr Lys Thr Thr Pro Pro Val
385             390                 395                     400

Leu Asp Ser Asp Gly Ser Phe Phe Leu Tyr Ser Lys Leu Thr Val Asp
                405             410                 415

Lys Ser Arg Trp Gln Gln Gly Asn Val Phe Ser Cys Ser Val Met His
            420             425                 430
```

```
Glu Ala Leu His Asn His Tyr Thr Gln Lys Ser Leu Ser Leu Ser Pro
            435                 440                 445
Gly Lys
    450

<210> SEQ ID NO 58
<211> LENGTH: 450
<212> TYPE: PRT
<213> ORGANISM: Artificial Sequence
<220> FEATURE:
<223> OTHER INFORMATION: E294V

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Val Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

-continued

```
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 59
<211> LENGTH: 450
<212> TYPE: PRT
<213> ORGANISM: Artificial Sequence
<220> FEATURE:
<223> OTHER INFORMATION: E294Y

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245             250             255

Ser Arg Thr Pro Glu Val Thr Cys Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Tyr Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
450
```

SITE-SPECIFIC CONJUGATION OF GLYCOSYLATED MONOCLONAL ANTIBODIES WITH TRANSGLUTAMINASE

CROSS-REFERENCE TO RELATED APPLICATIONS

This application claims the benefit of U.S. Provisional Application Ser. No. 63/027,396 filed 20 May 2020. The entire content of the aforementioned application is incorporated herein by reference in its entirety.

FIELD OF THE INVENTION

The invention relates to site-specific conjugation of glycosylated antibodies. In particular, the invention relates to engineered antibodies useful for site-specific conjugation using transglutaminase. The invention also relates to methods of site-specific conjugation of the antibodies, site-specifically conjugated antibodies, and pharmaceutical compositions and uses related to the site-specifically conjugated antibodies.

REFERENCE TO SEQUENCE LISTING SUBMITTED ELECTRONICALLY

This application contains a sequence listing, which is submitted electronically via EFS-Web as an ASCII formatted sequence listing with a file name "JBI6302USNP1_SeqListing.txt" and a creation date of Apr. 19, 2021 and having a size of 225 kb. The sequence listing submitted via EFS-Web is part of the specification and is herein incorporated by reference in its entirety.

BACKGROUND OF THE INVENTION

Site-specific conjugation—covalent attachment of molecules to a particular site on a large protein such as a monoclonal antibody (mAb)—is a technology that is increasing in importance. Therapeutic platforms that make use of site-specific conjugation, such as antibody-drug conjugates, are entering clinical development in growing numbers. As a result, novel methods to complement or replace existing approaches are of great value.

One approach to site-specific conjugation that has been described utilizes transglutaminase (TGase) enzymes. Transglutaminases are a large class of enzymes with representatives in microbes as well as higher organisms (Savoca et al., 2018, *Micromachines* (Basel) 9(11)). These enzymes catalyze covalent bond formation between the ε-amino group of lysine and the γ-carboxamide group of glutamine sidechains of proteins resulting in an isopeptide bond. TGases play a role in multiple biological processes including blood coagulation, extracellular matrix assembly, and spore formation. In addition to their native function, some TGases can use other amides or amines in place of the glutamine or lysine sidechain, respectively, and thereby catalyze the covalent conjugation of small molecule substrates to proteins. For example, they can join a primary amine on a drug to the side chain carboxyamide group of a protein/peptide bound glutamine residue thus forming an isopeptide bond between the drug and the protein/peptide.

The microbial TGase (MTG) from *S. mobarensis* has proven to be particularly useful for covalent conjugation of small molecules to protein sidechains. MTG was shown to catalyze the addition of polyethylene glycol (PEG) to a variety of proteins including recombinant human IL2 (Sato, 2002, *Advanced drug delivery reviews* 54(4):487-504), interferon (Spolaore et al., 2016, *Bioconjugate chemistry* 27(11):2695-2706), and human growth hormone (Mero et al., 2011, *J Control Release* 154(1):27-34) using an amine-modified PEG to conjugate to glutamine sidechains, or PEG modified with a Gln-containing dipeptide to conjugate to lysine sidechains. In each case, PEG was added selectively to just one or a small subset of Gln or Lys sidechains. However, the substrate specificity of the *S. mobaraensis* microbial TGase (MTG) is not well understood. Different studies have shown some degree of sequence selectivity for glutamine substrate (Sugimura et al., 2008, *Arch Biochem Biophys* 477(2):379-383) as well as some degree of dependence on secondary structure (Mero et al., 2011, id.; Spolaore et al., 2012, *Biochemistry* 51(43):8679-8689). Currently, empirical approaches are typically used to determine if MTG can be used for selective conjugation of a particular protein.

MTG has been used to conjugate small molecules to monoclonal antibodies site-selectively. Two different approaches have been demonstrated for conjugation of amine-containing payloads to Gln sidechains on mAbs, one using a tagging approach and the second making use of a serendipitous discovery that a particular Gln residue can be a good MTG substrate under certain conditions. A tag-based approach has also been described for conjugation of Gln-containing payloads to a lysine sidechain.

Jeger et al. demonstrated that the rate of modification of mAbs with MTG is much faster with deglycosylated antibodies than if the N-linked glycan at position 297 is intact (Jeger et al., 2010, *Angewandte Chemie* 49(51):9995-9997) and that the modification was highly specific for one Gln site on the mAb. The conjugation site was determined to be Gln295, a position in the CH2 domain that is conserved across all human IgG isotypes and is two residues away from the glycosylation site. This approach—deglycosylation followed by MTG-catalyzed conjugation to Gln295—has been used to prepare antibody-radioconjugates, antibody-drug conjugates, and other molecules. The method does not require engineering of the mAb, but it does require removal of the glycan, which results in an impact on immunological properties, as binding to Fc receptors is abrogated, and an impact on biophysical properties such as thermal stability, where a decrease in melting temperature of the CH2 domain of up to 7-8° C. can be observed.

A tag-based method for site-selective mAb conjugation with transglutaminase has also been demonstrated. Appending or inserting a "Q-tag"—a short Gln-containing peptide such as LLQG—at certain positions in the mAb was shown to allow selective conjugation at the tag without the need for deglycosylation (Strop et al., 2013, *Chem Biol* 20(2):161-167). The Q-tag approach has been used mainly at the C-termini of the mAb light and heavy chains and requires the use of an exogeneous peptide sequence. A similar approach has been described using the c-myc tag (Dennler et al., 2015, *Chembiochem* 16(5):861-867).

Site-specificity has become a key area of focus in the antibody-drug conjugate (ADC) field (Agarwal and Bertozzi, 2015, *Bioconjug Chem* 26(2):176-92), as it has been demonstrated that both efficacy and safety of ADCs can be increased with site-specific methods as compared to random conjugation.

There remains a need in the art for efficient methods of site-specific conjugation of antibodies.

BRIEF SUMMARY OF THE INVENTION

The invention satisfies this need by providing engineered antibodies that can be site-specifically conjugated to amine-containing payloads using transglutaminase without the need for deglycosylation.

An engineered antibody of the invention can comprise an endogenous heavy chain Q295 that can be used for transglutaminase-catalyzed conjugation without removing the antibody glycan, when at least one amino acid substitution is present. An engineered antibody of the invention can comprise an amino acid substitution at a heavy chain residue that can be used for transglutaminase-catalyzed conjugation without removing the antibody glycan, when at least one further amino acid substitution is present.

In one general aspect, the invention relates to an engineered antibody comprising an amino acid substitution at heavy chain position 302 in the heavy chain constant region CH2 of the antibody. Such substitution can be, for example, V302S, V302A, V302I, V302L, V302M, V302T, V302F, and V302Y, preferably the amino acid substitutions V302A and V302S, wherein the amino acid numbering is according to the EU Index of Kabat. In a particular embodiment, the amino acid substitution at position 302 is V302A. In another embodiment, the amino acid substitution at position 302 is V302S. Preferably, the engineered antibody also contains an amino acid substitution at position 300, in the heavy chain constant region CH2 of the antibody. In a particular embodiment, the amino acid substitution at position 300 is Y300L.

In some embodiments, an engineered antibody of the invention further comprises a glutamine substitution at heavy chain position 286, 287, 288, 289, 290, 293 or 294, such as the amino acid substitution N286Q, A287Q, K288Q, T289Q, K290Q, E293Q or E294Q, and/or an alanine substitution at heavy chain position 241, 243, 294 or 301, such as F241A, F243A, E294A or R301A.

In some embodiments, the engineered antibody comprises a glutamine substitution at heavy chain position 288, such as the amino acid substitution K288Q. In some embodiments, the engineered antibody comprises a glutamine substitution at heavy chain position 293, such as the amino acid substitution E293Q. In particular embodiments, the engineered antibody comprises a glutamine substitution at heavy chain position 294, such as the amino acid substitution E294Q. In some embodiments, the engineered antibody comprises an alanine at heavy chain position 241, such as the amino acid substitution F241A. In some embodiments, the engineered antibody comprises an alanine at heavy chain position 243, such as the amino acid substitution F243A. In some embodiments, the engineered antibody comprises an alanine at heavy chain position 301, such as the amino acid substitution R301A. In particular embodiments, the engineered antibody comprises an alanine at heavy chain position 294, such as the amino acid substitution E294A. In particular embodiments, the engineered antibody comprises a glutamine substitution at heavy chain position 288, such as the amino acid substitution K288Q, and an alanine at heavy chain position 294, such as the amino acid substitution E294A.

An engineered antibody of the invention can comprise an endogenous heavy chain Q295 and a glutamine at residue 286, 287, 288, 289, 290, 293 or 294 that can be used for transglutaminase-catalyzed conjugation without removing the antibody glycan, when at least one amino acid substitution is present. In a particular embodiment, the engineered antibody of the invention comprises an endogenous heavy chain Q295 and a glutamine at residue 293. In a particular embodiment, the engineered antibody of the invention comprises an endogenous heavy chain Q295 and a glutamine at residue 294.

In one embodiment, the engineered antibody comprises the amino acid substitution V302A or V302S, optionally Y300L, and further comprises a glutamine substitution at heavy chain position 286, 287, 288, 289, 290, 293 or 294, preferably the amino acid substitution N286Q, A287Q, K288Q, T289Q, K290Q, E293Q or E294Q, wherein the amino acid numbering is according to the EU Index of Kabat. In some embodiments, the engineered antibody comprises an amino acid substitution at heavy chain position 302, such as the amino acid substitution V302A or V302S, and an amino acid substitution at heavy chain position 293, such as the amino acid substitution E293Q, optionally further comprising an amino acid substitution at heavy chain position 300, such as the amino acid substitution Y300L. In some embodiments, the engineered antibody comprises an amino acid substitution at heavy chain position 302, such as the amino acid substitution V302A or V302S, and an amino acid substitution at heavy chain position 294, such as the amino acid substitution E294Q, optionally further comprising an amino acid substitution at heavy chain position 300, such as the amino acid substitution Y300L. In particular embodiments, the engineered antibody comprises amino acid substitutions V302A and E293Q, optionally further comprising Y300L. In particular embodiments, the engineered antibody comprises amino acid substitutions V302S and E293Q, optionally further comprising Y300L. In particular embodiments, the engineered antibody comprises amino acid substitutions V302A and E294Q, optionally further comprising Y300L. In particular embodiments, the engineered antibody comprises amino acid substitutions V302A and E294Q, optionally further comprising Y300L.

In another general aspect, an engineered antibody of the invention comprises an amino acid substitution at heavy chain position 294 of the antibody. In some embodiments, the amino acid substitution is an alanine substitution. In some embodiments, the amino acid substitution is E294A or E294Q, wherein the amino acid numbering is according to the EU Index of Kabat. In some embodiments, the amino acid substitution at heavy chain position 294 of the antibody is a methionine substitution, a phenylalanine substitution, a lysine substitution, a leucine substitution, an arginine substitution, a valine substitution or a tyrosine substitution. In some embodiments, the amino acid substitution is E294A. In some embodiments, the amino acid substitution is E294F. In some embodiments, the amino acid substitution is E294K. In some embodiments, the amino acid substitution is E294L. In some embodiments, the amino acid substitution is E294R. In some embodiments, the amino acid substitution is E294V. In some embodiments, the amino acid substitution is E294Y. In a particular embodiment, the amino acid substitution is E294M.

In some embodiments, the engineered antibody further comprises an amino acid substitution at heavy chain position 302, preferably the amino acid substitution is selected from the group consisting of V302S, V302A, V302I, V302L, V302M, V302T, V302F, and V302Y, more preferably, V302A or V302S. More preferably, the engineered antibody further comprises an amino acid substitution at heavy chain position 300, preferably a leucine substitution, such as the amino acid substitution Y300L.

In certain embodiments, an engineered antibody comprises the amino acid substitution V302A or V302S and at least one of the amino acid substitutions E293Q and E294Q, wherein the amino acid numbering is according to the EU Index of Kabat. The engineered antibody can further comprise the amino acid substitution Y300L.

In another general aspect, an engineered antibody of the invention comprises amino acid substitutions at heavy chain positions 294 and 295, wherein the amino acid numbering is according to the EU Index of Kabat. In particular embodiments, the amino acid substitution at heavy chain position 294 is a glutamine substitution, such as the amino acid substitution E294Q. In some embodiments, the amino acid substitution at heavy chain position 295 is an alanine substitution, such as the amino acid substitution Q295A. In some embodiments, the amino acid substitution at heavy chain position 295 is a glutamate substitution, such as the amino acid substitution Q295E. In some embodiments, the amino acid substitution at heavy chain position 295 is an asparagine substitution, such as the amino acid substitution Q295N. In particular embodiments, the engineered antibody comprises the amino acid substitutions E294Q and Q295A. In particular embodiments, the engineered antibody comprises the amino acid substitutions E294Q and Q295E. In particular embodiments, the engineered antibody comprises the amino acid substitutions E294Q and Q295N.

The engineered antibodies disclosed herein provide improved efficiency of site-specific conjugation of amine-containing payloads using transglutaminase compared to WT mAbs, without the need for deglycosylation. In some embodiments, the engineered antibodies display an increased degree of labeling (DOL) with an amine-containing payload within a particular timeframe compared to WT mAbs, without the need for deglycosylation. In particular embodiments, the engineered antibodies display an increased degree of labelling (DOL) with an amine-containing payload within a particular timeframe compared to deglycosylated WT mAbs, without the need for deglycosylation. In particular embodiments, the engineered antibodies disclosed herein achieve complete labelling (e.g. DAR=2 or DAR=4) in a shorter timeframe compared to WT mAbs, without the need for deglycosylation. In some embodiments, the engineered antibodies have a similar or higher $T_m$ (corresponding to melting of the CH2 domain) compared to WT mAbs. In particular embodiments, the engineered antibodies can be used to generate an antibody-payload conjugate displaying equivalent or improved activity in a cell killing assay compared to WT mAbs. The substitutions described herein are also particularly useful because they can be used in a range of antibody backgrounds, for example human, humanized and chimeric IgG of different isotypes, in particular IgG1, IgG2 and IgG4. Furthermore, the substitutions described herein can be used with a range of amine-containing substrates.

In certain embodiments, an engineered antibody of the invention is a human IgG antibody, preferably a human IgG1 antibody. In some embodiments, the engineered antibody of the invention is a humanized antibody. In some embodiments, the engineered antibody of the invention is a chimeric antibody, for example a mouse-human chimeric antibody. In particular embodiments, the engineered antibody is a chimeric IgG1 antibody. In some embodiments, the engineered antibody of the invention is a human IgG2 antibody. In some embodiments, the engineered antibody of the invention is a human IgG4 antibody.

In another embodiment, an engineered antibody of the invention is glycosylated, containing the antibody glycan. Accordingly, the engineered antibodies disclosed herein can enable retention of WT binding to Fc receptors and WT biophysical properties, for example thermal stability, while enabling improved manufacturing efficiency of amine-containing antibody-payload conjugates (e.g. to DAR=2 or DAR=4) and/or increased ratio of payload to antibody in an ADC (e.g. to DAR=4).

An engineered antibody of the invention can comprise at least one amino acid substitution that enables the antibody to be conjugated to an amine-containing payload by a transglutaminase at the endogenous heavy chain Q295 residue of the antibody in the presence of the antibody glycan, wherein the amino acid numbering is according to the EU Index of Kabat. Preferably, the at least one amino acid substitution is at a glycan-interacting site, such that the endogenous Q295 residue can be used for transglutaminase-catalyzed conjugation without removing the antibody glycan.

An engineered antibody of the invention can comprise at least one amino acid substitution that enables the antibody to be conjugated to an amine-containing payload by a transglutaminase at a glutamine residue at heavy chain position 294 of the antibody in the presence of the antibody glycan, wherein the amino acid numbering is according to the EU Index of Kabat.

The invention also relates to an antibody-payload conjugate, comprising the engineered antibody of the invention conjugated to a payload. Preferably, the payload comprises one or more selected from the group consisting of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, and a first click reaction partner. In particular embodiments, the payload is an amine-containing payload. In some embodiments, the payload is conjugated to the engineered antibody at the endogenous heavy chain Q295 residue of the antibody. In other embodiments, the payload is conjugated to the engineered antibody at the glutamine residue at heavy chain position 286, 287, 288, 289, 290, 293 or 294 of the engineered antibody. In particular embodiments, the payload is conjugated to the engineered antibody at the glutamine residue at heavy chain position 293 of the engineered antibody. In particular embodiments, the payload is conjugated to the engineered antibody at the glutamine residue at heavy chain position 294 of the engineered antibody. Any suitable payload can be conjugated to the engineered antibody. In certain embodiments, the payload is conjugated to the engineered antibody at Q295 and at least one of the glutamine residues at heavy chain positions 293 and 294. Accordingly, in particular embodiments, the payload is conjugated to the engineered antibody at Q295 and the glutamine residue at heavy chain position 293. In particular embodiments, the payload is conjugated to the engineered antibody at Q295 and the glutamine residue at heavy chain position 294. Preferably, an antibody-payload conjugate of the invention has a drug antibody ratio (DAR) of 1 to 4, preferably 2-4, most preferably 2 or 4.

In another general aspect, the invention relates to a method of generating an antibody-payload conjugate, the method comprising:
  a. providing an engineered antibody of the invention;
  b. providing an amine-containing payload; and
  c. contacting the engineered antibody and the amine-containing payload with a transglutaminase under a condition to generate an antibody-payload conjugate comprising the engineered antibody conjugated to the payload at the engineered glutamine (Q) residue at heavy chain position 286, 287, 288, 289, 290, 293 or 294, and/or at the endogenous heavy chain Q295.

In some embodiments, the method of generating an antibody-payload conjugate is carried out without removing the antibody glycan of the engineered antibody.

In another general aspect, the invention relates to a pharmaceutical composition comprising an engineered antibody of the invention, or an antibody-payload conjugate of the invention, and a pharmaceutically acceptable carrier.

In another general aspect, the invention relates to a combination or kit comprising:
 a. an engineered antibody of the invention; and
 b. transglutaminase;
wherein the combination or kit is to be used for labeling the antibody with an amine-containing payload.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings.

DETAILED DESCRIPTION OF THE INVENTION

Figure 1A:
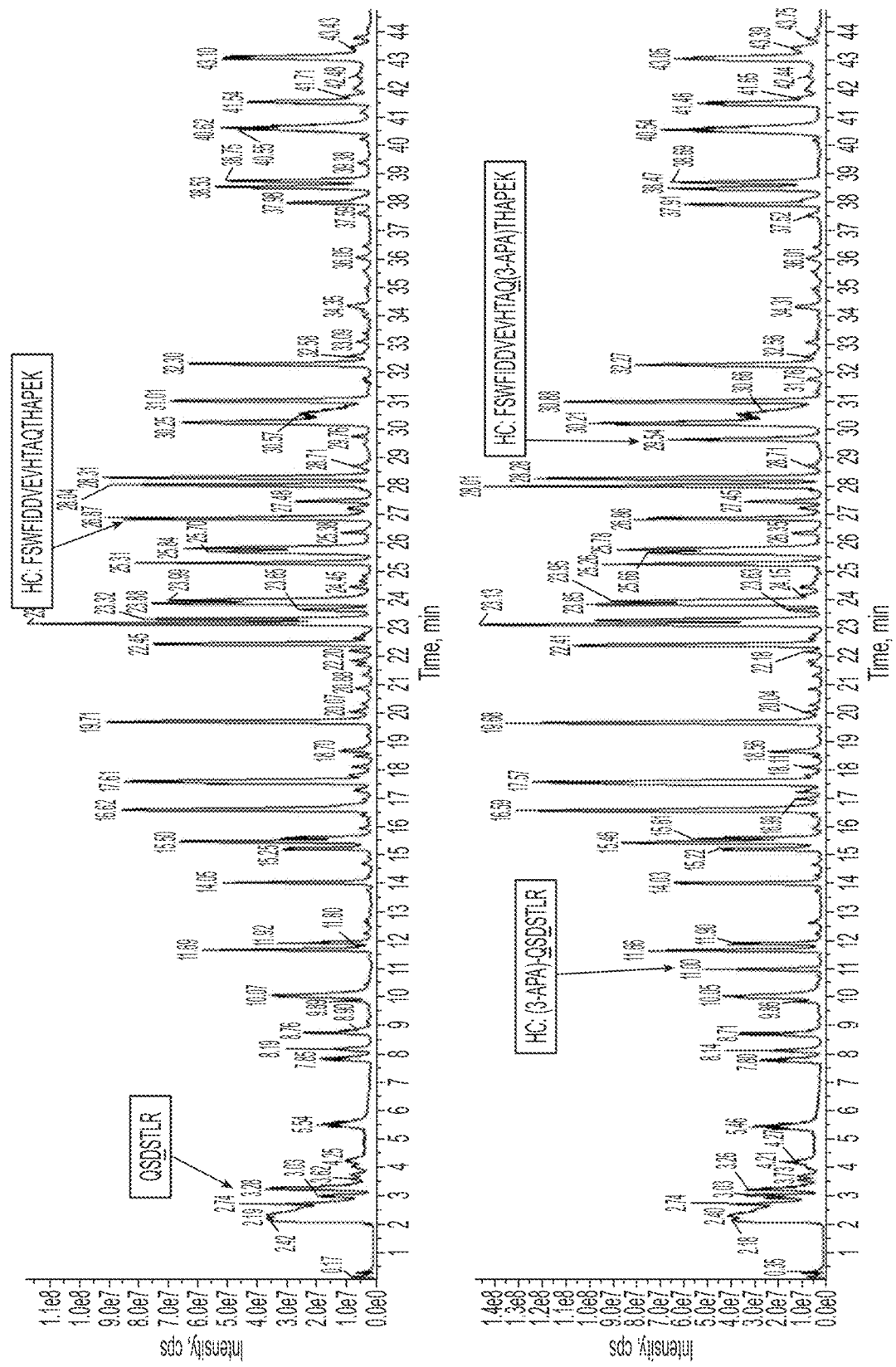
FIG. 1a shows the peptide mapping of NLDC-145 mAb (top) vs. NLDC-145 modified with 3-APA (bottom); the modified peptides containing Gln295 and Gln288 with the addition of 3-APA were identified in the transglutaminase-reacted sample as indicated by the arrow.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms cited herein have the meanings as set in the specification. All patents, published patent applications and publications cited herein are incorporated by reference as if set forth fully herein It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second.

A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

In an attempt to help the reader of the application, the description has been separated into various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

Engineered Antibodies

In contrast to known procedures, engineered antibodies of the present invention allow for site-specific conjugation of the antibodies with an amine-containing payload using transglutaminase without the need for deglycosylation to remove the antibody glycan.

In one general aspect, the invention relates to an engineered antibody, or a fragment thereof, wherein the antibody comprises a glutamine site useful for conjugation by a transglutaminase without removing the antibody glycan.

As used herein, the term "antibody" or "immunoglobulin" is used in a broad sense and includes immunoglobulin or antibody molecules including polyclonal antibodies, monoclonal antibodies including murine, human, human-adapted, humanized and chimeric monoclonal antibodies, and antigen-binding fragments thereof.

In general, antibodies are proteins or peptide chains that exhibit binding specificity to a specific antigen, referred to herein as a "target". Antibody structures are well known. An intact "antibody" comprises at least two heavy (H) chains and two light (L) chains inter-connected by disulfide bonds. See generally, Fundamental Immunology, Ch. 7 (Paul, W., ed., 2nd ed. Raven Press, N.Y. (1989)) (incorporated by reference in its entirety for all purposes). Each heavy chain is comprised of a heavy chain variable region (HCVR or VH) and a heavy chain constant region (CH). The heavy chain constant region is comprised of three domains, CHL CH2 and CH3. Each light chain is comprised of a light chain variable region (LCVR or VL) and a light chain constant region. The light chain constant region is comprised of one domain, CL. In humans, there are two types of light chains, kappa (κ) and lambda (λ), such that the constant regions of these two types of light chains are designated as Cκ and Cλ, respectively. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The assignment of amino acids to each domain is in accordance with the definitions of Kabat, Sequences of Proteins of Immunological Interest (National Institutes of Health, Bethesda, Md. (1987 and 1991)), or Chothia & Lesk, J. Mol. Biol. 196:901-917 (1987); Chothia et al., Nature 342:878-883 (1989).

As used herein, the term "engineered antibody" refers to an antibody, or a fragment thereof, comprising at least one engineered constant region, e.g., an engineered Fc region, an engineered Cκ region and/or an engineered Cλ region.

Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of any vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from mouse antibodies or human antibodies. Each of the four IgG subclasses has different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. An antibody useful for the invention can have no or minimal effector function, but retain its ability to bind FcRn.

As used herein, the phrase "useful for conjugation by a transglutaminase" refers to a glutamine residue that is reactive to an amine donor agent in the presence of a transglutaminase, wherein the glutamine residue is introduced by the antibody engineering and/or is an endogenous glutamine made reactive by the antibody engineering.

As used herein, the term "antibody glycan" refers to the N-linked glycan at position 297 within the Fc region of an antibody heavy chain, wherein the amino acid numbering is according to the EU Index of Kabat.

In a general aspect, the invention relates to an engineered antibody comprising an amino acid substitution at a heavy chain position of the antibody such that the engineered antibody can be site-specifically conjugated to amine-containing payloads using transglutaminase without the need for deglycosylation.

According to one aspect, the invention relates to an engineered antibody comprising an amino acid substitution at heavy chain position 302 in the heavy chain constant region CH2 of the antibody, wherein the amino acid numbering is according to the EU Index of Kabat.

According to one aspect, the invention relates to an engineered antibody comprising an amino acid substitution at heavy chain position 294, wherein the amino acid numbering is according to the EU Index of Kabat.

According to one aspect, the invention relates to an engineered antibody comprising an amino acid substitution at a heavy chain residue that can be used for transglutaminase-catalyzed conjugation without removing the antibody glycan, when at least one further amino acid substitution is present.

According to particular embodiments, the amino acid substitutions can be substitutions of the amino acid residue with any of the twenty naturally occurring (or 'standard' amino acids) or variants thereof, or any variants that are not naturally found in proteins.

The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 1 shows the abbreviations and properties of the standard amino acids.

TABLE 1

Standard amino acids, abbreviations and properties

| Amino Acid | 3-Letter | 1-Letter | Side chain polarity | Side chain charge (pH 7.4) |
|---|---|---|---|---|
| Alanine | Ala | A | Nonpolar | neutral |
| arginine | Arg | R | Polar | positive |
| asparagine | Asn | N | Polar | neutral |
| aspartic acid | Asp | D | Polar | negative |
| cysteine | Cys | C | Nonpolar | neutral |
| glutamic acid | Glu | E | Polar | negative |
| glutamine | Gln | Q | Polar | neutral |
| glycine | Gly | G | Nonpolar | neutral |
| histidine | His | H | Polar | positive (10%) neutral(90%) |
| isoleucine | Ile | I | Nonpolar | neutral |
| leucine | Leu | L | Nonpolar | neutral |
| Lysine | Lys | K | Polar | positive |
| methionine | Met | M | Nonpolar | neutral |
| phenylalanine | Phe | F | Nonpolar | neutral |
| proline | Pro | P | Nonpolar | neutral |
| Serine | Ser | S | Polar | neutral |
| threonine | Thr | T | Polar | neutral |
| tryptophan | Trp | W | Nonpolar | neutral |
| tyrosine | Tyr | Y | Polar | neutral |
| Valine | Val | V | Nonpolar | neutral |

According to particular embodiments, the engineered antibody comprises an amino acid substitution at heavy chain position 302, wherein the amino acid numbering is according to the EU Index of Kabat. According to particular embodiments, the engineered antibody comprises an amino acid substitution selected from the group consisting of V302S, V302A, V302I, V302L, V302M, V302T, V302F, and V302Y. According to particular embodiments, a valine at residue 302 is substituted with serine (V302S). In another particular embodiment, a valine at residue 302 is substituted with alanine (V302A).

According to particular embodiments, the engineered antibody further comprises an amino acid substitution at heavy chain position 300. According to particular embodiments, a tyrosine at residue 300 is substituted with leucine (Y300L).

In some embodiments, the engineered antibody contains an amino acid substitution at heavy chain position 300 and an amino acid substitution at heavy chain position 302. In some embodiments, the amino acid substitution at heavy chain position 300 is Y300L and the amino acid substitution at heavy chain position 302 is V302A. In a particular embodiment, the amino acid substitution at heavy chain position 300 is Y300L and the amino acid substitution at heavy chain position 302 is V302S.

According to particular embodiments, the engineered antibody further comprises an amino acid substitution at heavy chain position 294. According to particular embodiments, a glutamic acid at residue 294 is substituted with alanine (E294A).

According to particular embodiments, the engineered antibody further comprises an amino acid substitution at heavy chain position 286, 287, 288, 289, 290, 293 or 294. According to particular embodiments, an asparagine at residue 286 is substituted with glutamine (N286Q), an alanine at residue 287 is substituted with glutamine (A287Q), a lysine at residue 288 is substituted with glutamine (K288Q), a threonine at residue 289 is substituted with glutamine (T289Q), a lysine at residue 290 is substituted with glutamine (K290Q), a glutamic acid at residue 293 is substituted with glutamine (E293Q), or a glutamic acid at residue 294 is substituted with glutamine (E294Q).

In some embodiments, the engineered antibody comprises an amino acid substitution at heavy chain position 302, such as the amino acid substitution V302A or V302S, and an amino acid substitution at heavy chain position 285, such as the amino acid substitution H285Q, optionally further comprising an amino acid substitution at heavy chain position 300, such as the amino acid substitution Y300L. In some embodiments, the engineered antibody comprises amino acid substitutions at heavy chain positions 302 and 285. In some embodiments, the engineered antibody comprises amino acid substitutions V302A and H285Q. In some embodiments, the engineered antibody comprises amino acid substitutions V302S and H285Q. In some embodiments, the engineered antibody comprises amino acid substitutions at heavy chain positions 302, 285 and 300. In some embodiments, the engineered antibody comprises amino acid substitutions V302A, H285Q and Y300L. In some embodiments, the engineered antibody comprises amino acid substitutions V302S, H285Q and Y300L.

In some embodiments, the engineered antibody comprises an amino acid substitution at heavy chain position 302, such as the amino acid substitution V302A or V302S, and an amino acid substitution at heavy chain position 286, such as the amino acid substitution N286Q, optionally further comprising an amino acid substitution at heavy chain position 300, such as the amino acid substitution Y300L. In some embodiments, the engineered antibody comprises amino acid substitutions at heavy chain positions 302 and 286. In some embodiments, the engineered antibody comprises amino acid substitutions V302A and N286Q. In some embodiments, the engineered antibody comprises amino acid substitutions V302S and N286Q. In some embodiments, the engineered antibody comprises amino acid substitutions at heavy chain positions 302, 286 and 300. In some embodiments, the engineered antibody comprises amino acid substitutions V302A, N286Q and Y300L. In some embodiments, the engineered antibody comprises amino acid substitutions V302S, N286Q and Y300L.

In some embodiments, the engineered antibody comprises an amino acid substitution at heavy chain position 302, such as the amino acid substitution V302A or V302S, and an amino acid substitution at heavy chain position 287, such as the amino acid substitution A287Q, optionally further comprising an amino acid substitution at heavy chain position 300, such as the amino acid substitution Y300L. In some embodiments, the engineered antibody comprises amino acid substitutions at heavy chain positions 302 and 287. In some embodiments, the engineered antibody comprises amino acid substitutions V302A and A287Q. In some embodiments, the engineered antibody comprises amino acid substitutions V302S and A287Q. In some embodiments, the engineered antibody comprises amino acid substitutions at heavy chain positions 302, 287 and 300. In some embodiments, the engineered antibody comprises amino acid substitutions V302A, A287Q and Y300L. In some embodiments, the engineered antibody comprises amino acid substitutions V302S, A287Q and Y300L.

In some embodiments, the engineered antibody comprises an amino acid substitution at heavy chain position 302, such as the amino acid substitution V302A or V302S, and an amino acid substitution at heavy chain position 288, such as the amino acid substitution K288Q, optionally further comprising an amino acid substitution at heavy chain position 300, such as the amino acid substitution Y300L. In some embodiments, the engineered antibody comprises amino acid substitutions at heavy chain positions 302 and 288. In some embodiments, the engineered antibody comprises amino acid substitutions V302A and K288Q. In some embodiments, the engineered antibody comprises amino acid substitutions V302S and K288Q. In some embodiments, the engineered antibody comprises amino acid substitutions at heavy chain positions 302, 288 and 300. In a particular embodiment, the engineered antibody comprises amino acid substitutions V302A, K288Q and Y300L. In a particular embodiment, the engineered antibody comprises amino acid substitutions V302S, K288Q and Y300L.

In some embodiments, the engineered antibody comprises an amino acid substitution at heavy chain position 302, such as the amino acid substitution V302A or V302S, and an amino acid substitution at heavy chain position 289, such as the amino acid substitution T289Q, optionally further comprising an amino acid substitution at heavy chain position 300, such as the amino acid substitution Y300L. In some embodiments, the engineered antibody comprises amino acid substitutions at heavy chain positions 302 and 289. In some embodiments, the engineered antibody comprises amino acid substitutions V302A and T289Q. In some embodiments, the engineered antibody comprises amino acid substitutions V302S and T289Q. In some embodiments, the engineered antibody comprises amino acid substitutions at heavy chain positions 302, 289 and 300. In some embodiments, the engineered antibody comprises amino acid substitutions V302A, T289Q and Y300L. In some embodiments, the engineered antibody comprises amino acid substitutions V302S, T289Q and Y300L.

In some embodiments, the engineered antibody comprises an amino acid substitution at heavy chain position 302, such as the amino acid substitution V302A or V302S, and an amino acid substitution at heavy chain position 290, such as the amino acid substitution K290Q, optionally further comprising an amino acid substitution at heavy chain position 300, such as the amino acid substitution Y300L. In some embodiments, the engineered antibody comprises amino acid substitutions at heavy chain positions 302 and 290. In some embodiments, the engineered antibody comprises amino acid substitutions V302A and K290Q. In some embodiments, the engineered antibody comprises amino acid substitutions V302S and K290Q. In some embodiments, the engineered antibody comprises amino acid substitutions at heavy chain positions 302, 290 and 300. In some embodiments, the engineered antibody comprises amino acid substitutions V302A, K290Q and Y300L. In some embodiments, the engineered antibody comprises amino acid substitutions V302S, K290Q and Y300L.

In some embodiments, the engineered antibody comprises an amino acid substitution at heavy chain position 302, such as the amino acid substitution V302A or V302S, and an amino acid substitution at heavy chain position 293, such as the amino acid substitution E293Q, optionally further comprising an amino acid substitution at heavy chain position 300, such as the amino acid substitution Y300L. In some embodiments, the engineered antibody comprises amino acid substitutions at heavy chain positions 302 and 293. In some embodiments, the engineered antibody comprises amino acid substitutions V302A and E293Q. In some embodiments, the engineered antibody comprises amino acid substitutions V302S and E293Q. In some embodiments, the engineered antibody comprises amino acid substitutions at heavy chain positions 302, 293 and 300. In particular embodiments, the engineered antibody comprises amino acid substitutions V302A, E293Q and Y300L. In particular embodiments, the engineered antibody comprises amino acid substitutions V302S, E293Q and Y300L.

In some embodiments, the engineered antibody comprises an amino acid substitution at heavy chain position 302, such as the amino acid substitution V302A or V302S, and an amino acid substitution at heavy chain position 294, such as the amino acid substitution E294Q, optionally further comprising an amino acid substitution at heavy chain position 300, such as the amino acid substitution Y300L. In some embodiments, the engineered antibody comprises amino acid substitutions at heavy chain positions 302 and 294. In particular embodiments, the engineered antibody comprises amino acid substitutions V302A and E294Q. In particular embodiments, the engineered antibody comprises amino acid substitutions V302S and E294Q. In some embodiments, the engineered antibody comprises amino acid substitutions at heavy chain positions 302, 294 and 300. In particular embodiments, the engineered antibody comprises amino acid substitutions V302A, E294Q and Y300L. In particular embodiments, the engineered antibody comprises amino acid substitutions V302S, E294Q and Y300L.

In some embodiments, the engineered antibody provides an antibody-payload conjugate, with an intact glycan, having a DAR of 2. In particular embodiments, the engineered antibody provides an antibody-payload conjugate, with an intact glycan, having a DAR of 4. In some embodiments, the engineered antibody, with an intact glycan, displays complete labeling (e.g. DAR=2 or DAR=4) with an amine-containing payload, using transglutaminase, on a shorter timescale than a WT mAb. In some embodiments, the engineered antibody, with an intact glycan, displays an increased DOL compared to a WT mAb within 0.5 hours, 1 hours, 1.5 hours, 2 hours, 2.5 hours, 3 hours, 3.5 hours, 4 hours, 4.5 hours or 5 hours of an amine-containing payload conjugation assay. In particular embodiments, the engineered antibody, with an intact glycan, displays an increased DOL compared to a deglycosylated WT mAb within 0.5 hours, 1 hours, 1.5 hours, 2 hours, 2.5 hours, 3 hours, 3.5 hours, 4 hours, 4.5 hours or 5 hours of an amine-containing payload conjugation assay.

According to another aspect, the invention relates to an engineered antibody, or a fragment thereof, wherein the antibody comprises at least one amino acid substitution at a glycan-interacting site.

According to particular embodiments, the amino acid substitutions can be substitutions of the amino acid residue with any of the twenty naturally occurring (or 'standard' amino acids) or variants thereof, or any variants that are not naturally found in proteins.

According to particular embodiments, the amino acid substitution is at heavy chain position 301, 241 or 243. According to particular embodiments, an arginine at residue 301 is substituted with alanine (R301A). According to particular embodiments, a phenylalanine at residue 241 is substituted with alanine (F241A). According to particular embodiments, a phenylalanine at residue 243 is substituted with alanine (F243A).

According to particular embodiments, an engineered antibody of the invention comprises an amino acid substitution at heavy chain position 294 of the antibody wherein the amino acid numbering is according to the EU Index of Kabat.

In some embodiments, the amino acid substitution at heavy chain position 294 of the antibody is an alanine substitution, a methionine substitution, a phenylalanine substitution, a lysine substitution, a leucine substitution, an arginine substitution, a valine substitution or a tyrosine substitution. In some embodiments, the amino acid substitution is E294A. In some embodiments, the amino acid substitution is E294F. In some embodiments, the amino acid substitution is E294K. In some embodiments, the amino acid substitution is E294L. In some embodiments, the amino acid substitution is E294R. In some embodiments, the amino acid substitution is E294V. In some embodiments, the amino acid substitution is E294Y. In a particular embodiment, the amino acid substitution is E294M.

In particular embodiments, the engineered antibody comprises an alanine at heavy chain position 294, such as the amino acid substitution E294A and a glutamine substitution at heavy chain position 288, such as the amino acid substitution K288Q.

In some embodiments, the substitution at 294, either alone or in combination with an additional substitution (e.g. K288Q), provides an engineered antibody, with an intact glycan, displaying an increased degree of labeling (DOL) in an amine-containing payload conjugation assay within a particular timeframe compared to a WT mAb. In particular embodiments, the engineered antibody is equally effective in a cell cytotoxicity assay compared to a WT mAb.

In some embodiments, the substitution at 294 provides an engineered antibody, with thermal stability equivalent to or improved compared to a WT mAb. In particular embodiments, the engineered antibody displays an equivalent or improved $T_m$ compared to a WT mAb. In some embodiments, the $T_m$ of the engineered antibody is at least about 0.5° C., 1° C., 1.5° C., 2° C., 2.5° C., 3° C., 3.5° C., 4° C., 4.5° C. or 5° C. more than the WT mAb.

In particular embodiments, the substitution at 294, for example E294M, provides an engineered antibody, with an intact glycan, displaying an increased degree of labeling (DOL) in an amine-containing payload conjugation assay within a particular timeframe compared to a WT mAb and an equivalent or improved $T_m$ compared to a WT mAb.

In some embodiments, an engineered antibody of the invention comprises an amino acid substitution at heavy chain position 293 of the antibody wherein the amino acid numbering is according to the EU Index of Kabat. In some embodiments, the amino acid substitution at heavy chain position 293 of the antibody is an alanine substitution, a methionine substitution, a phenylalanine substitution, a lysine substitution, a leucine substitution, an arginine substitution, a valine substitution or a tyrosine substitution. In particular embodiments, the amino acid substitution is E293M.

An engineered antibody of the invention may comprise an amino acid substitution at heavy chain position 295 of the antibody, wherein the amino acid numbering is according to the EU Index of Kabat. In some embodiments, an engineered antibody of the invention comprises amino acid substitutions at heavy chain positions 294 and 295. In particular embodiments, the amino acid substitution at heavy chain position 294 is a glutamine substitution, such as the amino acid substitution E294Q. In some embodiments, the amino acid substitution at heavy chain position 295 is an alanine substitution, such as the amino acid substitution Q295A. In some embodiments, the amino acid substitution at heavy chain position 295 is a glutamate substitution, such as the amino acid substitution Q295E. In some embodiments, the amino acid substitution at heavy chain position 295 is an asparagine substitution, such as the amino acid substitution Q295N. In particular embodiments, the engineered antibody comprises the amino acid substitutions E294Q and Q295A. In particular embodiments, the engineered antibody comprises the amino acid substitutions E294Q and Q295E. In particular embodiments, the engineered antibody comprises the amino acid substitutions E294Q and Q295N.

In some embodiments, the substitution at 295 in combination with a substitution at 294, provides an engineered antibody, with an intact glycan, displaying an increased degree of labeling (DOL) in an amine-containing payload conjugation assay within a particular timeframe compared to a WT mAb. In some embodiments, the substitution at 295 in combination with a substitution at 294, provides an engineered antibody, with an intact glycan, displaying an increased degree of labeling (DOL) in an amine-containing payload conjugation assay within a particular timeframe compared to a deglycosylated WT mAb.

In some embodiments, the engineered antibodies disclosed herein, with an intact glycan, display an increased degree of labeling (DOL) in an amine-containing payload conjugation assay within a particular timeframe compared to a WT mAb or a deglycosylated WT mAb, for example within 0.5 hours, 1 hours, 1.5 hours, 2 hours, 2.5 hours, 3 hours, 3.5 hours, 4 hours, 4.5 hours or 5 hours (e.g. 0.5 hours) of an amine-containing payload conjugation assay. In some embodiments, the DOL is determined after a particular incubation period of the engineered antibody with transglutaminase (e.g. MTG) and an amine payload conjugate (e.g. 3-azido propylamine (3-APA)) at 22-37° C. In some embodiments, the DOL is determined using mass spectrometry (MS), such as liquid chromatography MS (LC-MS), for example on an Agilent G6224 MS-TOF Mass Spectrometer. In some embodiments, the engineered antibodies disclosed herein, display an equivalent or improved $T_m$ compared to a WT mAb. In some embodiments, the $T_m$ of the engineered antibody is at least about 0.5° C., 1° C., 1.5° C., 2° C., 2.5° C., 3° C., 3.5° C., 4° C., 4.5° C. or 5° C. more than the WT mAb. In some embodiments, $T_m$ can be determined by monitoring changes in fluorescence intensity at 330 and 350 nm upon thermal scanning from 20 to 95° C. In particular embodiments, the engineered antibodies disclosed herein display an increased degree of labeling (DOL) in an amine-containing payload conjugation assay within a particular timeframe compared to a deglycosylated WT mAb, without requiring deglycosylation, and display an equivalent or improved $T_m$ compared to a WT mAb.

In some embodiments, the engineered antibody of the invention is effective in a cell cytotoxicity assay. In particular embodiments, the engineered antibody is equally effective in a cell cytotoxicity assay compared to a WT mAb. In particular embodiments, the cell cytotoxicity assay requires treatment of a cancer cell line (e.g. SKBR3) with varying concentrations of the ADC comprising the engineered antibody of the invention, and determining cell viability (e.g. using Cell Titer Glo) at the conclusion of the treatment. In some embodiments, the treatment is for 72 hr at 37° C.

According to another aspect, the invention relates to an antibody-payload conjugate comprising an engineered antibody of the invention conjugated to a payload, optionally through a linker, at the endogenous heavy chain Q295 residue.

According to another aspect, the invention relates to an antibody-payload conjugate comprising an engineered antibody of the invention conjugated to a payload, optionally through a linker, at the endogenous heavy chain Q295 residue and at the engineered glutamine (Q) residue at heavy chain position 286, 287, 288, 289, 290, 293 or 294. In particular embodiments, the antibody-payload conjugate is conjugated to a payload, optionally through a linker, at the endogenous heavy chain Q295 residue and at the engineered glutamine (Q) residue at heavy chain position 293. In particular embodiments, the antibody-payload conjugate is conjugated to a payload, optionally through a linker, at the endogenous heavy chain Q295 residue and at the engineered glutamine (Q) residue at heavy chain position 294.

According to another aspect, the invention relates to an antibody-payload conjugate comprising an engineered antibody of the invention conjugated to a payload, optionally through a linker, at the engineered glutamine (Q) residue at heavy chain position 294 alone.

According to another aspect, the invention relates to an antibody-payload conjugate comprising an engineered antibody of the invention conjugated to one or more payloads, optionally through a linker. In a particular embodiment, the antibody-payload conjugate comprises an engineered antibody of the invention conjugated to a payload, optionally through a linker at the engineered glutamine (Q) residue at heavy chain position 294 (for example on each heavy chain of the engineered antibody) and the glutamine (Q) residue at heavy chain position 295 (for example on each heavy chain of the engineered antibody).

In particular embodiments, the engineered antibody of the invention is glycosylated, containing the antibody glycan. Accordingly, in some embodiments, the engineered antibody displays an increased degree of labeling in an amino-containing payload conjugation assay, within a particular timeframe compared to WT (intact or deglycosylated) controls, while retaining an intact glycan. In some embodiments, the engineered antibody provides an antibody-payload conjugate having a DAR of 2 while retaining an intact glycan. In some embodiments, the engineered antibody provides an antibody-payload conjugate having a DAR of 4 while retaining an intact glycan. In particular embodiments, the engineered antibody displays an increased degree of labeling in an amino-containing payload conjugation assay, within a particular timeframe compared to WT (intact or deglycosylated) controls, and provides an antibody-payload conjugate having a DAR of 4 while retaining an intact glycan. Therefore, the engineered antibody of the invention can enable more efficient manufacture of an antibody-payload conjugate and/or enable increased ratio of payload to antibody in an ADC, while retaining WT binding to Fc receptors and WT biophysical properties, for example thermal stability. In particular embodiments, the engineered antibody of the invention is equally effective in cell cytotoxicity assays compared to WT mAbs.

As used herein, the term "antibody-payload conjugate" refers to an antibody covalently linked to a molecule referred to herein as a "payload." An "antibody-drug conjugate" is an "antibody-payload conjugate" that is covalently linked to a cytotoxic or cytosolic drug/agent where the drug/agent is also referred to herein as a "payload."

Any suitable payload known to those skilled in the art in view of the present disclosure can be used in the invention. The payload can be, for example, a drug/agent, a linker, a click reaction partner, etc. According to particular embodiments, the payload can be, for example, a cytotoxic agent, a cytostatic agent, a chemotherapeutic agent, a toxin, a radionuclide, a DNA, an RNA, an siRNA, a microRNA, a peptide nucleic acid, a non-natural amino acid, a peptide, an enzyme, a fluorescent tag, a biotin, a linker, or a first click reaction partner.

As used herein, the term "covalently linked" means that the payload is attached to the antibody via at least one covalent linkage. The linkage can be direct, i.e. without a linker, or indirect, i.e. via a linker.

As used herein, the term "linker" refers to a chemical moiety that joins two molecules. Any suitable linker known to those skilled in the art in view of the present disclosure can be used in the invention. The linkers can be, for example, a single covalent bond, a substituted or unsubstituted alkyl moiety, a substituted or unsubstituted heteroalkyl moiety, a polyethylene glycol (PEG) linker, a peptide linker, a sugar-based linker, or a cleavable linker, such as a disulfide linkage or a protease cleavage site such as valine-citrulline-PAB.

According to particular aspects, the engineered antibody is conjugated to a first click reaction partner. According to particular aspects, the antibody-payload conjugate is further reacted with a second click reaction partner that comprises one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin to thereby obtain a second antibody-payload conjugate.

As used herein, the term "click chemistry" refers to a chemical philosophy introduced by Sharpless, describing chemistry tailored to generate covalent bonds quickly and reliably by joining small units comprising reactive groups together (see Kolb, et al., *Angew Chem Int Ed Engl.* 2001 Jun. 1; 40(11):2004-2021). Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force to favor a reaction with a single reaction product, and/or can be carried out under physiological conditions. In some embodiments, a click chemistry reaction exhibits high atom economy, can be carried out under simple reaction conditions, uses readily available starting materials and reagents, uses no toxic solvents or uses a solvent that is benign or easily removed, such as water, and/or provides simple product isolation by non-chromatographic methods, such as crystallization or distillation. In certain embodiments, the click chemistry reaction is a Huisgen cycloaddition or the 1,3-dipolar cycloaddition between an azide (—N3) and an alkyne, or an alkyne moiety, to form a 1,2,4-triazole linker.

As used herein, the term "click reaction partner" or "click chemistry handle" refers to a reactant or a reactive group that can partake in a click chemistry reaction. A click reaction partner can be a moiety that is rarely found in naturally-occurring biomolecules and is chemically inert towards biomolecules, but, e.g., when reacted with an azide-reactive or alkyne-reactive group, the reaction can take place efficiently under biologically relevant conditions, for example in cell culture conditions, such as in the absence of excess heat or harsh reactants. In general, click chemistry reactions require at least two molecules comprising click reaction partners that can react with each other. Such click reaction partners that are reactive with each other are sometimes referred to herein as click chemistry handle pairs, or click chemistry pairs. In some embodiments, the click reaction partners are an azide and a strained alkyne, e.g. a cyclooctyne, or any other alkyne. In other embodiments, the click reaction partners are reactive dienes and suitable tetrazine dienophiles. For example, trans-cyclooctene, norbornene, or biscyclononene can be paired with a suitable tetrazine dienophile as a click reaction pair. In yet other embodiments, tetrazoles can act as latent sources of nitrile imines, which can pair with unactivated alkenes in the presence of ultraviolet light to create a click reaction pair, termed a "photoclick" reaction pair. In other embodiments, the click reaction partners are a cysteine and a maleimide. For example, the cysteine from a peptide (e.g., GGGC) can be reacted with a maleimide that is associated with a chelating agent (e.g., NOTA). Other suitable click chemistry handles are known to those of skill in the art (see, e.g., Spicer et al., "Selective chemical protein modification." Nature Communications. 2014; 5:4740). In other embodiments, the click reaction partners are Staudinger ligation components, such as phosphine and azide. In other embodiments, the click reaction partners are Diels-Alder reaction components, such as dienes, such as tetrazine, and alkenes, such as trans-cyclooctene (TCO) or norbornene. Exemplary click reaction partners are described in US20130266512 and in WO2015073746, the relevant description on click reaction partners in both of which are incorporated by reference herein. According to preferred embodiments, one of the first and second click reaction partners comprises an alkyne group, and the other click reaction partner comprises an azide. According to other preferred embodiments, one of the first and second click reaction partners comprises an alkene group, and the other click reaction partner comprises a diene.

As used herein, the term "alkyne", "alkyne group" or "alkyne moiety" refers to a functional group comprising a carbon-carbon triple bond. Alkyne moieties include terminal alkynes and cyclic alkynes, preferably terminal alkynes and cyclic alkynes that are reactive with azide groups. A terminal alkyne has at least one hydrogen atom bonded to a triply bonded carbon atom. A cyclic alkyne is a cycloalkyl ring comprising one or more triple bonds. Examples of cyclic alkynes include, but are not limited to, cyclooctyne and cyclooctyne derivatives, such as bicyclononyne (BCN), difluorinated cyclooctyne (DIFO), dibenzocyclooctyne (DIBO), keto-DIBO, biarylazacyclooctynone (BARAC), dibenzoazacyclooctyne (DIBAC), dimethoxyazacyclooctyne (DIMAC), dibenzyocyclooctyne (DBCO), difluorobenzocyclooctyne (DIFBO), monobenzocyclooctyne (MOBO), and tetramethoxy DIBO (TMDIBO).

According to preferred embodiments, the first click reaction partner is 3-azido-1-propylamine. According to preferred embodiments, the second click reaction partner is dibenzocyclooctyne-tetraethylene glycol-valine-citrulline-paraaminobenzyl carbamate-monomethyl auristatin F (DBCO-val-cit-MMAF or DBCO-vcMMAF) or dibenzocyclooctyne-tetraethylene glycol-monomethyl auristatin F (DBCO-MMAF).

The engineered antibodies of the invention may be conjugated to a range of different substrates to form the conjugated antibody payload. In some embodiments, the substrate comprises a cleavable or non-cleavable linker. In some embodiments, the substrate is 3-Azidopropylamine. In some embodiments, the substrate is an azide-containing amine with a short PEG linker, such as the biotin-linked amine pentylaminobiotin. In some embodiments, the substrate is NH2-PEG4-MMAF. In some embodiments, the substrate is NH2-PEG4-Val-Cit-PABC-MMAF.

As used herein, the term "diene" refers to a compound having two carbon-to-carbon double bonds where these double bonds are conjugated in the 1,3-position. The double bonds of the diene can be either cis or trans. Examples of dienes include, but are not limited to, a tetrazine or a tetrazole group.

As used herein, the term "alkene", "alkene group" or "alkene moiety" refers to an unsaturated hydrocarbon molecule that includes a carbon-carbon double bond. According to particular embodiments, an alkene can include from 2 to 100 carbon atoms. Examples of alkenes include, but are not limited to, norbornene and trans-cyclooctene (TCO). According to other preferred embodiments, one of the first and second click reaction partners comprises an alkene group, preferably norbornene or TCO. According to preferred embodiments, the other click reaction partner comprises a diene, preferably a tetrazine or tetrazole group.

Conditions for carrying out click chemistry reactions are known in the art, and any conditions for carrying out click chemistry reactions known to those skilled in the art in view of the present disclosure can be used in the invention.

As used herein, the term "DAR", also called "drug-to-antibody ratio", refers to the number of payloads linked to an antibody in antibody-payload conjugate. The DAR can vary, and will be limited by the number of available sites on the antibody where the payload can be conjugated to. In some embodiments, an antibody-payload conjugate described herein has a DAR of 1-4, such as 1, 2, 3 or 4. The DAR for a population (or batch) of antibody-payload conjugates can be determined empirically using spectrophotometric measurements. The population can contain a mixture of antibody-payload conjugates that differ in drug load. Thus, the DAR for the population of antibody-payload conjugates typically represents the average DAR of the antibody-payload conjugates within the population, which can be 1, 2, 3, 4, or any value in between.

In one embodiment, an antibody-payload conjugate of the application has a DAR of 1-4, preferably 2-4, more preferably 4. More preferably, the engineered antibody in the antibody-payload conjugate is glycosylated, containing antibody glycan. Most preferably, an antibody-payload conjugate of the application comprises a glycosylated engineered antibody of the invention conjugated to a payload, and the antibody-payload conjugate has a DAR of 2-4, preferably about 4.

In another general aspect, the invention relates to a method of generating an antibody-payload conjugate, the method comprising:
  a. providing an engineered antibody of the invention;
  b. providing an amine-containing payload; and
  c. contacting the engineered antibody and the amine-containing payload with a transglutaminase under a condition to generate the antibody-payload conjugate comprising the engineered antibody conjugated to the payload at the endogenous heavy chain Q295, or at the endogenous heavy chain Q295 and at the engineered glutamine (Q) residue at heavy chain position 286, 287, 288, 289, 290, 293 or 294.

In a particular embodiment, the engineered antibody of step c. is conjugated to the payload at the endogenous heavy chain Q295 and at the engineered glutamine (Q) residue at heavy chain position 293. In another particular embodiment, the engineered antibody of step c. is conjugated to the payload at the endogenous heavy chain Q295 and at the engineered glutamine (Q) residue at heavy chain position 294.

As used herein, the term "site-specific" refers to the specific conjugation or crosslinking of the amine-containing payload to the antibody at a specific site (e.g., at the endogenous Q295 or at the N286Q, A287Q, K288Q, T289Q, K290Q, E293Q or E294Q substitution). Site specificity can be measured by various techniques, including, but not limited to, mass spectrometry (e.g., matrix-assisted laser-desorption ionization mass spectrometry (MALDI-MS), electrospray ionization mass spectrometry (ESI-MS), tandem mass spectrometry (MS-MS), and time-of-flight mass spectrometry (TOF-MS), hydrophobic interaction chromatography, ion exchange chromatography, site-directed mutagenesis, fluorescence-labeling, size exclusion chromatography, and X-ray crystallography.

As used herein, the term "amine-containing payload" refers to a payload containing one or more reactive amines (e.g., primary amines). For example, the amine-containing payload can comprise an amine donor unit (e.g., primary amine NH2), a linker (e.g., a molecule that is linked to an amine donor unit and contains additional functionality for attachment to a payload such as a small molecule, a polypeptide, or a biocompatible polymer), and an agent moiety (e.g., a payload such as a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, linker or a first click reaction partner). The amine-containing payload can also be a polypeptide (e.g., an antibody) or a biocompatible polymer containing one or more reactive lysine, N-termini, or reactive amines.

Both the endogenous Q295 and the N286Q, A287Q, K288Q, T289Q, K290Q, E293Q and E294Q substitutions described herein are substrates for transglutaminase, and the linkage between the glutamine and the amine-containing payload, is of the formula CO—NH—, wherein NH— is linked to a linker and a payload moiety.

Transglutaminases are protein-glutamine γ-glutamyl-transferases (EC 2.3.2.13), which typically catalyze pH-dependent transamidation of glutamine residues with lysine residues. As used herein, the term "transglutaminase" refers to an enzyme that catalyzes the formation of an isopeptide bond between a free amine group on a payload and the acyl group on the side chain of a glutamine residue in an antibody. Examples of transglutaminases include, but are not limited to, microbial transglutaminase (mTG), human transglutaminase, tissue transglutaminase (tTG), and Factor XIII. Examples of human transglutaminases include, but are not limited to, keratinocyte transglutaminase (Uniprot P22735), tissue transglutaminase (UniProt P21980), epidermal transglutaminase and prostate transglutaminase. These enzymes can be from either natural or recombinant sources. Glutamine and lysine amino acids in a peptide or polypeptide can be substrates for transglutaminase crosslinking. For example, the payload can be linked to a linker comprising a lysine.

The transglutaminase used in the invention described herein can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, MO) and MP Biomedicals (Irvine, CA)).

In some embodiments, the transglutaminase is derived from a fungal protein (e.g., Oomycetes, Actinomycetes, Saccharomyces, Candida, Cryptococcus, Monascus, or Rhizopus transglutaminases). In some embodiments, the transglutaminase polypeptide is derived from Myxomycetes (e.g., Physarum polycephalum transglutaminase). In some embodiments, the mTGase polypeptide is derived from a bacterial protein, such as transglutaminase from Streptoverticillium sp. or Streptomyces sp. (e.g., Streptomyces mobarensis or Streptoverticillium mobarensis). In some embodiments, the transglutaminase polypeptide is derived from a bacterial protein, such as transglutaminase from, but not limited to, Streptoverticillium mobarensis, Streptoverticillium griseocameum, Streptoverticillium ladakanum, Streptomyces mobarensis, Streptomyces viridis, Streptomyces ladakanum, Streptomyces caniferus, Streptomyces platensis, Streptomyces hygroscopius, Streptomyces netropsis, Streptomyces fradiae, Streptomyces roseovertivillatus, Streptomyces cinnamaoneous, Streptomyces griseocameum, Streptomyces lavendulae, Streptomyces lividans, Streptomyces lydicus, Streptomyces sioyansis, Actinomadura sp., Bacillus (e.g., Bacillus circulans, Bacillus subtilis, etc.), Corynebacterium ammonia genes, Corynebacterium glutamicum, Clostridium, Enterobacter sp., Micrococcus, Providencia sp., or isolates thereof. In some embodiments, the transglutaminase is a calcium independent transglutaminase which does not require calcium to induce enzyme conformational changes and allow enzyme activity. In some embodiments, the transglutaminase polypeptide is derived from S. mobarensis.

Commercially available calcium independent transglutaminase such as ACTIVA (Ajinomoto, Japan) is also suitable for the present invention.

In some embodiments, the transglutaminase used in the invention described herein can also be a recombinant protein produced using recombinant techniques known to persons skilled in the art. In some embodiments, the transglutaminase used in the invention described herein can be a purified protein.

Conditions for carrying out transglutaminase conjugation reactions are known in the art, and any conditions for carrying out transglutaminase conjugation reactions known to those skilled in the art in view of the present disclosure can be used in the invention.

In a preferred embodiment, an engineered antibody of the invention is not deglycosylated before it is contacted with the amine-containing payload and the transglutaminase to produce the antibody-payload conjugate.

In another general aspect, the invention relates to nucleic acids encoding engineered antibodies or fragments thereof of the invention. As used herein, the term "nucleic acid" refers to a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

In another general aspect, the invention relates to vectors comprising nucleic acids of the invention. As used herein, the term "vector" refers to a nucleic acid molecule that can be used to transport a second nucleic acid molecule into a cell. In one embodiment, the vector allows for replication of DNA sequences inserted into the vector. The vector can comprise a promoter to enhance expression of the nucleic acid molecule in at least some host cells. Vectors can replicate autonomously (extrachromasomal) or can be integrated into a host cell chromosome. In one embodiment, the vector can comprise an expression vector capable of producing a protein derived from at least part of a nucleic acid sequence inserted into the vector.

In another general aspect, the invention relates to host cells comprising nucleic acids or vectors of the invention. As used herein, the term "host cell" refers to a cell that is grown in culture according to the present invention to produce a protein or polypeptide of interest. In certain embodiments, the host cell is a mammalian cell.

In another general aspect, the invention relates to methods of producing an engineered antibody of the invention comprising incubating a host cell of the invention under suitable conditions for expressing the antibody or fragment thereof, and isolating the antibody or fragment thereof.

Pharmaceutical Compositions and Methods of Treatment

In another general aspect, the invention relates to a pharmaceutical composition comprising an engineered antibody of the invention, or an antibody-payload conjugate of the invention, and a pharmaceutically acceptable carrier.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody-based pharmaceutical composition can be used in the invention.

According to particular embodiments, the compositions described herein are formulated to be suitable for the intended route of administration to a subject. For example, the compositions described herein can be formulated to be suitable for intravenous, subcutaneous, intramuscular or intratumoral administration.

In another general aspect, the invention relates to a method of treating a disease or disorder in a subject in need thereof, comprising administering to the subject the pharmaceutical composition of the invention. According to particular embodiments, the disease or disorder is a tumor, such as a solid tumor or a blood borne tumor, particularly the tumor is a cancer.

According to particular embodiments, a method of the invention comprises administering a therapeutically effective dose of a pharmaceutical composition of the invention, wherein the composition comprises an antibody-drug conjugate for targeting cells associated with the disease or disorder such that, upon targeting, the drug is delivered to the targeted cells and causes an effect thereto, thereby treating the disease or disorder.

As used herein, the term "therapeutically effective amount" refers to an amount of an active ingredient or component that elicits the desired biological or medicinal response in a subject. Selection of a particular effective dose can be determined (e.g., via clinical trials and/or pre-clinical assays) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. In some cases, effective doses can be extrapolated from dose-response curves derived from in vitro or animal model test systems.

As used herein, the terms "treat," "treating," and "treatment" are all intended to refer to an amelioration or reversal of at least one measurable physical parameter related to a disease, disorder, or condition in which administration of an antibody-drug conjugate would be beneficial, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition in which administration of an antibody-drug conjugate would be beneficial. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig, marmoset or mouse) or a primate (e.g., a monkey, chimpanzee, or human). In particular embodiments, the subject is a human.

According to particular embodiments, compositions used in the treatment of a disease or disorder can be used in combination with other agents that are effective for treatment of related diseases or disorders.

As used herein, the term "in combination," in the context of the administration of two or more therapies to a subject, refers to the use of more than one therapy. The use of the term "in combination" does not restrict the order in which therapies are administered to a subject.

Combinations and Kits

Provided herein is a combination or kit comprising:
a. an engineered antibody of the invention; and
b. transglutaminase;
wherein the combination or kit is to be used for labeling the antibody with an amine-containing payload.

According to particular embodiments, a combination of the invention is a reaction mixture used to conjugate the antibody with the payload. Optionally associated with the combination can be a notice or instructions in the form prescribed by a governmental agency regulating the manufacture, use or sale of pharmaceuticals or biological products, which notice reflects approval by the agency of manufacture, use or sale for human administration. The combinations encompassed herein can be used in the above methods of conjugating an antibody with a payload, or of treating a disease or disorder in a subject in need thereof.

EMBODIMENTS

Embodiment 1 is an engineered antibody comprising an amino acid substitution at heavy chain position 302 of the antibody, wherein the amino acid numbering is according to the EU Index of Kabat.

Embodiment 2 is the engineered antibody of Embodiment 1, wherein the amino acid substitution is selected from the group consisting of V302S, V302A, V302I, V302L, V302M, V302T, V302F, and V302Y.

Embodiment 2a is the engineered antibody of Embodiment 2, wherein the amino acid substitution is V302S.

Embodiment 2b is the engineered antibody of Embodiment 2, wherein the amino acid substitution is V302A.

Embodiment 3 is the engineered antibody of Embodiment 1, 2 or 2a, further comprising a glutamine substitution at heavy chain position 286, 287, 288, 289, 290, 293 or 294.

Embodiment 3a is the engineered antibody of Embodiment 3, wherein the glutamine substitution is at heavy chain position 293.

Embodiment 3b is the engineered antibody of Embodiment 3, wherein the glutamine substitution is at heavy chain position 294.

Embodiment 4 is the engineered antibody of Embodiment 3, wherein the glutamine substitution is N286Q, A287Q, K288Q, T289Q, K290Q, E293Q or E294Q.

Embodiment 5 is the engineered antibody of Embodiment 4, wherein the glutamine substitution is E294Q.

Embodiment 5a is the engineered antibody of Embodiment 4, wherein the glutamine substitution is E293Q.

Embodiment 6 is the engineered antibody of any of Embodiments 1 to 5a, further comprising an alanine substitution at heavy chain position 241, 243, 294 or 301.

Embodiment 7 is the engineered antibody of Embodiment 6, wherein the alanine substitution is F241A, F243A, E294A or R301A.

Embodiment 8 is the engineered antibody of any of Embodiments 1 to 7, further comprising an amino acid substitution at heavy chain position 300.

Embodiment 9 is the engineered antibody of Embodiment 8, wherein the amino acid substitution at heavy chain position 300 is Y300L.

Embodiment 10 is an engineered antibody comprising an amino acid substitution at heavy chain position 294 of the antibody, wherein the amino acid numbering is according to the EU Index of Kabat.

Embodiment 11 is the engineered antibody of Embodiment 10, wherein the amino acid substitution at heavy chain position 294 is a glutamine substitution.

Embodiment 11a is the engineered antibody of Embodiment 11, wherein the glutamine substitution is E294Q.

Embodiment 12 is the engineered antibody of Embodiment 10, wherein the amino acid substitution at heavy chain position 294 is an alanine substitution.

Embodiment 12a is the engineered antibody of Embodiment 12, wherein the alanine substitution is E294A.

Embodiment 13 is the engineered antibody of Embodiment 10, wherein the amino acid substitution at heavy chain position 294 is a methionine substitution.

Embodiment 13a is the engineered antibody of Embodiment 13, wherein the methionine substitution is E294M.

Embodiment 14 is the engineered antibody of Embodiment 10, wherein the amino acid substitution at heavy chain position 294 is a phenylalanine substitution.

Embodiment 14a is the engineered antibody of Embodiment 14, wherein the phenylalanine substitution is E294F.

Embodiment 15 is the engineered antibody of Embodiment 10, wherein the amino acid substitution at heavy chain position 294 is a lysine substitution.

Embodiment 15a is the engineered antibody of Embodiment 15, wherein the lysine substitution is E294K.

Embodiment 16 is the engineered antibody of Embodiment 10, wherein the amino acid substitution at heavy chain position 294 is a leucine substitution.

Embodiment 16a is the engineered antibody of Embodiment 16, wherein the leucine substitution is E294L.

Embodiment 17 is the engineered antibody of Embodiment 10, wherein the amino acid substitution at heavy chain position 294 is an arginine substitution.

Embodiment 17a is the engineered antibody of Embodiment 17, wherein the arginine substitution is E294R.

Embodiment 18 is the engineered antibody of Embodiment 10, wherein the amino acid substitution at heavy chain position 294 is a valine substitution.

Embodiment 18a is the engineered antibody of Embodiment 18, wherein the valine substitution is E294V.

Embodiment 19 is the engineered antibody of Embodiment 10, wherein the amino acid substitution at heavy chain position 294 is a tyrosine substitution.

Embodiment 19a is the engineered antibody of Embodiment 19, wherein the tyrosine substitution is E294Y.

Embodiment 20 is the engineered antibody of Embodiment 11 or 11a, further comprising an amino acid substitution at heavy chain position 295.

Embodiment 20a is the engineered antibody of Embodiment 20, wherein the amino acid substitution at heavy chain position 295 is Q295A.

Embodiment 20b is the engineered antibody of Embodiment 20, wherein the amino acid substitution at heavy chain position 295 is Q295E.

Embodiment 20c is the engineered antibody of Embodiment 20, wherein the amino acid substitution at heavy chain position 295 is Q295N.

Embodiment 21 is the engineered antibody of Embodiment 12 or 12a, further comprising an amino acid substitution at heavy chain position 288.

Embodiment 21a is the engineered antibody of Embodiment 21, wherein the amino acid substitution at heavy chain position 288 is K288Q.

Embodiment 22 is the engineered antibody of any of Embodiments 10 to 12a, further comprising an amino acid substitution at heavy chain position 302.

Embodiment 23 is the engineered antibody of Embodiment 22, wherein the amino acid substitution at heavy chain position 302 is V302S, V302A, V302I, V302L, V302M, V302T, V302F, or V302Y.

Embodiment 23a is the engineered antibody of Embodiment 23, wherein the amino acid substitution at heavy chain position 302 is V302S.

Embodiment 23b is the engineered antibody of Embodiment 23, wherein the amino acid substitution at heavy chain position 302 is V302A.

Embodiment 24 is the engineered antibody of any of Embodiments 10 to 12a and 22 to 23b, further comprising an amino acid substitution at heavy chain position 300.

Embodiment 25 is the engineered antibody of Embodiment 24, wherein the amino acid substitution at heavy chain position 300 is Y300L.

Embodiment 26 is an engineered antibody comprising an amino acid substitution at heavy chain position 302 and an amino acid substitution at heavy chain position 293, wherein the amino acid numbering is according to the EU Index of Kabat.

Embodiment 27 is an engineered antibody comprising an amino acid substitution at heavy chain position 302 and an amino acid substitution at heavy chain position 294, wherein the amino acid numbering is according to the EU Index of Kabat.

Embodiment 28 is an engineered antibody comprising the amino acid substitution V302S and at least one of the amino acid substitutions E293Q and E294Q, wherein the amino acid numbering is according to the EU Index of Kabat.

Embodiment 29 is an engineered antibody comprising the amino acid substitution V302S and the amino acid substitution E293Q, wherein the amino acid numbering is according to the EU Index of Kabat.

Embodiment 30 is an engineered antibody comprising the amino acid substitution V302A and the amino acid substitution E293Q, wherein the amino acid numbering is according to the EU Index of Kabat.

Embodiment 31 is an engineered antibody comprising the amino acid substitution V302S and the amino acid substitution E294Q, wherein the amino acid numbering is according to the EU Index of Kabat.

Embodiment 32 is an engineered antibody comprising the amino acid substitution V302A and the amino acid substitution E294Q, wherein the amino acid numbering is according to the EU Index of Kabat.

Embodiment 33 is the engineered antibody of any of Embodiments 26 to 32, further comprising an amino acid substitution at heavy chain position 300.

Embodiment 33a is the engineered antibody of Embodiment 33, wherein the amino acid substitution at heavy chain position 300 is Y300L.

Embodiment 34 is the engineered antibody of any of Embodiments 1 to 33, wherein the antibody is a human IgG antibody.

Embodiment 34a is the engineered antibody of Embodiment 34, wherein the human IgG antibody is a human IgG1 antibody.

Embodiment 34b is the engineered antibody of Embodiment 34, wherein the human IgG antibody is a human IgG2 antibody.

Embodiment 34c is the engineered antibody of Embodiment 34, wherein the human IgG antibody is a human IgG4 antibody.

Embodiment 35 is the engineered antibody of any of Embodiments 1 to 34c, wherein the antibody is glycosylated.

Embodiment 35a is the engineered antibody of any of Embodiments 1 to 34c, wherein the antibody glycan of the engineered antibody is not removed.

Embodiment 36 is an antibody-payload conjugate, comprising the engineered antibody of any of Embodiments 1 to 35a.

Embodiment 37 is the antibody-payload conjugate of Embodiment 36, wherein the payload comprises one or more selected from the group consisting of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, and a first click reaction partner.

Embodiment 38 is the antibody-payload conjugate of Embodiment 36 or 37, wherein the payload is conjugated to the engineered antibody at the endogenous heavy chain Q295 residue of the antibody.

Embodiment 39 is the antibody-payload conjugate of Embodiment 36, 37 or 38, wherein the payload is conjugated to the engineered antibody at the glutamine residue at heavy chain position 286, 287, 288, 289, 290, 293 or 294 of the engineered antibody.

Embodiment 40 is the antibody-payload conjugate of any of Embodiments 36 to 39, wherein the payload is conjugated to the engineered antibody at Q295 and at least one of the glutamine residues at heavy chain positions 293 and 294.

Embodiment 40a is the antibody-payload conjugate of Embodiment 40, wherein the payload is conjugated to the engineered antibody at Q295 and at the glutamine residue at heavy chain position 293.

Embodiment 40b is the antibody-payload conjugate of Embodiment 40, wherein the payload is conjugated to the engineered antibody at Q295 and at the glutamine residue at heavy chain position 294.

Embodiment 41 is the antibody-payload conjugate of any of Embodiments 36 to 40b, having a drug antibody ratio (DAR) of 1 to 4.

Embodiment 41a is the antibody-payload conjugate of Embodiment 41, having a DAR of 2 to 4.

Embodiment 42 is the antibody-payload conjugate of any of Embodiments 36 to 41, having a DAR of 2.

Embodiment 43 is the antibody-payload conjugate of any of Embodiments 36 to 41, having a DAR of 4.

Embodiment 44 is a method of generating an antibody-payload conjugate, the method comprising: contacting the engineered antibody of any of Embodiments 1 to 35a and an amine-containing payload with a transglutaminase under a condition to generate the antibody-payload conjugate comprising the engineered antibody conjugated to the payload.

Embodiment 45 is the method of Embodiment 44, wherein the method does not include removing the antibody glycan of the engineered antibody.

Embodiment 46 is the method of Embodiment 44 or 45, wherein the amine-containing payload comprises one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, and a first click reaction partner.

Embodiment 47 is the method of any of Embodiments 44 to 46, wherein the amine-containing payload comprises a first click reaction partner.

Embodiment 48 is the method of Embodiment 47, wherein the method further comprises reacting the antibody-payload conjugate with a second click reaction partner that comprises one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin to obtain a second antibody-payload conjugate.

Embodiment 49 is the method of Embodiment 47 or 48, wherein the first click reaction partner is 3-azido-1-propylamine, and wherein the second click reaction partner is dibenzocyclooctyne-tetraethylene glycol-valine-citrulline-paraaminobenzyl carbamate-monomethyl auristatin F (DBCO-val-cit-MMAF) or dibenzocyclooctyne-tetraethylene glycol-monomethyl auristatin F (DBCO-MMAF).

Embodiment 50 is the method of any of Embodiments 4 to 49, wherein the engineered antibody has not been subject to deglycosylation before it is conjugated to the payload.

Embodiment 51 is a pharmaceutical composition comprising the engineered antibody of any of Embodiments 1 to 35a, and a pharmaceutically acceptable carrier.

Embodiment 52 is a pharmaceutical composition comprising the antibody-payload conjugate of any of Embodiments 36 to 43, and a pharmaceutically acceptable carrier.

Embodiment 53 is a method of treating a disease or disorder in a subject in need thereof, the method comprising administering to the subject the pharmaceutical composition of Embodiment 51 or 52.

Embodiment 54 is the method of Embodiment 53, wherein the disease or disorder is a tumor, such as a solid tumor or a blood borne tumor, particularly the tumor is a cancer.

Embodiment 55 is a nucleic acid encoding the engineered antibody of any of Embodiments 1 to 35a.

Embodiment 56 is a host cell comprising the nucleic acid of Embodiment 55. Embodiment 57 is a method for producing an engineered antibody, the method comprising incubating the host cell of Embodiment 56 under suitable conditions for expressing the engineered antibody.

Embodiment 57a is the method of embodiment 57, further comprising isolating the engineered antibody.

Embodiment 58 is a kit comprising (a) the engineered antibody of any of Embodiments 1 to 35a; and (B) a transglutaminase.

EXAMPLES

The following examples of the invention are to further illustrate the nature of the invention. It should be understood that the following examples do not limit the invention and that the scope of the invention is to be determined by the appended claims.

Example 1: Rodent IgGs have an Additional Transglutaminase-Catalyzed Modification Site in the CH2 Domain While using the deglycosylation method (Jeger et al., Id.) to conjugate 3-azido propylamine (3-APA) to NLDC-145, a rat IgG2a mAb targeting murine DEC205, it was observed that 3-APA conjugated at four positions per deglycosylated mAb (two per monomer) and not two as is observed in human IgGs (at position Gln295). No further addition was observed past four molecules of 3-APA, suggesting that there are two discrete conjugation sites per monomer in this mAb. Peptide mapping of the conjugated, deglycosylated NLDC-145 identified the expected attachment site, Gln295, and an additional site that was determined to be Gln288 (FIG. 1a).

Figure 1B:
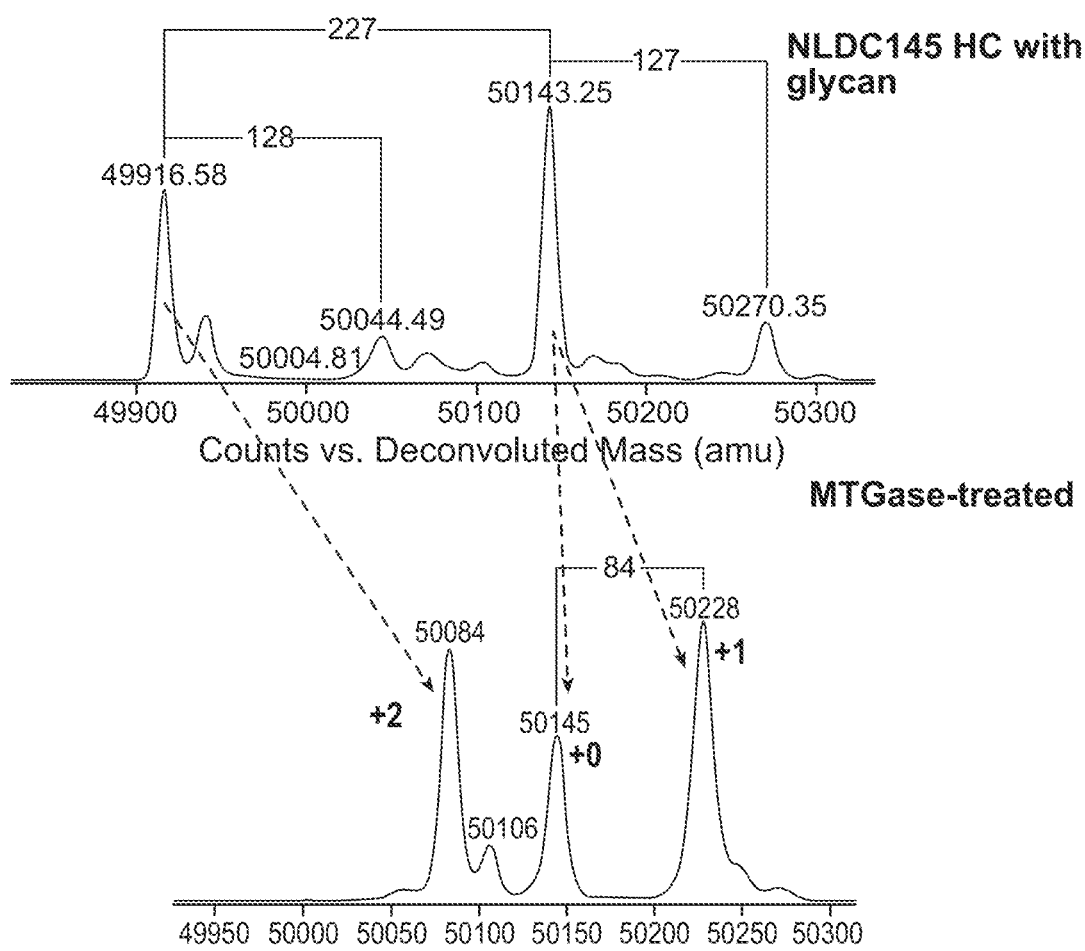
FIG. 1b shows the reduced mass LC/MS of intact NLDC-145 modified with MTG; the heavy chain with Man5 glycan (49917 Da) shows the addition of two molecules of 3-APA, while the heavy chain with GOF glycan (50143 Da) produces a mixture of addition of zero and one 3-APA molecules.

Upon reaction of NLDC-145 having intact glycan with 3-APA and MTG, conjugation was still observed producing a mixture of species ranging from zero to four 3-APA molecules per mAb. Peptide mapping of the conjugate showed that the primary modification site was Gln295 with some modification of Gln288. Reduced MS showed that the mAb glycan structure played a role in the reactivity to MTG, as mAbs with Man$_5$ glycan were found to be modified at both Gln295 and Gln288, while mAbs with GOF glycan had <1 modification per heavy chain (FIG. 1b). The melting temperature of the CH2 domain of mAbs with high-mannose glycan is 4.3° C. lower than the identical domain with GOF glycan (Wada et al., 2019, MAbs 11(2):350-372), suggesting that the GOF sugar contacts the protein in a way that provides additional stabilization to the CH2 domain. It was thought that altering this protein-sugar interaction by introducing specific point mutations into mAbs instead of modifying glycan could also allow for efficient MTG modification at Gln295—even with intact glycan and regardless of the glycan structure.

Example 2: Site-Specific Conjugation of Glycosylated Monoclonal Antibodies with Transglutaminase To determine if a mAb engineering strategy could allow for MTG-catalyzed conjugation of human IgGs, a series of variants of the humanized IgG1 mAb trastuzumab (see, e.g., Nahta and Esteva, 2007, Oncogene 26(25):3637-43) were produced. The variants were based on the structure of the CH2 domain, focusing on positions that are in proximity to position 295 and the beta-sheet on which it is located, and/or positions that contact the mAb glycan. In many cases, the variants were based on engrafting the corresponding sequence of rat IgG2a. The variants were reacted with transglutaminase and 3-APA and analyzed by mass spectrometry.

The mAbs were expressed in CHO cells and purified by protein A chromatography using standard methods. Reduced mAbs were analyzed by LC-MS to determine the distribution of the glycans present, and in all cases, GOF was the major species. Small amounts (<10%) of masses corresponding to other glycans were observed in some mAbs, and the K288Q/Y300L/V302S variant had a significant proportion that corresponded to G1F glycan.

To assess the suitability of the mAb variants for MTG-catalyzed conjugation, intact mAbs (1 mg/mL) were reacted with 3-azido propylamine (3-APA; 20-100-fold molar excess) and MTG (Activa TI, 5-20% w/v or Zedira, 5-20 units/mg of mAb) in PBS buffer at 22-37° C. for 30 min to overnight. Reactions were stopped by the addition of MTG blocker (Zedira) to 100 µM and analyzed by LC-MS following deglycosylation with PNGase F and reduction with dithiothreitol. The degree of labeling (DOL) was determined by mass spectrometry.

LC-MS was performed on an Agilent 1260 HPLC system connected to an Agilent G6224 MS-TOF Mass Spectrometer. LC was run on an Agilent RP-mAb C4 column (2.1×50 mm, 3.5 micron) at a flow rate of 1 mL/min with the mobile phase 0.1% formic acid in water (A) and 0.1% formic acid in acetonitrile (Sigma-Aldrich Cat #34688) (B) and a gradient of 20% B (0-2 min), 20-60% B (2-3 min), 60-80% B (3-5.5 min). The instrument was operated in positive electrospray ionization mode and scanned from m/z 600 to 6000. Mass to charge spectrum was deconvoluted using the Maximum Entropy algorithm and DOL was estimated using relative intensities of the deconvoluted masses corresponding to intact mAb (for intact mass) or mAb heavy chain (for reduced mass) with the addition of multiples of 83 Da (corresponding to 3-APA).

Instrument settings included: capillary voltage 3500V; fragmentor 175V; skimmer 65V; gas temperature 325C; drying gas flow 5.0 L/min; nebulizer pressure 30 psig; acquisition mode range 100-7000 with 0.42 scan rate.

TABLE 2

Degree of labeling (DOL) of glycosylated mAbs after 4 hour incubation with MTG and 3-APA at 37° C. DOL was determined by reduced MS analysis. Under these reaction conditions there was some conjugation observed on the heavy chain with all mAbs, including the WT; no modification was observed on light chains. DOL is reported for the full mAb, which is 2x the DOL observed by MS of the heavy chain.

| SEQ ID NO | Mutations | DOL |
| --- | --- | --- |
| 2 | | 0.2 |
| 3 | K288Q | 0.5-0.6 |
| 4 | K288Q/P291A/R292P | 1 |
| 5 | K288Q/Y300L/V302S | 2.2 |
| 6 | K288Q/P291A/R292P/Y300L/V302S | 0.8-1.1 |
| 7 | K288Q/K290H | 0.8 |
| 8 | K288Q/V305E | 0.8 |
| 9 | K288Q/E258K | 1 |
| 10 | K288Q/K290H/V305E | 0.7-1.5 |
| 11 | K288Q/K290H/V305E/E258K | 0.4 |

TABLE 2-continued

Degree of labeling (DOL) of glycosylated mAbs after 4 hour incubation with MTG and 3-APA at 37° C. DOL was determined by reduced MS analysis. Under these reaction conditions there was some conjugation observed on the heavy chain with all mAbs, including the WT; no modification was observed on light chains. DOL is reported for the full mAb, which is 2x the DOL observed by MS of the heavy chain.

| SEQ ID NO | Mutations | DOL |
|---|---|---|
| 12 | C'/D strand | 0 |
| 13 | C'/D and E strands | 0.6-0.8 |
| 14 | C'/D and E strands, E258K | 0.8-1 |
| 15 | K288Q/K290H/P291A/R292P/Y300L/V302S/V305E/E258K | 0.9-1 |
| 16 | Entire CH2 domain | 1-1.4 |
| 18 | F241A | 1.9 |
| 19 | F243A | 1.6 |
| 17 | R301A | 1.6 |
| 20 | K288Q/Y300L | 0.4 |
| 21 | K288Q/V302S | 1.3-1.5 |
| 23 | Y300L | 0.7 |
| 24 | V302S | 2 |

Figure 2:
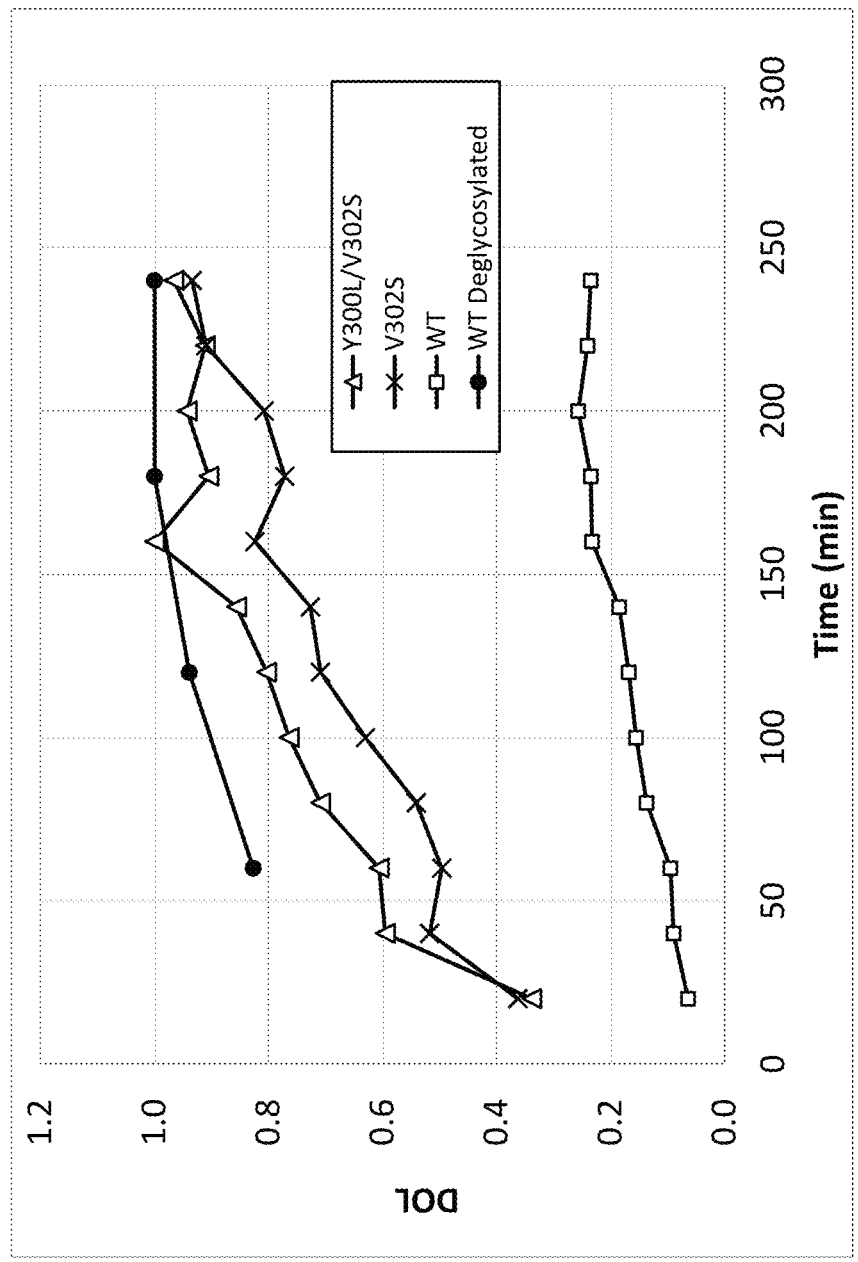
FIG. 2 shows the rates of MTG-catalyzed conjugation of 3-APA to trastuzumab variants; in particular, WT intact trastuzumab is compared to WT deglycosylated, Y300L/V302S, and V302S, and the degree of labeling (DOL) per heavy chain is displayed as a function of time.

A number of the combinations were found to increase the reaction rate of MTG-catalyzed 3-APA conjugation to human IgG to some degree (Table 2). In particular, the variant engrafting Y300L and V302S along with K288Q (SEQ ID NO: 5) was modified rapidly and reached full modification (DAR=2) on a timescale approaching fully deglycosylated WT mAb (Table 2). Additional variants with only one or two of these mutations were then constructed, and it was determined that Y300L/V302S was comparable to the triple mutant (FIG. 2 and Table 2). V302S was found to have a greater effect than Y300L on conjugation efficiency.

Additional variants of trastuzumab were constructed with mutations at the Val302 position: V302A, V302I, V302L, V302M, V302T, V302F, and V302Y. The reactivity of these variants with MTG was evaluated to determine which have similar or improved properties relative to the V302S variant.

TABLE 3

Reactivity of the Val 302 mutants. Degree of labeling (DOL) of glycosylated mAbs was determined by reduced MS analysis at 30 min intervals up to 150 min after incubation with MTG and 3-APA at 37° C. DOL is reported for the full mAb, which is 2x the DOL observed by MS of the heavy chain.

| SEQID | mutations | 0 min | 30 min | 60 min | 90 min | 120 min | 150 min |
|---|---|---|---|---|---|---|---|
| 2 | | 0 | 0.1 | 0.18 | 0.24 | 0.3 | 0.36 |
| 2 (deglycosylated) | | 0 | 1.14 | 1.64 | 1.82 | 2 | 2 |
| 24 | V302S | 0 | 0.4 | 0.88 | 1.18 | 1.48 | 1.66 |
| 35 | V302A | 0 | 0.6 | 0.9 | 1.12 | 1.32 | 1.48 |
| 36 | V302I | 0 | 0 | 0 | 0 | 0.28 | 0.34 |
| 37 | V302L | 0 | 0 | 0.36 | 0.44 | 0.52 | 0.58 |
| 38 | V302M | 0 | 0 | 0.28 | 0.46 | 0.6 | 0.58 |
| 39 | V302T | 0 | 0.28 | 0.56 | 0.76 | 1.02 | 1.14 |
| 40 | V302F | 0 | 0.12 | 0.18 | 0.36 | 0.48 | 0.38 |
| 41 | V302Y | 0 | 0 | 0 | 0.38 | 0.44 | 0.22 |

The V302A variant had a comparable reaction rate to V302S. The V302T variant was also significantly enhanced compared to the WT mAb, though it appears to be slower than V302A and V302S.

Example 3: Melting and Aggregation Temperature of Trastuzumab Variants

Trastuzumab mutants V302A, V302S and double mutant Y300L/V302S ("LS") were characterized more fully to demonstrate broad applicability of the conjugation approach and to assess the impact of the mutations on the mAb. Melting temperature ($T_m$) and aggregation temperature ($T_{agg}$) were determined by differential scanning fluorimetry using a nanoDSF instrument from Nanotemper. Tm was determined by monitoring changes in fluorescence intensity at 330 and 350 nm upon thermal scanning from 20 to 95° C., and Tagg was determined by monitoring the scattering. $T_{agg}$ was essentially unchanged for all mutants compared to WT trastuzumab (78-79° C.). The first $T_m$ corresponding to melting of the CH2 domain was 62.3° C. for the LS variant, reduced by ~8° C. relative to intact WT trastuzumab and similar to the first Tm of fully deglycosylated mAb. The V302S single mutant had a first Tm of 64.4° C., a reduction of 6° C. relative to WT mAb, and increased thermal stability compared to the CH2 domain of fully deglycosylated mAb by ~2° C. The V302A variant had a first Tm of 67.3° C., an increase of ~3° C. relative to V302S.

Additional characterization is performed to compare trastuzumab variants to the WT mAb and 3APA-conjugated variants to the 3APA-conjugated WT mAb. These assays include: determination of Tm/Tagg by DSF and/or DSC; long-term stability assays; non-specific binding assays; self-interaction and cross-interaction; and binding to FcRn and Fc receptors.

For DSF, the temperature of unfolding (Tm) and the temperature of aggregation (Tagg) were determined in PBS by differential scanning fluorimetry using the Prometheus nanoDSF instrument from Nanotemper. Tm was determined by monitoring changes in fluorescence intensity at 330 and 350 nm upon thermal scanning from 20 to 95° C., and Tagg was determined by monitoring the scattering.

For long-term stability, mAbs and conjugates were incubated at 4° C. or 40° C. in PBS or other relevant buffers for up to 4 weeks. At specified time points, aliquots of the samples were removed and stability was assessed by analytical SEC and LC-MS.

Non-specific binding was determined in an SPR-based assay using a Biacore 8K instrument. A panel of surfaces with different characteristics was generated by immobilizing different proteins (soybean trypsin inhibitor, defensin-3, human IgG, lysozyme, integrin alpha-4 beta-7, IL-13) onto a CM5 chip (GE) by amine coupling. Samples were run over the different surfaces and non-specific binding was estimated by determining the resonance units (RU) for each. Self-interaction was measured by affinity capture self interaction nanoparticle spectroscopy (AC-SINS) essentially as described (Liu et al. mAbs 2014:483). Cross interaction was measured by cross-interaction chromatography (CIC) essentially as described (Bethea et al. Prot Eng Des Sel 2012:531). FcRn binding was assessed using an Agilent HPLC equipped with an FcRn column (Mackness et al. mAbs 2019:1276). Samples were injected and a pH gradient (5.5-9.5) was run. Retention times were compared for the different samples to estimate FcRn binding. Fc receptor binding was compared by SPR or by ELISA.

Figure 3:
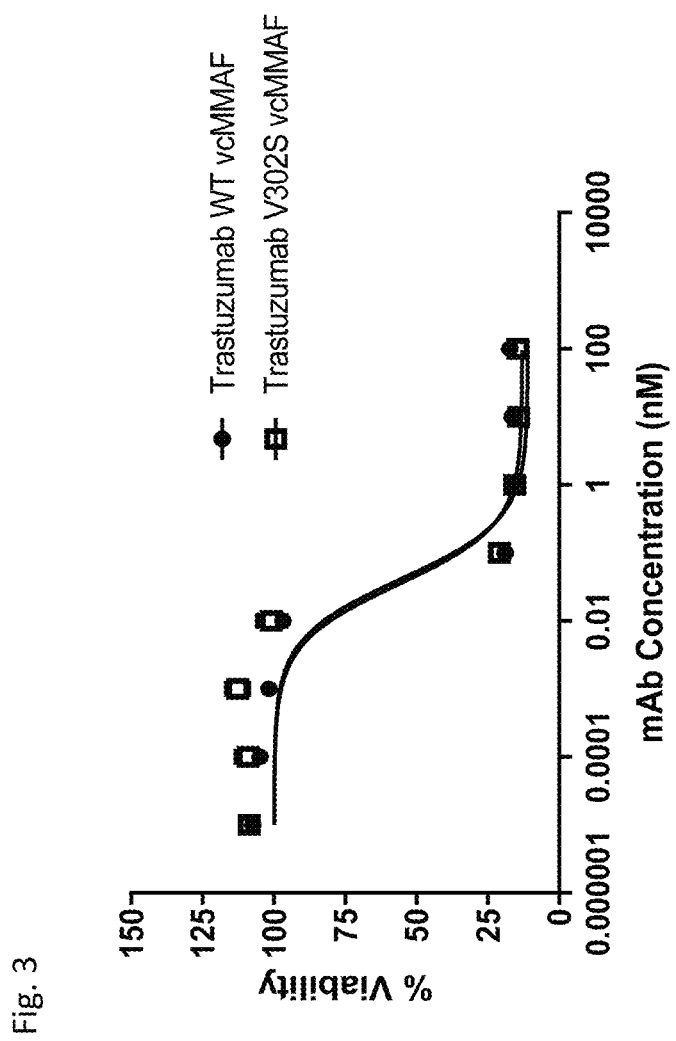
FIG. 3 shows a comparison of the activity of Trastuzumab-MMAF drug conjugates produced either with WT trastuzumab via established transglutaminase methods or using the glycan-intact V302S variant. For both ADCs, the drug payload is MMAF attached via a cleavable Val-Cit-PABC linker with DAR=2. SK-BR3 cells were treated with varying concentrations of conjugate for 72 hrs, and cell killing was determined by Cell Titer Glo assay.

Example 4: Cell-Based Activity Assays of ADCs Constructed with Trastuzumab V302S The V302S variant was modified with 3-APA to produce the azide-modified mAb. The azido-mAb was purified by protein A affinity chromatography and then reacted with DBCO-val-cit-MMAF or DBCO-MMAF to yield antibody drug conjugates with DAR=2. ADCs were also constructed with WT trastuzumab and these payloads using the deglycosylation/Gln295 conjugation method. The ADCs along with relevant controls were evaluated in cell assays, and the activity was found to be similar regardless of conjugation method (FIG. 3). SKBR3 cells, a cell line with high Her2 expression, were treated with varying concentrations of the ADCs for 72 hr at 37 C. Cell Titer Glo was used to determine cell viability at the conclusion of the treatment. Accordingly, using specific substitutions in the heavy chain of the antibody in order to enhance conjugation efficiency does not impact the cytotoxic activity of the resulting antibody-payload conjugate.

Example 5: Engrafting of Gln at Position 288 or at Other Positions on the Beta-Sheet, in Combination with a V302S Mutation, Provides mAbs that can be Conjugated to DAR=2 (with Glycan) or DAR=4 (without Glycan)

Trastuzumab variants were constructed with the Y300L/V302S/K288Q or V302S/K288Q mutations engrafted based on the rat IgG2a sequence and expressed and purified as described above. These variants were rapidly modified by MTG upon reaction with 3-APA to reach a DAR of two (FIG. 4a) under standard conditions. Mapping of the conjugation site determined that the majority of 3-APA was added at Gln295, with a small fraction at Gln288. When the mAbs were deglycosylated prior to reaction, the conjugates reached a DAR of four (FIG. 4b) under standard conditions, similar to the NLDC-145 rat IgG2a mAb.

Additional variants were constructed in which the Y300L and V302S mutations were maintained, while the position of the additional Gln was shifted between positions 285 and 294. Many of these variants had similar profiles to the Y300L/V302S/K288Q variant and the rat IgG2a, conjugating to 3-APA to reach DAR=2 with glycan and DAR=4 without glycan. Exceptions include the R292Q variant, which had decreased reactivity, and the E293Q and E294Q variants, as described in more detail in Example 6 below.

Table 4 shows the degree of labeling (DOL) per mAb after incubation with TGase and 3-APA at 37 C. The DOL was determined by MS analysis of mAb heavy chains; no modification was observed on light chains. DOL is reported for the full mAb, which is 2x the DOL observed by MS of the heavy chain.

TABLE 4

Degree of labeling (DOL) of mAbs after incubation with MTG and 3-APA at 37° C. for 4.5 hour (†) or 1.5 hour (*). DOL is reported for the full mAb, which is 2x the DOL observed by MS of the heavy chain.

| SEQ ID NO | Mutations | DOL (intact) | DOL (Deglycosylated) |
|---|---|---|---|
| 2 |  | 0.4 † | 2 |
| 5 | K288Q/Y300L/V302S | 2.1 † | 3.2 |
| 26 | H285Q/Y300L/V302S | 2 † | 2 |
| 27 | N286Q/Y300L/V302S | 2.3 † | 3.5 |
| 28 | A287Q/Y300L/V302S | 2.2 † | 1.8 |
| 29 | T289Q/Y300L/V302S | 2.1 † | 3.0 |
| 30 | K290Q/Y300L/V302S | 1.7 † | 2.3 |
| 31 | R292Q/Y300L/V302S | 1.2 † | 2.4 |
| 32 | E293Q/Y300L/V302S | 3.6* |  |
| 33 | E294Q/Y300L/V302S | 3.9* |  |

Figure 4A:
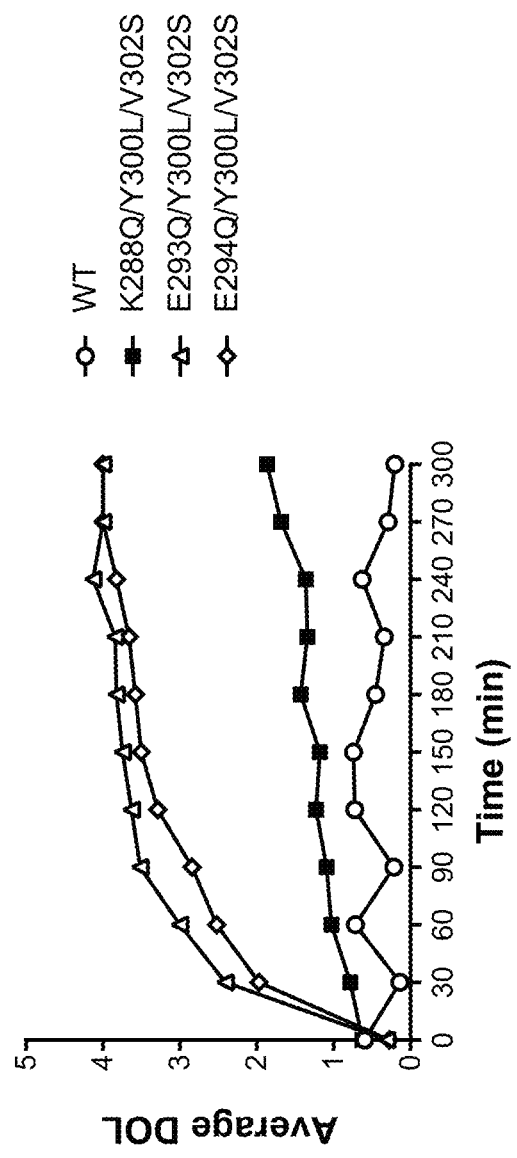
FIG. 4a shows the rate of MTG-catalyzed conjugation of 3-APA to trastuzumab variants; in particular, WT intact trastuzumab is compared to K288Q/Y300L/V302S, E293Q/Y300L/V302S and E294Q/Y300L/V302S, and the degree of labeling (DOL) is displayed as a function of time.

Example 6: E293Q and E294Q Mutations Allow Conjugation to DAR=4 without Glycan Removal Inventors of the application surprisingly discovered that combining a mutation at heavy chain position 302, such as V302S, with an additional Gln residue at a position near 295 resulted in an mAb that could be conjugated to reach DAR=4 without removing glycan from the mAb. Preferably, the mAb can further contain a mutation and heavy chain 300, such as Y300L, to further improve the conjugation. Trastuzumab variants E293Q/Y300L/V302S and E294Q/Y300L/V302S were constructed and tested in reactions with MTG and 3-APA. In both cases, rapid addition of 4 molecules of 3-APA per mAb was observed; reactions went to completion in 4-5 hours with only 1.25 U/mg of Zedira MTG (FIG. 4a).

Figure 4B:
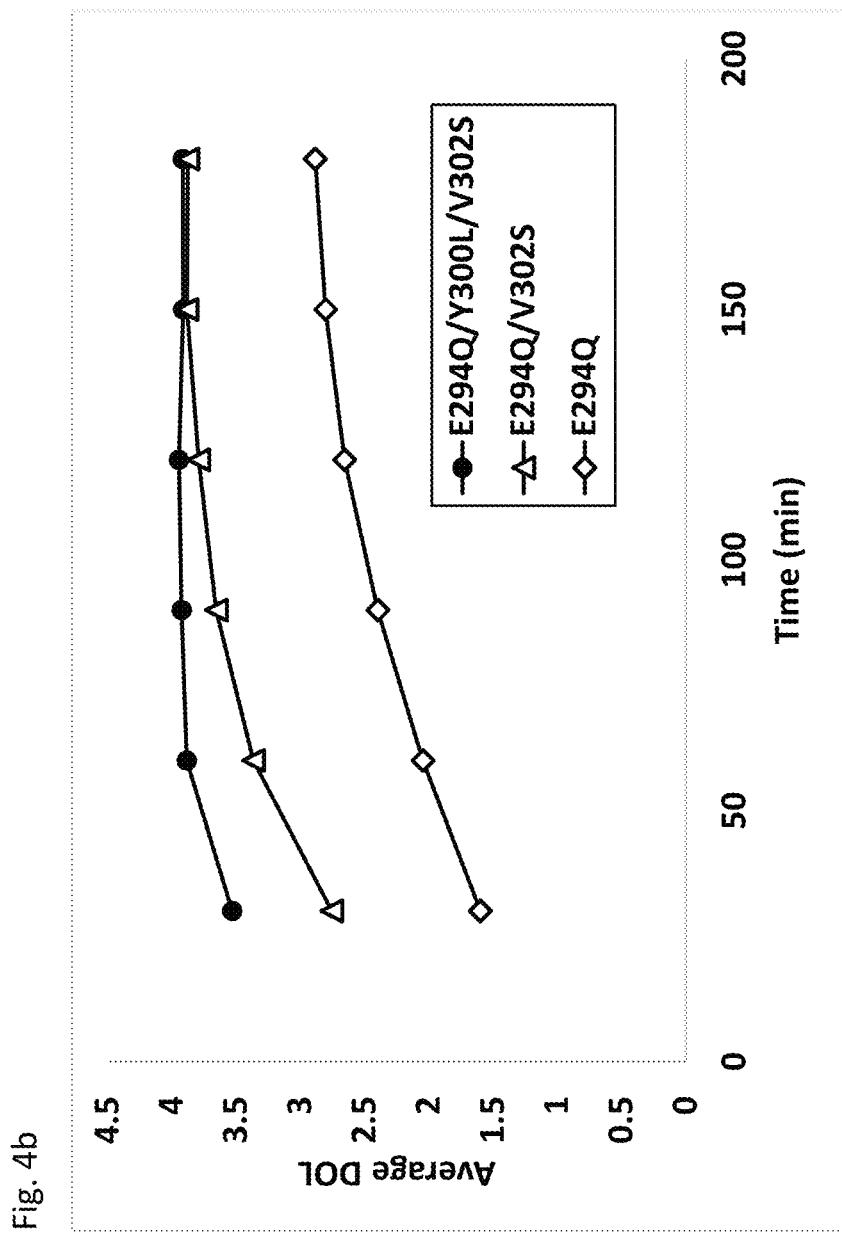
FIG. 4b shows a comparison of reaction rates with E294Q/Y300L/V302S, E294Q/V302S, and E294Q.

The Y300L/V302S/E294Q variant was characterized further. Additional variants were constructed with a subset of the Y300L/V302S/E294Q mutations to determine the roles of each in producing DAR=4 conjugates. The double mutant V302S/E294Q and the single mutant E294Q of trastuzumab were produced and the reactivity was tested with MTG and 3-APA (FIG. 4b). Under standard reaction conditions (1 mg/mL mAb, 690 uM 3-APA, 10 U/mg Zedira MTG, PBS buffer, 37 C) the E294Q/Y300L/V302S variant reached DAR=4 very rapidly and was essentially complete within 60 minutes. The E294Q/V302S variant was slower and needed ~150 min to reach DAR=4. The variant with the E294Q mutation alone also showed fairly rapid conjugation, exceeding DAR=2 in 60 minutes and reaching DAR=3 in 3 hours. After overnight incubation at 37 C, the E294Q variant also reached a full DAR=4.

Figure 4C:
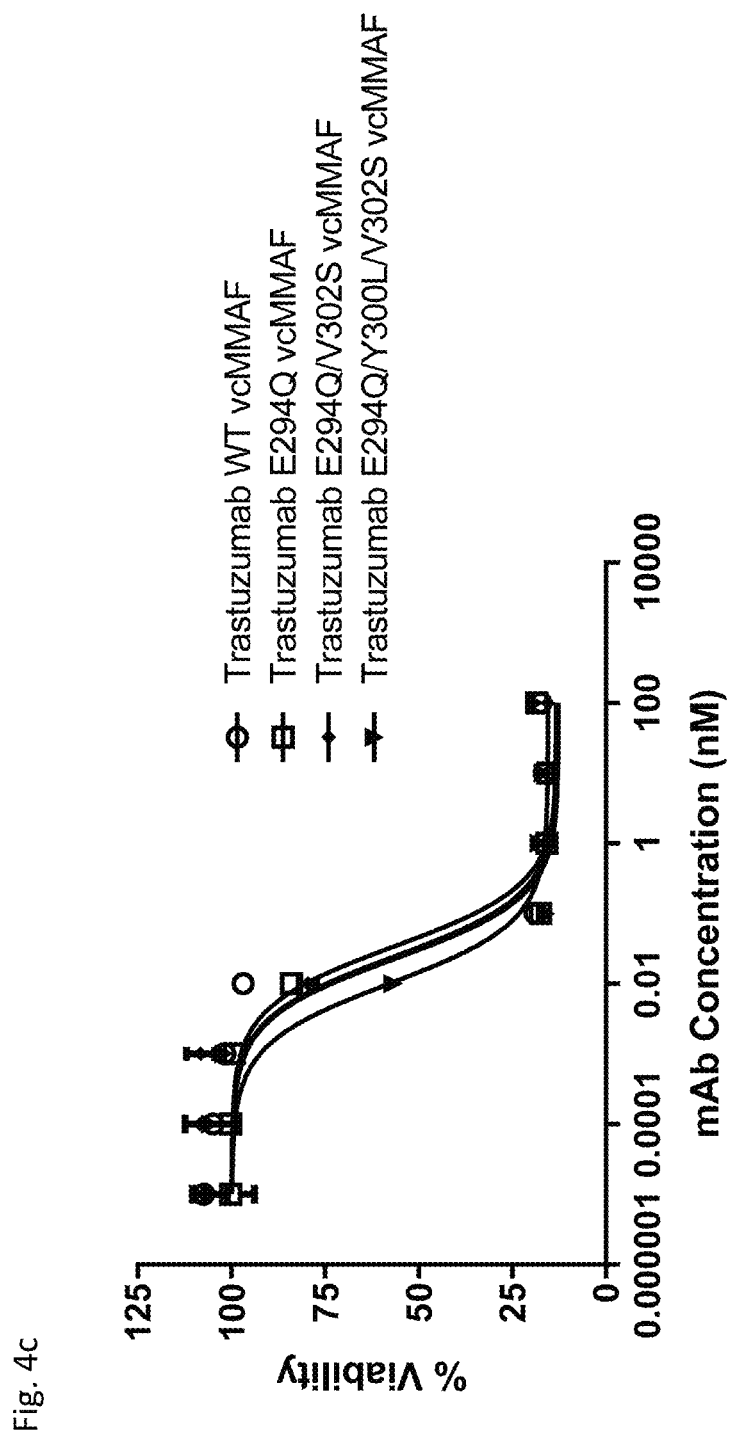
FIG. 4c shows a comparison of the activity of DAR=4 trastuzumab-MMAF drug conjugates produced from the variants with conjugates produced by deglycosylation and MTG-catalyzed conjugation. WT trastuzumab was conjugated via established transglutaminase methods to DAR=2, and variants were conjugated without removing glycan to DAR=4. For all ADCs the drug payload is MMAF attached via a cleavable Val-Cit-PABC linker. SK-BR3 cells were treated with varying concentrations of conjugate for 72 hrs, and cell killing was determined by Cell Titer Glo assay.

The E294Q, E294Q/V302S, and E294Q/Y300L/V302S variants were also conjugated to the drug payload vcMMAF to DAR=4 and compared to ADCs made by the standard deglycosylation method (FIG. 4c). In all cases the variants showed activity in the cell assay comparable to or more potent than the WT trastuzumab conjugated by the standard method.

Therefore, substitution to a glutamine at position E293 or E294, alone or in combination with other substitutions (e.g. at positions 302 and 300), provides an engineered antibody, with an intact glycan, that can be conjugated to a payload to an increased drug to antibody ratio (e.g. to DAR=4) more efficiently than a WT mAb, while retaining or improving stability and cytotoxic activity compared to the WT mAb.

Example 7: Combination of E294Q with Mutation of Gln295 Enables Very Rapid Conjugation with Intact Glycan mAbs After noting the rapid rate of conjugation of E294Q-containing mAbs to reach DAR 4 as described in Example 6 above, it was proposed that a mAb with E294Q along with a mutation altering the amino acid at position 295 could enable very fast conjugation to DAR=2 with glycan-intact mAbs. 3 such variants of trastuzumab were constructed: E294Q/Q295A, E294Q/Q295E, and E294Q/Q295N. These variants were reacted with MTG and 3-APA under the standard conditions described above and compared to WT mAb and deglycosylated WT mAb. Table 5 shows the (DOL) per mAb after 1 hour incubation with TGase and 3-APA at 37 C. The DOL was determined by MS analysis of mAb heavy chains; no modification was observed on light chains. DOL is reported for the full mAb, which is 2× the DOL observed by MS of the heavy chain.

TABLE 5

Degree of labeling (DOL) of mAbs after incubation with MTG and 3-APA at 37° C. for 1 hour. DOL is reported for the full mAb, which is 2x the DOL observed by MS of the heavy chain.

| SEQID | mutations | DOL |
| --- | --- | --- |
| 2 |  | 0.5 |
| 2 (deglycosylated) |  | 1.4 |
| 60 | E294Q/Q295A | 1.8 |
| 61 | E294Q/Q295E | 1.9 |
| 62 | E294Q/Q295N | 1.8 |

Figure 5:
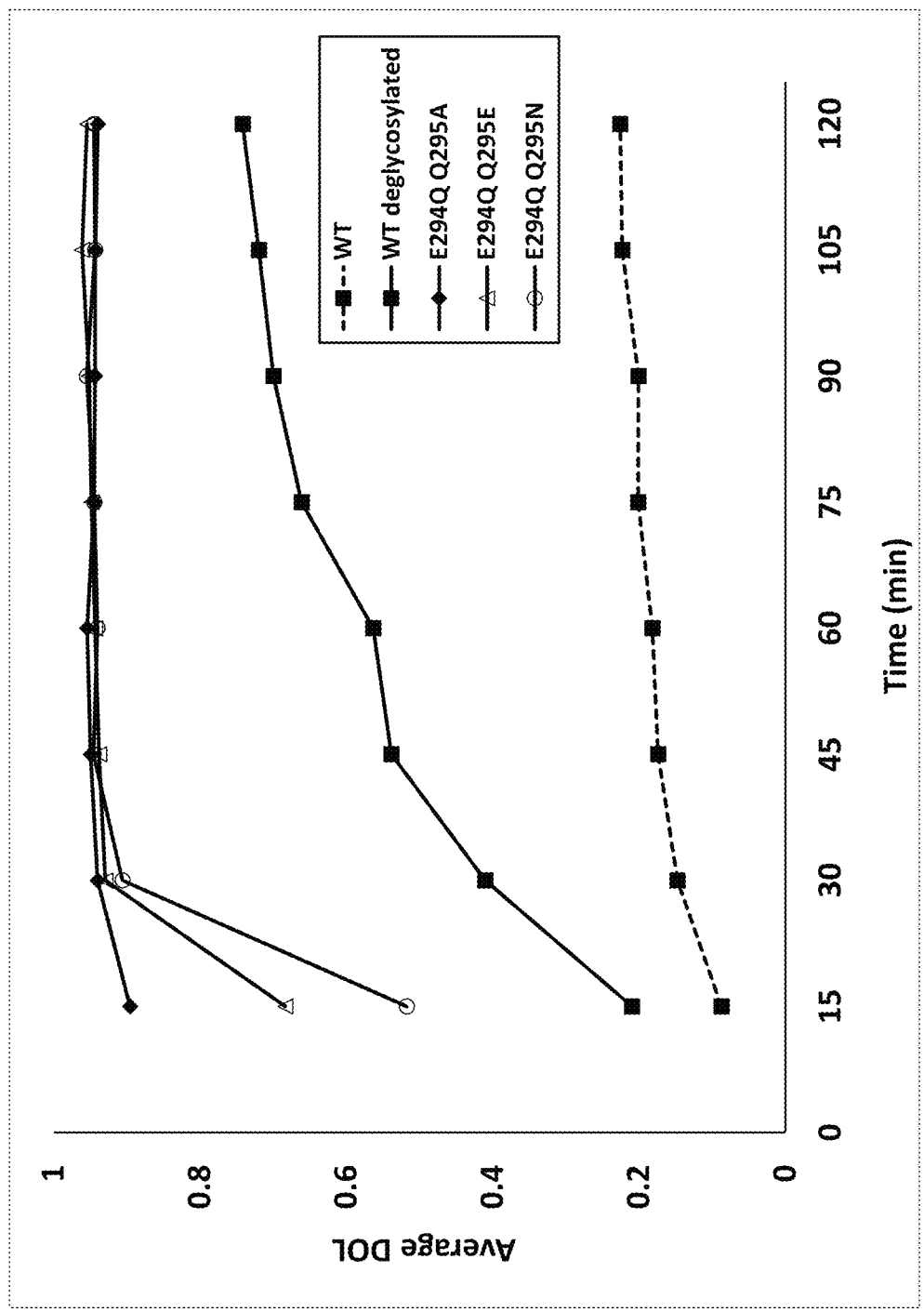
FIG. 5 shows the rate of MTG-catalyzed conjugation of 3-APA to trastuzumab variants; in particular, WT intact trastuzumab is compared to glycan-intact E294Q/Q295A, E294Q/Q295E, E294Q/Q295N and deglycosylated WT trastuzumab, and the degree of labeling (DOL) is shown as a function of time.

The double mutants were modified very rapidly by MTG, essentially reaching completion by 1 hour. The mutants, with intact glycan, appear to react even faster than WT deglycosylated trastuzumab which reached DOL ~1.4 at the 1 hour timepoint. To further compare the reaction rates of the double mutants to WT deglycosylated mAb, conjugation was monitored over time in reactions containing lower enzyme and substrate concentrations. Antibodies (WT trastuzumab, WT deglycosylated, QA, QE, QN variants) at 1 mg/mL were combined with 5 U/mg Zedira MTG and 345 μM 3-APA and incubated at 37° C. Samples were removed every 15 minutes and quenched by the addition of MTG blocker to 100 μM. Samples were deglycosylated with Rapid PNGase (1 μL per 25 μL sample, 50° C., 20 min) reduced with DTT at 25 mM, and analyzed by LC-MS. Under these conditions, the WT deglycosylated mAb reaches ~75% after 2 hours of reaction. In contrast, the variants have essentially gone to completion by the 30 or 45 minute time point (FIG. 5).

Melting temperature ($T_m$) and aggregation temperature ($T_{agg}$) were determined by differential scanning fluorimetry using a nanoDSF instrument from Nanotemper. $T_{agg}$ was essentially unchanged for all mutants compared to WT trastuzumab (78-79° C.). The first $T_m$ corresponding to melting of the CH2 domain was 68.1° C. for the QA variant, within ~2° C. of intact WT trastuzumab. The QE variant was 66.1° C., while the QN variant was 67.3° C.

Example 8: Mutations at Positions that Interact with the Glycan Increase Rate of Conjugation at Gln295

Trastuzumab point mutants were constructed at positions at which the amino acid side chains contact the glycan, based on the hypothesis that removing protein-sugar contacts could increase local flexibility of the protein backbone to allow for conjugation at Gln295 without modifying the glycan. Phe241 and Phe243 make hydrophobic contacts with the glycan core, while Arg301 appears to make polar contacts to OH groups on Man or GlcNac sugars in different crystal structures of Fc domains. Trastuzumab variants were constructed in which one of these residues was mutated to alanine (F241A, F243A, R301A). The variants showed a more heterogeneous glycan profile, with several higher-MW glycans identified, as has been described previously for F241A and F243A (Ahmed et al., 2014, *J Mol Biol* 426(18): 3166-3179).

Reaction of the three variants with 3-APA MTG demonstrated that they were all modified efficiently under standard reaction conditions (Table 2).

Figure 6A:
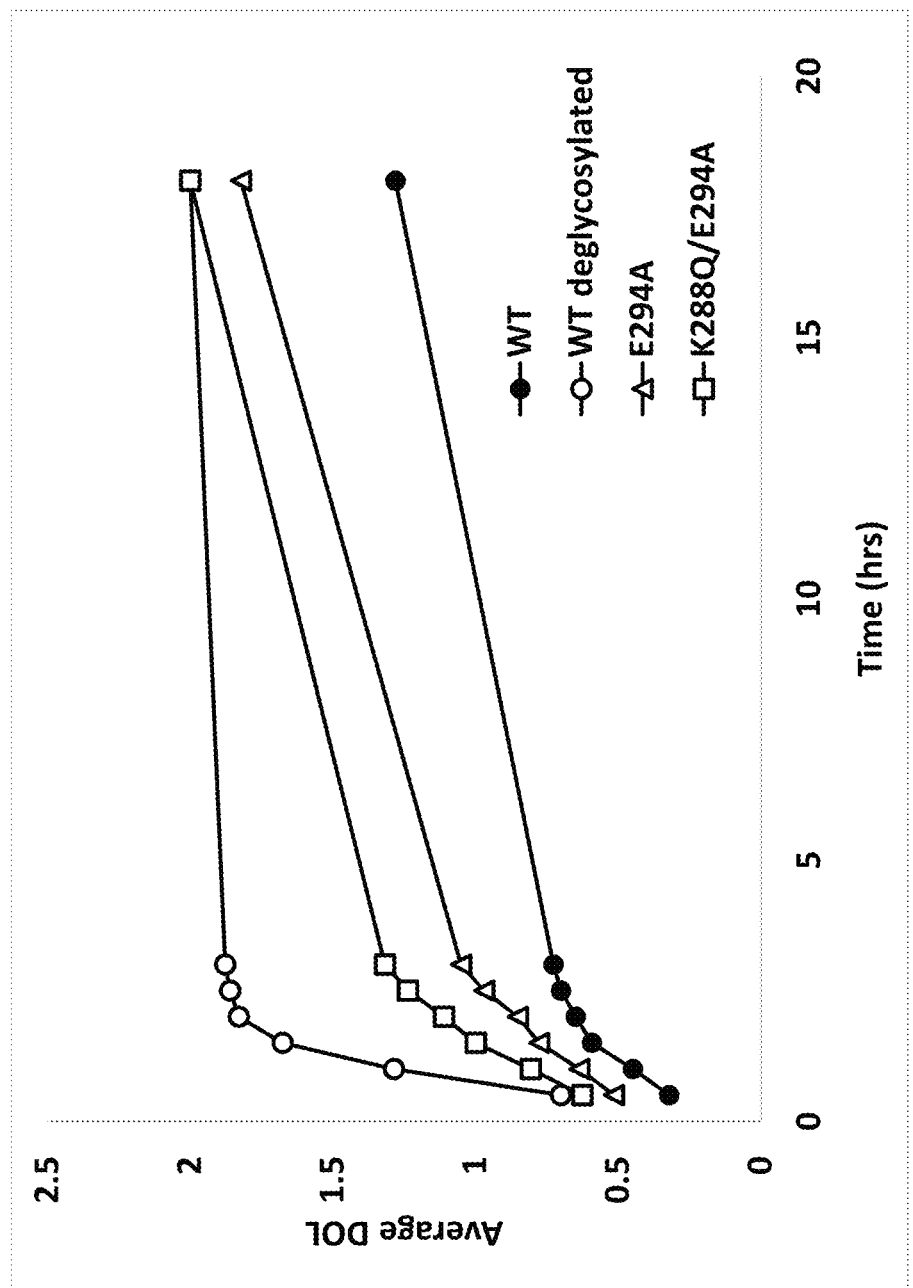
FIG. 6a shows the rate of MTG-catalyzed conjugation of 3-APA to trastuzumab variants; in particular, WT intact trastuzumab is compared to E294A and K288Q/E294A and deglycosylated WT trastuzumab, and the degree of labeling (DOL) is shown as a function of time.
Figure 6B:
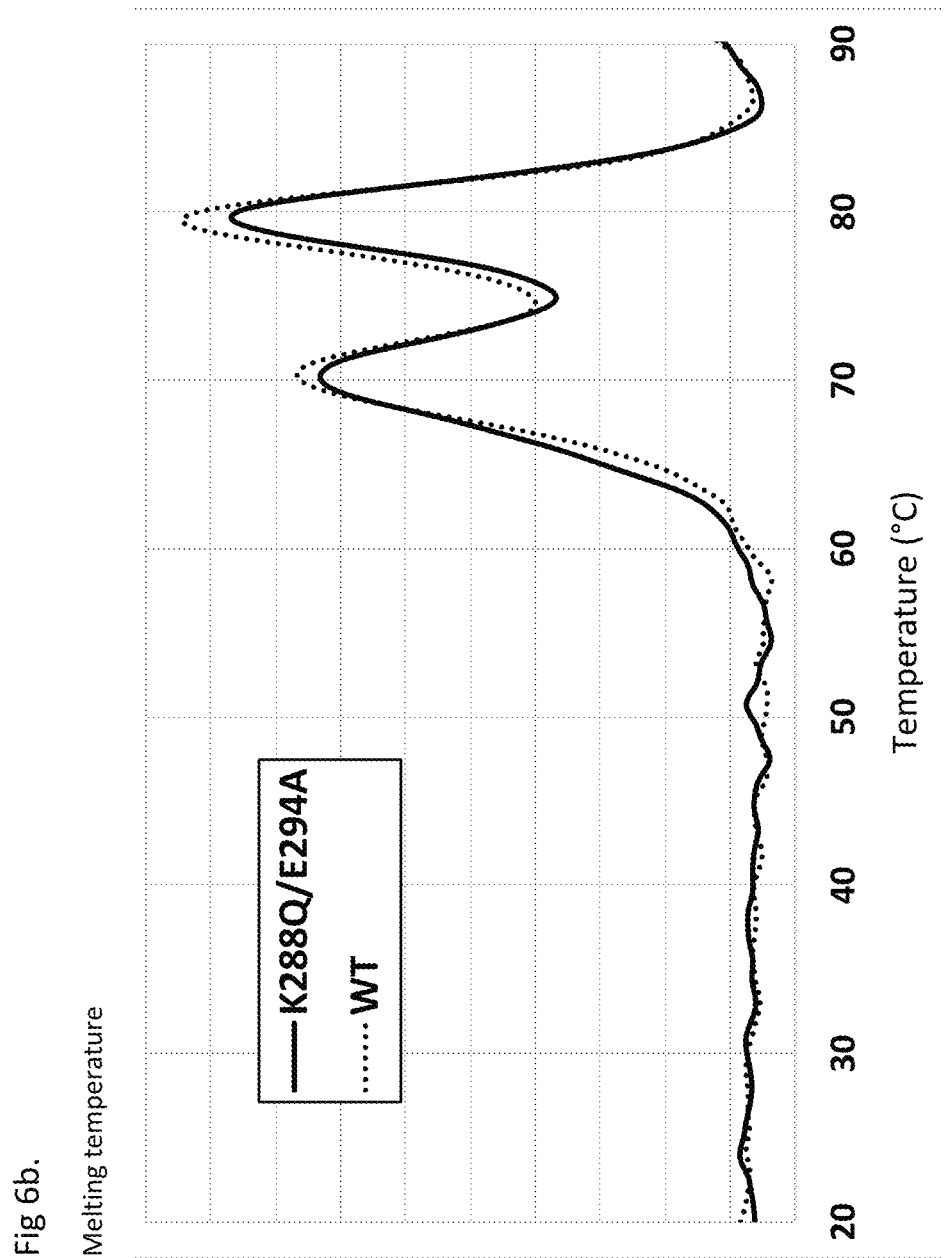
FIG. 6b shows the melting temperature (top graph) and aggregation temperature (bottom graph) of the K288Q/E294A variant compared to WT trastuzumab.
Figure 6B:
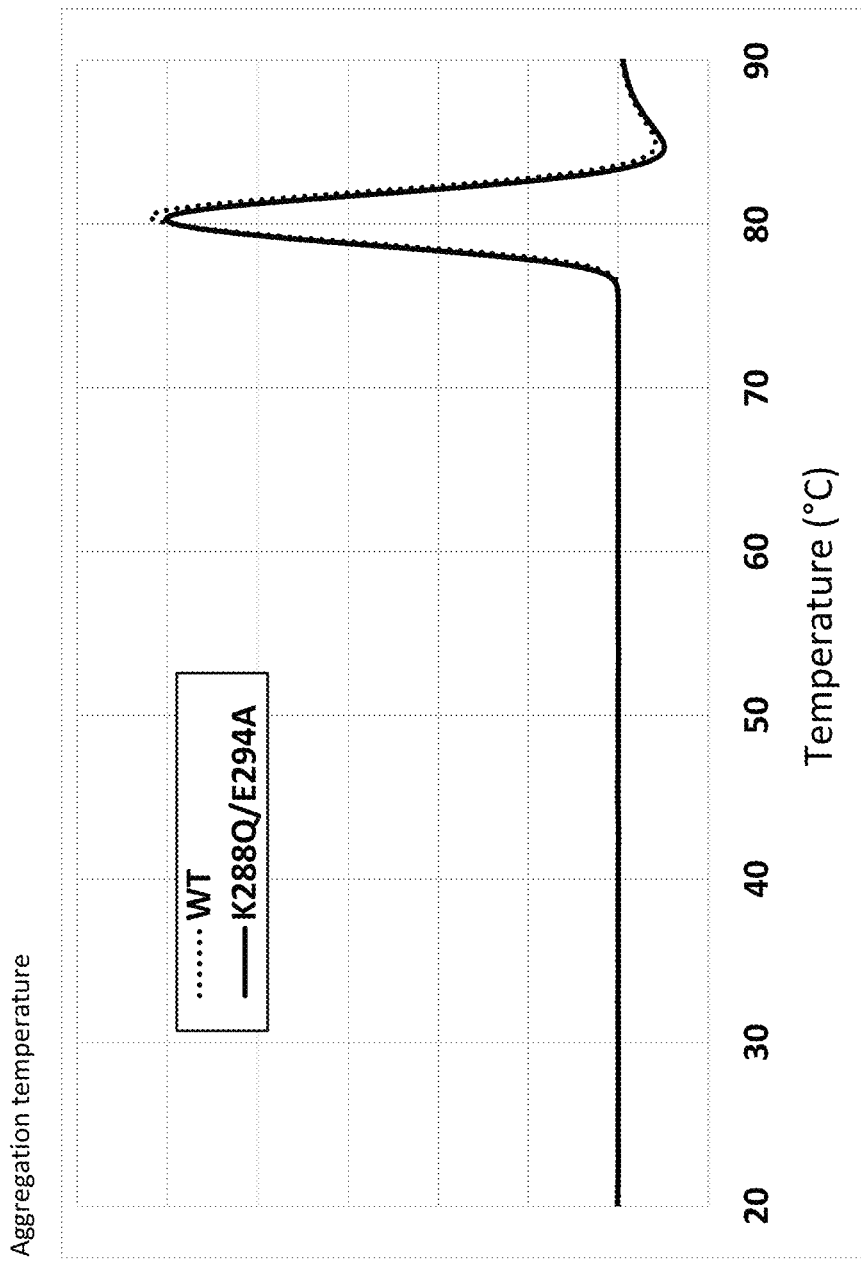

Example 9: Glu294Ala Variant Provides Increased Reaction Rate without Impact on Melting Temperature Glu294 is adjacent to Gln295, and in human IgG structures it forms a hydrogen bond to the side chain of His268. In an effort to increase access of Gln295 to MTG, Glu294 was mutated to Ala to disrupt the H-bond and increase flexibility of the structural element. Another variant was also evaluated that has the K288Q mutation in addition to E294A. The Glu294 variant showed ~1.5× increased reactivity with 3-APA and MTG under the standard reaction conditions described above (1 mg/mL mAb, 690 uM 3-APA, 10 U/mg Zedira MTG, PBS, 37° C.) and the K288Q/E294A was slightly faster, ~2× relative to the WT mAb (FIG. 6a). Both the E294A and K288Q/E294A variants reached or approached the full DAR=2 after overnight incubation while the WT mAb only reached a DAR of ~1.3. The Tm of the CH2 domain in the K288Q/E294A variant was evaluated by differential scanning fluorimetry and found to be essentially unchanged from the WT mAb (FIG. 6b). Thus these variants show similar biophysical properties to the WT mAb with increased reactivity toward MTG, making them of particular interest.

Figure 6C:
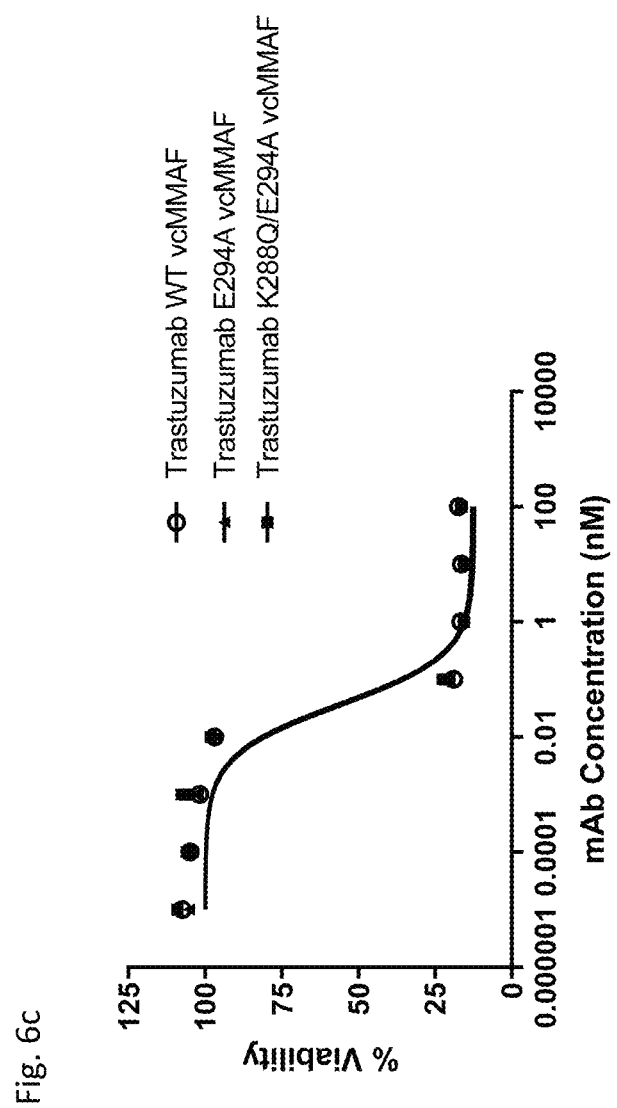
FIG. 6c shows a comparison of the activity of Trastuzumab-MMAF drug conjugates produced either with WT trastuzumab via established transglutaminase methods or using the glycan-intact E294A and K288Q/E294A variants. For all ADCs the drug payload is MMAF attached via a cleavable Val-Cit-PABC linker with DAR=2. SK-BR3 cells were treated with varying concentrations of conjugate for 72 hrs, and cell killing was determined by Cell Titer Glo assay.

An antibody-drug conjugate was constructed with the trastuzumab E294A and K288Q/E294A variants with the drug payload vcMMAF and compared to an ADC made with WT trastuzumab. mAbs were reacted with 3-APA and MTG to produce the azide-modified mAb, with prior deglycosylation with PNGase F in the case of the WT mAb and without deglycosylating for the E294A variant. The azido-mAbs were purified by protein A affinity chromatography and then reacted with DBCO-val-cit-MMAF to yield antibody drug conjugates with DAR=2. The ADCs along with relevant controls were evaluated in cell assays, and the activity was found to be similar regardless of conjugation method (FIG. 6c). SKBR3 cells, a cell line with high Her2 expression, were treated with varying concentrations of the ADCs for 72 hr at 37 C. Cell Titer Glo was used to determine cell viability at the conclusion of the treatment.

Example 10: Variants at Position 294 have a Range of Reactivities with MTG

Additional variants of trastuzumab were constructed with mutations at the Glu294 position: E294D, E294F, E294G, E294H, E294K, E294L, E294M, E294N, E294R, E294S, E294T, E294V, and E294Y. The reactivity of these variants with MTG was evaluated as well as the Tm/Tagg to compare their properties to the E294A variant. These variants were reacted with MTG and 3-APA under the standard conditions described above, and compared to WT mAb and deglycosylated WT mAb. Table 6 shows the (DOL) per mAb after incubation with TGase and 3-APA at 37 C. The DOL was determined by MS analysis of mAb heavy chains; no modification was observed on light chains. DOL is reported for the full mAb, which is 2× the DOL observed by MS of the heavy chain.

TABLE 6

Degree of labeling (DOL) of mAbs after incubation with MTG and 3-APA at 37° C. DOL is reported for the full mAb, which is 2x the DOL observed by MS of the heavy chain.

| SEQID | mutation | 1 hr | 4 hr | 18 hr | Tm1 | Tagg |
|---|---|---|---|---|---|---|
| 2 | WT | 0.5 | 0.7 | 1.3 | 69.9 | 77.8 |
| 2 | WT degly | 1.4 | 2.0 | 2.0 | | |
| 47 | E294D | 0.3 | 0.4 | 0.9 | 68.5 | 78 |
| 48 | E294F | 0.8 | 1.0 | 1.6 | 70.9 | 77.9 |
| 49 | E294G | 0.6 | 1.0 | 1.8 | 66.9 | 78.8 |
| 50 | E294H | 0.4 | 0.6 | 1.3 | 69.3 | 77.9 |
| 51 | E294K | 1.0 | 1.3 | 1.7 | 70.6 | 78.1 |
| 52 | E294L | 1.0 | 1.3 | 1.6 | 72.3 | 77.4 |
| 53 | E294M | 1.1 | 1.5 | 1.9 | 71.8 | 77.4 |
| 54 | E294N | 0.3 | 0.4 | 0.7 | 68.5 | 78.1 |
| 55 | E294R | 0.8 | 1.0 | 1.6 | 71.3 | 77.9 |
| 56 | E294S | 0.6 | 0.9 | 1.7 | 68.9 | 78.3 |
| 57 | E294T | 0.6 | 0.9 | 1.8 | 68.6 | 78 |
| 58 | E294V | 0.6 | 1.0 | 1.8 | 69.9 | 77.8 |
| 59 | E294Y | 0.8 | 1.2 | 1.8 | 71.3 | 77 |

Many of the variants have Tms similar to or even higher than the WT mAb (E294F, E294H, E294K, E294L, E294M, E294R, E294V, E294Y). Of these, several also show faster reaction with MTG than the WT mAb (E294F, E294K, E294L, E294M, E294R, E294V, and E294Y). In particular, the E294M variant stands out with Tm ~2° C. higher than the WT mAb and the highest DOL of any of the variants tested.

Example 11: YTE Mutations do not Increase Conjugation Rate

The triple mutant M252Y/S254T/T256E (YTE) increases affinity of IgGs to FcRn (Dall'Acqua et al., 2006, *J Biol Chem* 281(33):23514-23524). The YTE mutations are located in the CH2 domain, and they reduce the Tm of the CH2 domain by ~6.5° C. (Majumdar et al., 2015, *MAbs* 7(1):84-95). A trastuzumab variant with the YTE mutations was constructed and tested in the MTG reaction to determine if decreasing the thermal stability of the CH2 domain is sufficient to provide increased reactivity at position Gln295. The reaction rate of the YTE mutant was comparable to the WT mAb, demonstrating that it is the specific nature of the various mutations described herein, and not just CH2 domain destabilization, that provides enhanced reactivity.

Example 12: Characterization of V302A, V302S, and E294Q Variants in Different IgG Backgrounds A series of variants containing the mutations described above (V302A, V302S, E294Q, E294Q/V302A, and E294A) in different mAb backgrounds was constructed. Cetuximab is a clinically approved mouse-human IgG1 chimeric mAb that binds to EGFR. Panitumumab is a clinically approved human IgG2 mAb that binds to EGFR. Pertuzumab is a clinically approved human IgG1 mAb that binds to Her2. PSMB127 is a human IgG4 mAb that binds to prostate-specific membrane antigen (PSMA) described in WO2019224718A2. These variants were reacted with MTG and 3-APA under the standard conditions described above, and compared to the appropriate WT mAb and deglycosylated WT mAb. Table 7 shows the (DOL) per mAb after incubation with TGase and 3-APA at 37 C. The DOL was determined by MS analysis of mAb heavy chains; no modification was observed on light chains. DOL is reported for the full mAb, which is 2× the DOL observed by MS of the heavy chain.

TABLE 7

Degree of labeling (DOL) of mAbs after incubation with MTG and 3-APA at 37° C. DOL is reported for the full mAb, which is 2x the DOL observed by MS of the heavy chain.

| SEQID | description | 4 hr | 18 hr |
|---|---|---|---|
| 1/2 | Trastuzumab WT | | 1.2 |
| 1/2 | Trastuzumab WT deglycosylated | | 2.0 |
| 24 | Trastuzumab V302S | | 2.0 |
| 35 | Trastuzumab V302A | | 2.0 |
| 91 | Trastuzumab E294Q/V302A | | 4.0 |
| 42 | Trastuzumab E294Q | | 3.7 |
| 46 | Trastuzumab E294A | | 1.8 |
| 63/64 | Cetuximab WT | | 1.3 |
| 63/64 | Cetuximab WT deglycosylated | | 2.0 |
| 65 | Cetuximab V302S | | 2.0 |
| 66 | Cetuximab V302A | | 2.0 |
| 67 | Cetuximab E294Q/V302A | | 4.0 |
| 68 | Cetuximab E294Q | | 3.7 |
| 69 | Cetuximab E294A | | 1.9 |
| 70/71 | Panitumumab WT | | 1.2 |
| 70/71 | Panitumumab WT deglycosylated | | 2.0 |
| 72 | Panitumumab V302S | | 2.0 |
| 73 | Panitumumab V302A | | ND |
| 74 | Panitumumab E294Q/V302A | | 4.0 |
| 75 | Panitumumab E294Q | | 3.6 |
| 76 | Panitumumab E294A | | 1.7 |
| 77/78 | Pertuzumab WT | | 1.2 |
| 77/78 | Pertuzumab WT deglycosylated | | 2.0 |
| 79 | Pertuzumab V302S | | 2.0 |
| 80 | Pertuzumab V302A | | 2.0 |
| 81 | Pertuzumab E294Q/V302A | | 3.9 |
| 82 | Pertuzumab E294Q | | 3.7 |
| 83 | Pertuzumab E294A | | ND |
| 84/85 | PSMB127 WT | | 1.2 |
| 84/85 | PSMB127 WT deglycosylated | | 2.0 |
| 86 | PSMB127 V302S | | ND |
| 87 | PSMB127 V302A | | 2.0 |
| 88 | PSMB127 E294Q/V302A | | 3.9 |
| 89 | PSMB127 E294Q | | 3.6 |
| 90 | PSMB127 E294A | | 1.7 |

The mutations in this series of antibodies produced similar effects to the same mutations constructed in trastuzumab, demonstrating the broad applicability of this strategy to a variety of human antibodies and IgG isotypes. In addition, consistent with the observations in Example 6 above, many of the single (e.g. E294Q) and double (e.g. E294Q/V302A) mutants achieved a DAR=4 by completion of the antibody-payload conjugation assay, while retaining an intact glycan.

Example 13: Reaction of Variants with Different Amine Substrates

A series of amine-containing substrates was obtained for conjugation with MTG. An additional azide-containing amine with a short PEG linker; the biotin-linked amine pentylaminobiotin; and two MMAF-linked amines with cleavable or non-cleavable linkers. The substrates are described in Table 8:

TABLE 8

Amine substrates tested in MTG-catalyzed conjugations. Substrates were dissolved in the indicated solvent at 50 mM.

| Substrate | Manufacturer | Catalog # | MW | solvent |
|---|---|---|---|---|
| 3-Azidopropylamine | Click Chemistry Tools | AZ115 | 100 | water |
| Azido-PEG3-amine | Click Chemistry Tools | AZ101 | 218 | water |
| Pentylamino biotin | ThermoFisher | 21345 | 328 | water |
| NH2-PEG4-MMAF | Levena Biopharma | custom | 979 | DMSO |
| NH2-PEG4-Val-Cit-PABC-MMAF | Levena Biopharma | custom | 1386 | DMSO |

The substrates were reacted with WT trastuzumab and the variants V302S, E294M, E294Q/Q295A, and E294Q/V302A.

Components were combined in a reaction mixture with the final concentrations of antibody at 1 mg/mL, substrate at 690 uM, and Zedira MTG at 10 U/mg, in PBS. Reactions were incubated at 37° C. for 18 hours. For analysis, MTG was inactivated by the addition of MTG blocker and mAbs were deglycosylated with Rapid PNGase F (1% v/v) for 20 min at 50° C. and reduced with DTT to 20 mM followed by LC-MS to determine DOL.

In general, the substrate selectivity observed with the WT deglycosylated mAb was similar to the variants (Table 9). The 3-APA, azido-PEG3-amine, and pentylamino biotin reactions went essentially to completion for all of the variants tested. Reactions with the MMAF molecules showed more variability. In most cases the NH2-vcMMAF reactions gave higher DOLs than the NH2-MMAF, with the exception of the E294Q/Q295A variant. The V302S variant, meanwhile, had comparable reactivity to deglycosylated WT with NH2-vcMMAF but very little reaction was observed with NH2-MMAF.

TABLE 9

DOL after 18 hour reaction at 37° C. DOL is reported for the full mAb, which is 2x the DOL observed by MS of the heavy chain.

| Substrate | WT | WT degly | E294M | V302S | E294Q Q295A | E294Q V302A |
|---|---|---|---|---|---|---|
| 3-APA | 1.2 | 1.9 | 1.9 | 2.0 | 2 | 3.8 |
| Azido-PEG3-amine | 1.2 | 2.0 | 1.8 | 1.9 | 1.8 | 3.7 |
| pentyl amino biotin | 1.1 | 2.0 | 1.8 | 2 | 1.8 | 3.8 |
| NH2-MMAF | 0.1 | 0.9 | 0.4 | 0.2 | 1.3 | 1.8 |
| NH2-vcMMAF | 0.5 | 1.7 | 0.9 | 1.6 | 1.0 | 3.2 |

The embodiments of the invention are intended to be merely exemplary, and those skilled in the art will recognize, or be able to ascertain using no more than routine experimentation, numerous equivalents to the specific procedures of the invention. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

SEQUENCES

| SEQ ID NO | Description | Sequence |
|---|---|---|
| 1 | Trastuzumab light chain | DIQMTQSPSSLSASVGDRVTITCRASQDVNTAVAWYQQK PGKAPKLLIYSASFLYSGVPSRFSGSRSGTDFTLTISSLQPE DFATYYCQQHYTTPPTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |
| 2 | Trastuzumab heavy chain | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 3 | K288Q | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 4 | K288Q/P291A/R292P | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT |

-continued

| SEQ ID NO | Description | Sequence |
|---|---|---|
|  |  | VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKAPEEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 5 | K288Q/Y300L/ V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKPREEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 6 | K288Q/P291A/ R292P/Y300L/ V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKAPEEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 7 | K288Q/K290H | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTHPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 8 | K288Q/V305E | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKPREEQYNSTYRVVSELTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 9 | K288Q/E258K | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG |

| SEQ ID NO | Description | Sequence |
|---|---|---|
| | | GPSVFLFPPKPKDTLMISRTPKVTCVVVDVSHEDPEVKFN WYVDGVEVHNAQTKPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 10 | K288Q/K290H/ V305E | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTHPREEQYNSTYRVVSELTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 11 | K288Q/K290H/ V305E/E258K | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPKVTCVVVDVSHEDPEVKFN WYVDGVEVHNAQTHPREEQYNSTYRVVSELTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 12 | C'/D strand | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHTAQTHAPEKQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 13 | C'/D-E strands | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHTAQTHAPEKQSNSTLRSVSELPVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 14 | C'/D-E strands + E258K | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPKVTCVVVDVSHEDPEVKFN WYVDGVEVHTAQTHAPEKQSNSTLRSVSELPVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPGK |

SEQUENCES

| SEQ ID NO | Description | Sequence |
|---|---|---|
| 15 | K288Q + PR→AP; YRV→LRS; K290H, V305E, E258K | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPKVTCVVVDVSHEDPEVKFN WYVDGVEVHNAQTHAPEEQYNSTLRSVSELTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 16 | Graft entire CH2 domain | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GSSVFIFPPKTKDVLTITLTPKVTCVVVDISQNDPEVRFSWF IDDVEVHTAQTHAPEKQSNSTLRSVSELPIVHRDWLNGKT FKCKVNSGAFPAPIEKSISKPEGQPREPQVYTLPPSRDELTK NQVSLTCLVKGFYPSDIAVEWESNGQPENNYKTTPPVLDS DGSFFLYSKLTVDKSRWQQGNVFSCSVMHEALHNHYTQK SLSLSPGK |
| 17 | R301A | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTYAVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 18 | F241A | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVALFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 19 | F243A | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLAPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 20 | K288Q/Y300L | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKPREEQYNSTLRVVSVLTVLHQDWL |

SEQUENCES

| SEQ ID NO | Description | Sequence |
|---|---|---|
| | | NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 21 | K288Q/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKPREEQYNSTYRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 22 | Y300L/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 23 | Y300L | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTLRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 24 | V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTYRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 25 | K288Q/E294A | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAQTKPREAQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 26 | H285Q/Y300L/ V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT |

| SEQ ID NO | Description | Sequence |
|---|---|---|
| 27 | N286Q/Y300L/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHQAKTKPREEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 28 | A287Q/Y300L/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNQKTKPREEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 29 | T289Q/Y300L/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKQKPREEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 30 | K290Q/Y300L/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTQPREEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 31 | R292Q/Y300L/V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPQEEQYNSTLRSVSVLTVLHQDWL |

| SEQ ID NO | Description | Sequence |
|---|---|---|
| | | NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 32 | E293Q/Y300L/ V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPRQEQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 33 | E294Q/Y300L/ V302S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQQYNSTLRSVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 34 | K288Q YTE | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLYITREPEVTCVVVDVSHEDPEVKFNW YVDGVEVHNAQTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 35 | V302A | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPREEQYNSTYR<u>A</u>VSVLTV LHQDWLNGKEYKCKVSNKALPAPIEKTISKA<u>K</u>GQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 36 | V302I | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPREEQYNSTYR<u>I</u>VSVLTV LHQDWLNGKEYKCKVSNKALPAPIEKTISKA<u>K</u>GQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 37 | V302L | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT |

| SEQ ID NO | Description | Sequence |
|---|---|---|
| | | LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRLVSVLTV<br>LHQDWLNGKEYKCKVSNKALPAPIEKTISKAKGQPREPQ<br>VYTLPPSRDELTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| 38 | V302M | EVQLVESGGGLVQPGGSLRLSCAASGFNIKDTYIHWVRQ<br>APGKGLEWVARIYPTNGYTRYADSVKGRFTISADTSKNT<br>AYLQMNSLRAEDTAVYYCSRWGGDGFYAMDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRMVSVLT<br>VLHQDWLNGKEYKCKVSNKALPAPIEKTISKAKGQPREP<br>QVYTLPPSRDELTKNQVSLTCLVKGFYPSDIAVEWESNG<br>QPENNYKTTPPVLDSDGSFFLYSKLTVDKSRWQQGNVFS<br>CSVMHEALHNHYTQKSLSLSPGK |
| 39 | V302T | EVQLVESGGGLVQPGGSLRLSCAASGFNIKDTYIHWVRQ<br>APGKGLEWVARIYPTNGYTRYADSVKGRFTISADTSKNT<br>AYLQMNSLRAEDTAVYYCSRWGGDGFYAMDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRTVSVLTV<br>LHQDWLNGKEYKCKVSNKALPAPIEKTISKAKGQPREPQ<br>VYTLPPSRDELTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| 40 | V302F | EVQLVESGGGLVQPGGSLRLSCAASGFNIKDTYIHWVRQ<br>APGKGLEWVARIYPTNGYTRYADSVKGRFTISADTSKNT<br>AYLQMNSLRAEDTAVYYCSRWGGDGFYAMDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRFVSVLTV<br>LHQDWLNGKEYKCKVSNKALPAPIEKTISKAKGQPREPQ<br>VYTLPPSRDELTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| 41 | V302Y | EVQLVESGGGLVQPGGSLRLSCAASGFNIKDTYIHWVRQ<br>APGKGLEWVARIYPTNGYTRYADSVKGRFTISADTSKNT<br>AYLQMNSLRAEDTAVYYCSRWGGDGFYAMDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRYVSVLTV<br>LHQDWLNGKEYKCKVSNKALPAPIEKTISKAKGQPREPQ<br>VYTLPPSRDELTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| 42 | E294Q | EVQLVESGGGLVQPGGSLRLSCAASGFNIKDTYIHWVRQ<br>APGKGLEWVARIYPTNGYTRYADSVKGRFTISADTSKNT<br>AYLQMNSLRAEDTAVYYCSRWGGDGFYAMDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP |

| SEQ ID NO | Description | Sequence |
|---|---|---|
| | | APELLGGPSVFLFPPKPKDTLMISRTPEVTCVVVDVSHED PEVKFNWYVDGVEVHNAKTKPREQQYNSTYRVVSVLT VLHQDWLNGKEYKCKVSNKALPAPIEKTISKAKGQPREP QVYTLPPSRDELTKNQVSLTCLVKGFYPSDIAVEWESNG QPENNYKTTPPVLDSDGSFFLYSKLTVDKSRWQQGNVFS CSVMHEALHNHYTQKSLSLSPGK |
| 43 | E293Q | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPRQEQYNSTYRVVSVLT VLHQDWLNGKEYKCKVSNKALPAPIEKTISKAKGQPREP QVYTLPPSRDELTKNQVSLTCLVKGFYPSDIAVEWESNG QPENNYKTTPPVLDSDGSFFLYSKLTVDKSRWQQGNVFS CSVMHEALHNHYTQKSLSLSPGK |
| 44 | V302S/E294Q | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPREQQYNSTYRSVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 45 | V302S/E293Q | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPRQEQYNSTYRSVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 46 | E294A | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPREAQYNSTYRVVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 47 | E294D | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREDQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |

| SEQ ID NO | Description | Sequence |
|---|---|---|
| 48 | E294F | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREFQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 49 | E294G | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREGQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 50 | E294H | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREHQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 51 | E294K | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREKQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 52 | E294L | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPRELQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 53 | E294M | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREMQYNSTYRVVSVLTVLHQDW |

| SEQ ID NO | Description | Sequence |
|---|---|---|
| | | LNGKEYKCKVSNKALPAPIEKTISKAKGQPREPQVYTLPPS RDELTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 54 | E294N | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPRENQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 55 | E294R | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPRERQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 56 | E294S | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPRESQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 57 | E294T | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPRETQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 58 | E294V | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREVQYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 59 | E294Y | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT |

SEQUENCES

| SEQ ID NO | Description | Sequence |
|---|---|---|
| | | VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREYQNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 60 | E294Q/Q295A | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQAYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 61 | E294Q/Q295E | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQEYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 62 | E294Q/Q295N | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQNYNSTYRVVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 63 | Cetuximab LC | DILLTQSPVILSVSPGERVSFSCRASQSIGTNIHWYQQRTN GSPRLLIKYASESISGIPSRFSGSGSGTDFTLSINSVESEDIA DYYCQQNNNWPTTFGAGTKLELKRTVAAPSVFIFPPSDE QLKSGTASVVCLLNNFYPREAKVQWKVDNALQSGNSQE SVTEQDSKDSTYSLSSTLTLSKADYEKHKVYACEVTHQG LSSPVTKSFNRGEC |
| 64 | Cetuximab HC | QVQLKQSGPGLVQPSQSLSITCTVSGFSLTNYGVHWVRQS PGKGLEWLGVIWSGGNTDYNTPFTSRLSINKDNSKSQVFF KMNSLQSNDTAIYYCARALTYYDYEFAYWGQGTLVTVSA ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 65 | Cetuximab V302S | QVQLKQSGPGLVQPSQSLSITCTVSGFSLTNYGVHWVRQS PGKGLEWLGVIWSGGNTDYNTPFTSRLSINKDNSKSQVFF KMNSLQSNDTAIYYCARALTYYDYEFAYWGQGTLVTVSA ASTKGPSVFPLAPSSKSTSGGTAALGCLVKDYFPEPVTVS |

| SEQ ID NO | Description | Sequence |
|---|---|---|
| | | WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRSVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 66 | Cetuximab V302A | QVQLKQSGPGLVQPSQSLSITCTVSGFSLTNYGVHWVRQ SPGKGLEWLGVIWSGGNTDYNTPFTSRLSINKDNSKSQV FFKMNSLQSNDTAIYYCARALTYYDYEFAYWGQGTLVT VSAASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKRVEPKSCDKTHTCPPCPAPE LLGGPSVFLFPPKPKDTLMISRTPEVTCVVVDVSHEDPEV KFNWYVDGVEVHNAKTKPREEQYNSTYRAVSVLTVLH QDWLNGKEYKCKVSNKALPAPIEKTISKAKGQPREPQVY TLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGK |
| 67 | Cetuximab E294Q/V302A | QVQLKQSGPGLVQPSQSLSITCTVSGFSLTNYGVHWVRQS PGKGLEWLGVIWSGGNTDYNTPFTSRLSINKDNSKSQVFF KMNSLQSNDTAIYYCARALTYYDYEFAYWGQGTLVTVSA ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREQQYNSTYRAVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 68 | Cetuximab E294Q | QVQLKQSGPGLVQPSQSLSITCTVSGFSLTNYGVHWVRQS PGKGLEWLGVIWSGGNTDYNTPFTSRLSINKDNSKSQVFF KMNSLQSNDTAIYYCARALTYYDYEFAYWGQGTLVTVSA ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREQQYNSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 69 | Cetuximab E294A | QVQLKQSGPGLVQPSQSLSITCTVSGFSLTNYGVHWVRQS PGKGLEWLGVIWSGGNTDYNTPFTSRLSINKDNSKSQVFF KMNSLQSNDTAIYYCARALTYYDYEFAYWGQGTLVTVSA ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREAQYNSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 70 | Panitumumab LC | DIQMTQSPSSLSASVGDRVTITCQASQDISNYLNWYQQKP GKAPKLLIYDASNLETGVPSRFSGSGSGTDFTFTISSLQPE DIATYFCQHFDHLPLAFGGGTKVEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQ GLSSPVTKSFNRGEC |
| 71 | Panitumumab HC | QVQLQESGPGLVKPSETLSLTCTVSGGSVSSGDYYWTWIR QSPGKGLEWIGHIYYSGNTNYNPSLKSRLTISIDTSKTQFSL KLSSVTAADTAIYYCVRDRVTGAFDIWGQGTMVTVSSAS TKGPSVFPLAPCSRSTSESTAALGCLVKDYFPEPVTVSWNS GALTSGVHTFPAVLQSSGLYSLSSVVTVPSSNFGTQTYTCN |

| SEQ ID NO | Description | Sequence |
|---|---|---|
| | | VDHKPSNTKVDKTVERKCCVECPPCPAPPVAGPSVFLFPP<br>KPKDTLMISRTPEVTCVVVDVSHEDPEVQFNWYVDGVEV<br>HNAKTKPREEQFNSTFRVVSVLTVVHQDWLNGKEYKCKV<br>SNKGLPAPIEKTISKTKGQPREPQVYTLPPSREEMTKNQVS<br>LTCLVKGFYPSDIAVEWESNGQPENNYKTTPPMLDSDGSF<br>FLYSKLTVDKSRWQQGNVFSCSVMHEALHNHYTQKSLSL<br>SPGK |
| 72 | Panitumumab V302S | QVQLQESGPGLVKPSETLSLTCTVSGGSVSSGDYYWTWI<br>RQSPGKGLEWIGHIYYSGNTNYNPSLKSRLTISIDTSKTQF<br>SLKLSSVTAADTAIYYCVRDRVTGAFDIWGQGTMVTVSS<br>ASTKGPSVFPLAPCSRSTSESTAALGCLVKDYFPEPVTVS<br>WNSGALTSGVHTFPAVLQSSGLYSLSSVVTVPSSNFGTQT<br>YTCNVDHKPSNTKVDKTVERKCCVECPPCPAPPVAGPSV<br>FLFPPKPKDTLMISRTPEVTCVVVDVSHEDPEVQFNWYV<br>DGVEVHNAKTKPREEQFNSTFRSVSVLTVVHQDWLNGK<br>EYKCKVSNKGLPAPIEKTISKTKGQPREPQVYTLPPSREE<br>MTKNQVSLTCLVKGFYPSDIAVEWESNGQPENNYKTTPP<br>MLDSDGSFFLYSKLTVDKSRWQQGNVFSCSVMHEALHN<br>HYTQKSLSLSPGK |
| 73 | Panitumumab V302A | QVQLQESGPGLVKPSETLSLTCTVSGGSVSSGDYYWTWIR<br>QSPGKGLEWIGHIYYSGNTNYNPSLKSRLTISIDTSKTQFSL<br>KLSSVTAADTAIYYCVRDRVTGAFDIWGQGTMVTVSSAS<br>TKGPSVFPLAPCSRSTSESTAALGCLVKDYFPEPVTVSWNS<br>GALTSGVHTFPAVLQSSGLYSLSSVVTVPSSNFGTQTYTCN<br>VDHKPSNTKVDKTVERKCCVECPPCPAPPVAGPSVFLFPP<br>KPKDTLMISRTPEVTCVVVDVSHEDPEVQFNWYVDGVEV<br>HNAKTKPREEQFNSTFRAVSVLTVVHQDWLNGKEYKCKV<br>SNKGLPAPIEKTISKTKGQPREPQVYTLPPSREEMTKNQVS<br>LTCLVKGFYPSDIAVEWESNGQPENNYKTTPPMLDSDGSF<br>FLYSKLTVDKSRWQQGNVFSCSVMHEALHNHYTQKSLSL<br>SPGK |
| 74 | Panitumumab E294Q/V302A | QVQLQESGPGLVKPSETLSLTCTVSGGSVSSGDYYWTWIR<br>QSPGKGLEWIGHIYYSGNTNYNPSLKSRLTISIDTSKTQFSL<br>KLSSVTAADTAIYYCVRDRVTGAFDIWGQGTMVTVSSAS<br>TKGPSVFPLAPCSRSTSESTAALGCLVKDYFPEPVTVSWNS<br>GALTSGVHTFPAVLQSSGLYSLSSVVTVPSSNFGTQTYTCN<br>VDHKPSNTKVDKTVERKCCVECPPCPAPPVAGPSVFLFPP<br>KPKDTLMISRTPEVTCVVVDVSHEDPEVQFNWYVDGVEV<br>HNAKTKPREQQFNSTFRAVSVLTVVHQDWLNGKEYKCK<br>VSNKGLPAPIEKTISKTKGQPREPQVYTLPPSREEMTKNQV<br>SLTCLVKGFYPSDIAVEWESNGQPENNYKTTPPMLDSDGS<br>FFLYSKLTVDKSRWQQGNVFSCSVMHEALHNHYTQKSLS<br>LSPGK |
| 75 | Panitumumab E294Q | QVQLQESGPGLVKPSETLSLTCTVSGGSVSSGDYYWTWIR<br>QSPGKGLEWIGHIYYSGNTNYNPSLKSRLTISIDTSKTQFSL<br>KLSSVTAADTAIYYCVRDRVTGAFDIWGQGTMVTVSSAS<br>TKGPSVFPLAPCSRSTSESTAALGCLVKDYFPEPVTVSWNS<br>GALTSGVHTFPAVLQSSGLYSLSSVVTVPSSNFGTQTYTCN<br>VDHKPSNTKVDKTVERKCCVECPPCPAPPVAGPSVFLFPP<br>KPKDTLMISRTPEVTCVVVDVSHEDPEVQFNWYVDGVEV<br>HNAKTKPREQQFNSTFRVVSVLTVVHQDWLNGKEYKCK<br>VSNKGLPAPIEKTISKTKGQPREPQVYTLPPSREEMTKNQV<br>SLTCLVKGFYPSDIAVEWESNGQPENNYKTTPPMLDSDGS<br>FFLYSKLTVDKSRWQQGNVFSCSVMHEALHNHYTQKSLS<br>LSPGK |
| 76 | Panitumumab E294A | QVQLQESGPGLVKPSETLSLTCTVSGGSVSSGDYYWTWIR<br>QSPGKGLEWIGHIYYSGNTNYNPSLKSRLTISIDTSKTQFSL<br>KLSSVTAADTAIYYCVRDRVTGAFDIWGQGTMVTVSSAS<br>TKGPSVFPLAPCSRSTSESTAALGCLVKDYFPEPVTVSWNS<br>GALTSGVHTFPAVLQSSGLYSLSSVVTVPSSNFGTQTYTCN<br>VDHKPSNTKVDKTVERKCCVECPPCPAPPVAGPSVFLFPP<br>KPKDTLMISRTPEVTCVVVDVSHEDPEVQFNWYVDGVEV<br>HNAKTKPREAQFNSTFRVVSVLTVVHQDWLNGKEYKCK<br>VSNKGLPAPIEKTISKTKGQPREPQVYTLPPSREEMTKNQV<br>SLTCLVKGFYPSDIAVEWESNGQPENNYKTTPPMLDSDGS<br>FFLYSKLTVDKSRWQQGNVFSCSVMHEALHNHYTQKSLS<br>LSPGK |

| SEQ ID NO | Description | Sequence |
|---|---|---|
| 77 | Pertuzumab LC | DIQMTQSPSSLSASVGDRVTITCKASQDVSIGVAWYQQK PGKAPKLLIYSASYRYTGVPSRFSGSGSGTDFTLTISSLQP EDFATYYCQQYYIYPYTFGQGTKVEIKRTVAAPSVFIFPP SDEQLKSGTASVVCLLNNFYPREAKVQWKVDNALQSGN SQESVTEQDSKDSTYSLSSTLTLSKADYEKHKVYACEVT HQGLSSPVTKSFNRGEC |
| 78 | Pertuzumab HC | EVQLVESGGGLVQPGGSLRLSCAASGFTFTDYTMDWVR QAPGKGLEWVADVNPNSGGSIYNQRFKGRFTLSVDRSK NTLYLQMNSLRAEDTAVYYCARNLGPSFYFDYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTVL HQDWLNGKEYKCKVSNKALPAPIEKTISKAKGQPREPQV YTLPPSREEMTKNQVSLTCLVKGFYPSDIAVEWESNGQP ENNYKTTPPVLDSDGSFFLYSKLTVDKSRWQQGNVFSCS VMHEALHNHYTQKSLSLSPG |
| 79 | Pertuzumab V302S | EVQLVESGGGLVQPGGSLRLSCAASGFTFTDYTMDWVRQ APGKGLEWVADVNPNSGGSIYNQRFKGRFTLSVDRSKNT LYLQMNSLRAEDTAVYYCARNLGPSFYFDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTYRSVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPG |
| 80 | Pertuzumab V302A | EVQLVESGGGLVQPGGSLRLSCAASGFTFTDYTMDWVRQ APGKGLEWVADVNPNSGGSIYNQRFKGRFTLSVDRSKNT LYLQMNSLRAEDTAVYYCARNLGPSFYFDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTYRAVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPG |
| 81 | Pertuzumab E294Q/V302A | EVQLVESGGGLVQPGGSLRLSCAASGFTFTDYTMDWVRQ APGKGLEWVADVNPNSGGSIYNQRFKGRFTLSVDRSKNT LYLQMNSLRAEDTAVYYCARNLGPSFYFDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQQYNSTYRAVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPG |
| 82 | Pertuzumab E294Q | EVQLVESGGGLVQPGGSLRLSCAASGFTFTDYTMDWVRQ APGKGLEWVADVNPNSGGSIYNQRFKGRFTLSVDRSKNT LYLQMNSLRAEDTAVYYCARNLGPSFYFDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQYNSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPG |

| SEQ ID NO | Description | Sequence |
|---|---|---|
| 83 | Pertuzumab E294A | EVQLVESGGGLVQPGGSLRLSCAASGFTFTDYTMDWVRQ APGKGLEWVADVNPNSGGSIYNQRFKGRFTLSVDRSKNT LYLQMNSLRAEDTAVYYCARNLGPSFYFDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREAQYNSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPG |
| 84 | PSMB127 LC | EIVLTQSPATLSLSPGERATLSCRASQSVSSYLAWYQQKP GQAPRLLIYDASNRATGIPARFSGSGSGTDFTLTISSLEPE DFAVYYCQQRSNWPLTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |
| 85 | PSMB127 HC | EVQLLESGGGLVQPGGSLRLSCAASGFTFKSDAMHWVRQ APGKGLEWVSEISGSGGYTNYADSVKGRFTISRDNSKNTL YLQMNSLRAEDTAVYYCARDSYDSSLYVGDYFDYWGQG TLVTVSSASTKGPSVFPLAPCSRSTSESTAALGCLVKDYFP EPVTVSWNSGALTSGVHTFPAVLQSSGLYSLSSVVTVPSSS LGTKTYTCNVDHKPSNTKVDKRVESKYGPPCPPCPAPEAA GGPSVFLFPPKPKDTLMISRTPEVTCVVVDVSQEDPEVQFN WYVDGVEVHNAKTKPREEQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK |
| 86 | PSMB127 V302S | EVQLLESGGGLVQPGGSLRLSCAASGFTFKSDAMHWVRQ APGKGLEWVSEISGSGGYTNYADSVKGRFTISRDNSKNTL YLQMNSLRAEDTAVYYCARDSYDSSLYVGDYFDYWGQG TLVTVSSASTKGPSVFPLAPCSRSTSESTAALGCLVKDYFP EPVTVSWNSGALTSGVHTFPAVLQSSGLYSLSSVVTVPSSS LGTKTYTCNVDHKPSNTKVDKRVESKYGPPCPPCPAPEAA GGPSVFLFPPKPKDTLMISRTPEVTCVVVDVSQEDPEVQFN WYVDGVEVHNAKTKPREEQFNSTYRSVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK |
| 87 | PSMB127 V302A | EVQLLESGGGLVQPGGSLRLSCAASGFTFKSDAMHWVRQ APGKGLEWVSEISGSGGYTNYADSVKGRFTISRDNSKNTL YLQMNSLRAEDTAVYYCARDSYDSSLYVGDYFDYWGQG TLVTVSSASTKGPSVFPLAPCSRSTSESTAALGCLVKDYFP EPVTVSWNSGALTSGVHTFPAVLQSSGLYSLSSVVTVPSSS LGTKTYTCNVDHKPSNTKVDKRVESKYGPPCPPCPAPEAA GGPSVFLFPPKPKDTLMISRTPEVTCVVVDVSQEDPEVQFN WYVDGVEVHNAKTKPREEQFNSTYRAVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK |
| 88 | PSMB127 E294Q/V302A | EVQLLESGGGLVQPGGSLRLSCAASGFTFKSDAMHWVR QAPGKGLEWVSEISGSGGYTNYADSVKGRFTISRDNSKN TLYLQMNSLRAEDTAVYYCARDSYDSSLYVGDYFDYW GQGTLVTVSSASTKGPSVFPLAPCSRSTSESTAALGCLVK DYFPEPVTVSWNSGALTSGVHTFPAVLQSSGLYSLSSVVT VPSSSLGTKTYTCNVDHKPSNTKVDKRVESKYGPPCPPC PAPEAAGGPSVFLFPPKPKDTLMISRTPEVTCVVVDVSQE DPEVQFNWYVDGVEVHNAKTKPREQQFNSTYRAVSVLT VLHQDWLNGKEYKCKVSNKGLPSSIEKTISKAKGQPREP QVYTLPPSQEEMTKNQVSLTCLVKGFYPSDIAVEWESNG QPENNYKTTPPVLDSDGSFFLYSRLTVDKSRWQEGNVFS CSVMHEALHNHYTQKSLSLSLGK |

SEQUENCES

| SEQ ID NO | Description | Sequence |
|---|---|---|
| 89 | PSMB127 E294Q | EVQLLESGGGLVQPGGSLRLSCAASGFTFKSDAMHWVRQ APGKGLEWVSEISGSGGYTNYADSVKGRFTISRDNSKNTL YLQMNSLRAEDTAVYYCARDSYDSSLYVGDYFDYWGQG TLVTVSSASTKGPSVFPLAPCSRSTSESTAALGCLVKDYFP EPVTVSWNSGALTSGVHTFPAVLQSSGLYSLSSVVTVPSSS LGTKTYTCNVDHKPSNTKVDKRVESKYGPPCPPCPAPEAA GGPSVFLFPPKPKDTLMISRTPEVTCVVVDVSQEDPEVQFN WYVDGVEVHNAKTKPREQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK |
| 90 | PSMB127 E294A | EVQLLESGGGLVQPGGSLRLSCAASGFTFKSDAMHWVRQ APGKGLEWVSEISGSGGYTNYADSVKGRFTISRDNSKNTL YLQMNSLRAEDTAVYYCARDSYDSSLYVGDYFDYWGQG TLVTVSSASTKGPSVFPLAPCSRSTSESTAALGCLVKDYFP EPVTVSWNSGALTSGVHTFPAVLQSSGLYSLSSVVTVPSSS LGTKTYTCNVDHKPSNTKVDKRVESKYGPPCPPCPAPEAA GGPSVFLFPPKPKDTLMISRTPEVTCVVVDVSQEDPEVQFN WYVDGVEVHNAKTKPREAQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK |
| 91 | Trastuzumab HC E294Q/V302A | EVQLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREQYNSTYRAVSVLTVLHQDWL NGKEYKCKVSNKALPAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPGK |

We claim:

1. An engineered monoclonal antibody comprising an amino acid substitution at heavy chain position 302 of the antibody, a glutamine substitution at heavy chain position 286, 287, 288, 289, 290, 293 or 294, and/or an alanine substitution at heavy chain position 241, 243, 294 or 301, and an endogenous heavy chain Q295 residue, wherein the engineered monoclonal antibody is non-deglycosylated, the substitution at heavy chain position 302 is V302S, V302A or V302T, and wherein the engineered monoclonal antibody further comprises the amino acid substitution Y300L at heavy chain position 300, and the amino acid numbering is according to the EU Index of Kabat.

2. The engineered antibody of claim 1, wherein the amino acid substitution at heavy chain position 302 is V302A.

3. The engineered antibody of claim 1, wherein the amino acid substitution at heavy chain position 302 is V302S.

4. The engineered antibody of claim 1, comprising the glutamine substitution at heavy chain position 294.

5. The engineered antibody of claim 1, wherein the antibody is a human IgG antibody.

6. The engineered antibody of claim 5, wherein the antibody is a human IgG1 antibody.

7. The engineered antibody of claim 5, wherein the antibody is a human IgG2 antibody.

8. The engineered antibody of claim 5, wherein the antibody is a human IgG4 antibody.

9. The engineered antibody of claim 1, being glycosylated.

10. A pharmaceutical composition comprising the engineered antibody of claim 1, and a pharmaceutically acceptable carrier.

11. A kit, comprising:
a. the engineered antibody of claim 1; and
b. a transglutaminase.

12. An engineered monoclonal antibody, comprising:
an amino acid substitution at heavy chain position 302 of the antibody, wherein the substitution at heavy chain position 302 is V302S, V302A or V302T;
one of substitutions (A), (B), (C), (D), or (E), each specified as
(A) a glutamine substitution and an alanine substitution, wherein the glutamine substitution is at heavy chain position 286, 287, 288 or 289, and the alanine substitution is at heavy chain position 241 or 243,
(B) a glutamine substitution at heavy chain position 286, 287, 288 or 289,
(C) an alanine substitution at heavy chain position 241 or 243, provided that when the substitution at heavy chain position 302 is V302A, then the engineered monoclonal antibody further comprises amino acid substitution Y300L at heavy chain position 300,
(D) a glutamine substitution and an alanine substitution, wherein the glutamine substitution is at heavy chain position 286, 287, 288 or 289, and the alanine substitution is at heavy chain position 241, 243, 294 or 301,
(E) a glutamine substitution and an alanine substitution, wherein the glutamine substitution is at heavy chain position 286, 287, 288, 289, 290, 293 or 294, and the alanine substitution is at heavy chain position 241 or 243; and an endogenous heavy chain Q295 residue;

wherein the engineered monoclonal antibody is non-deglycosylated, and the amino acid numbering is according to the EU Index of Kabat.

13. The engineered antibody of claim 12, comprising a glutamine substitution and an alanine substitution, wherein the glutamine substitution is at heavy chain position 286, 287, 288 or 289, and the alanine substitution is at heavy chain position 241, 243, 294 or 301.

14. The engineered antibody of claim 12, comprising a glutamine substitution and an alanine substitution, wherein the glutamine substitution is at heavy chain position 286, 287, 288, 289, 290, 293 or 294, and the alanine substitution is at heavy chain position 241 or 243.

15. The engineered antibody of claim 12, wherein the amino acid substitution at heavy chain position 302 is V302A.

16. The engineered antibody of claim 12, wherein the amino acid substitution at heavy chain position 302 is V302S.

17. The engineered antibody of claim 12, further comprising an amino acid substitution at heavy chain position 300, wherein the amino acid substitution at heavy chain position 300 is Y300L, when the engineered antibody does not comprise substitution (C).

18. The engineered antibody of claim 12, wherein the antibody is a human IgG antibody.

19. The engineered antibody of claim 18, wherein the antibody is a human IgG1 antibody.

20. The engineered antibody of claim 18, wherein the antibody is a human IgG2 antibody.

21. The engineered antibody of claim 18, wherein the antibody is a human IgG4 antibody.

22. The engineered antibody of claim 12, being glycosylated.

23. A pharmaceutical composition comprising the engineered antibody of claim 12, and a pharmaceutically acceptable carrier.

24. A kit, comprising:
a. the engineered antibody of claim 12; and
b. a transglutaminase.

25. The engineered antibody of claim 13, wherein the amino acid substitution at heavy chain position 302 is V302A.

26. The engineered antibody of claim 13, wherein the amino acid substitution at heavy chain position 302 is V302S.

27. The engineered antibody of claim 13, further comprising an amino acid substitution at heavy chain position 300, wherein the amino acid substitution at heavy chain position 300 is Y300L.

28. The engineered antibody of claim 13, wherein the antibody is a human IgG antibody.

29. The engineered antibody of claim 28, wherein the antibody is a human IgG1 antibody.

30. The engineered antibody of claim 28, wherein the antibody is a human IgG2 antibody.

31. The engineered antibody of claim 28, wherein the antibody is a human IgG4 antibody.

32. The engineered antibody of claim 13, being glycosylated.

33. A pharmaceutical composition comprising the engineered antibody of claim 13, and a pharmaceutically acceptable carrier.

34. A kit, comprising:
a. the engineered antibody of claim 13; and
b. a transglutaminase.

35. The engineered antibody of claim 14, wherein the amino acid substitution at heavy chain position 302 is V302A.

36. The engineered antibody of claim 14, wherein the amino acid substitution at heavy chain position 302 is V302S.

37. The engineered antibody of claim 14, comprising the glutamine substitution at heavy chain position 294.

38. The engineered antibody of claim 14, further comprising an amino acid substitution at heavy chain position 300, wherein the amino acid substitution at heavy chain position 300 is Y300L.

39. The engineered antibody of claim 14, wherein the antibody is a human IgG antibody.

40. The engineered antibody of claim 39, wherein the antibody is a human IgG1 antibody.

41. The engineered antibody of claim 39, wherein the antibody is a human IgG2 antibody.

42. The engineered antibody of claim 39, wherein the antibody is a human IgG4 antibody.

43. The engineered antibody of claim 14, being glycosylated.

44. A pharmaceutical composition comprising the engineered antibody of claim 14, and a pharmaceutically acceptable carrier.

45. A kit, comprising:
a. the engineered antibody of claim 14; and
b. a transglutaminase.

\* \* \* \* \*